United States Patent
Toledo-Sherman et al.

(10) Patent No.: US 9,981,918 B2
(45) Date of Patent: May 29, 2018

(54) KYNURENINE-3-MONOOXYGENASE INHIBITORS, PHARMACEUTICAL COMPOSITIONS, AND METHODS OF USE THEREOF

(75) Inventors: Leticia M. Toledo-Sherman, Santa Monica, CA (US); Celia Dominguez, Los Angeles, CA (US); Michael Prime, Oxfordshire (GB); Peter Johnson, Oxfordshire (GB); Ignacio Muñoz-Sanjuán, West Hollywood, CA (US); Stephen Martin Courtney, Oxfordshire (GB); William Mitchell, Lincolnshire (GB); Christopher John Brown, Abingdon (GB); Paula C. De Aguiar Pena, Oxfordshire (GB)

(73) Assignee: CHDI Foundation, Inc., New York, NY (US)

( * ) Notice: Subject to any disclaimer, the term of this patent is extended or adjusted under 35 U.S.C. 154(b) by 175 days.

(21) Appl. No.: 14/241,374

(22) PCT Filed: Aug. 28, 2012

(86) PCT No.: PCT/US2012/052648
§ 371 (c)(1),
(2), (4) Date: Sep. 2, 2015

(87) PCT Pub. No.: WO2013/033085
PCT Pub. Date: Mar. 7, 2013

(65) Prior Publication Data
US 2016/0251318 A1    Sep. 1, 2016

Related U.S. Application Data

(60) Provisional application No. 61/528,998, filed on Aug. 30, 2011.

(51) Int. Cl.

| | | |
|---|---|---|
| *C07D 237/28* | (2006.01) | |
| *A61K 31/70* | (2006.01) | |
| *C07D 239/28* | (2006.01) | |
| *C07D 405/14* | (2006.01) | |
| *C07D 403/04* | (2006.01) | |
| *C07D 403/10* | (2006.01) | |
| *C07D 405/04* | (2006.01) | |
| *C07D 405/10* | (2006.01) | |
| *C07D 239/42* | (2006.01) | |
| *C07D 409/04* | (2006.01) | |
| *C07D 413/04* | (2006.01) | |
| *C07D 417/04* | (2006.01) | |
| *C07D 471/04* | (2006.01) | |
| *C07D 491/048* | (2006.01) | |
| *C07D 491/052* | (2006.01) | |
| *C07H 13/10* | (2006.01) | |

(Continued)

(52) U.S. Cl.
CPC ......... *C07D 239/28* (2013.01); *C07D 239/42* (2013.01); *C07D 401/04* (2013.01); *C07D 401/12* (2013.01); *C07D 403/04* (2013.01); *C07D 403/10* (2013.01); *C07D 403/12* (2013.01); *C07D 405/04* (2013.01); *C07D 405/10* (2013.01); *C07D 405/12* (2013.01); *C07D 405/14* (2013.01); *C07D 409/04* (2013.01); *C07D 413/04* (2013.01); *C07D 417/04* (2013.01); *C07D 471/04* (2013.01); *C07D 491/048* (2013.01); *C07D 491/052* (2013.01); *C07H 13/10* (2013.01)

(58) Field of Classification Search
CPC .. C07D 410/04; C07D 410/12; C07D 403/10; C07D 403/12; C07D 405/10; C07D 405/12; C07D 405/14; C07D 239/28; C07D 239/26; A61K 31/70
USPC ........................................ 544/242, 333, 334
See application file for complete search history.

(56) References Cited

U.S. PATENT DOCUMENTS

| | | |
|---|---|---|
| 3,707,560 A | 12/1972 | De Angelis et al. |
| 3,908,012 A | 9/1975 | De Angelis et al. |

(Continued)

FOREIGN PATENT DOCUMENTS

| | | |
|---|---|---|
| CN | 1566065 | 1/2005 |
| EP | 1679309 | 7/2006 |

(Continued)

OTHER PUBLICATIONS

Chemcast RN 1261956-00-6 (2016).*
Chemical entity, Wikepedia, p. 1-2 (2017).*
Chen et al. "Pyrimidine . . . " CA150:121675 (2009).*
Courtney&Scheel "Modulation of the . . . " Top Med. Chem. v. 6, p. 149-176 (2010).*
Fotsch et al. "Preparation of pyridylmethyl . . . " CA152:476968 (2010).*
Gellespie et al. "Preparation of pyrimidine . . . " CA143:248409).*
Kawamoto et al. "Preparation of biarylamide . . . " CA146:401963 (2007).*
Improper Markush, Fed. Reg. v.76(27) 7162-7175, slides 64-67 (2011).*
Banker "Modern Pharmaceutics" p. 451, 596 (2002).*
Wolff "Burger's medicinal . . . " p. 975-977 (1995).*
Patani et al. "Bioisosterism . . . " Chem Rev. 96, 3147-3176 (1996).*
Flaviano Giorgini et al, 2005, A genomic screen in yeast implicates kynurenine 3-monooxygenase as a therapeutic target for Huntington's disease.*

(Continued)

Primary Examiner — Rita J Desai
(74) Attorney, Agent, or Firm — Sheppard Mullin Richter & Hampton LLP

(57) ABSTRACT

Certain chemical entities are provided herein. Also provided are pharmaceutical compositions comprising at least one chemical entity and one or more pharmaceutically acceptable vehicle. Methods of treating patients suffering from certain diseases and disorders responsive to the inhibition of KMO activity are described, which comprise administering to such patients an amount of at least one chemical entity effective to reduce signs or symptoms of the disease or disorder are disclosed. These diseases include neurodegenerative disorders such as Huntington's disease. Also described are methods of treatment include administering at least one chemical entity as a single active agent or administering at least one chemical entity in combination with one or more other therapeutic agents. Also provided are methods for screening compounds capable of inhibiting KMO activity.

3 Claims, No Drawings

(51) Int. Cl.
*C07D 401/04* (2006.01)
*C07D 401/12* (2006.01)
*C07D 403/12* (2006.01)
*C07D 405/12* (2006.01)

(56) References Cited

U.S. PATENT DOCUMENTS

| | | | |
|---|---|---|---|
| 3,935,202 | A | 1/1976 | Wei et al. |
| 3,950,525 | A | 4/1976 | De Angelis et al. |
| 4,634,689 | A | 1/1987 | Witkowski et al. |
| 4,824,846 | A | 4/1989 | Kampe et al. |
| 4,920,119 | A | 4/1990 | Attwood et al. |
| 4,931,443 | A | 6/1990 | Nakao et al. |
| 5,064,832 | A | 11/1991 | Stanek et al. |
| 5,102,904 | A | 4/1992 | Kameswaran |
| 5,334,720 | A | 8/1994 | Schmiesing et al. |
| 5,338,739 | A | 8/1994 | Wettlaufer et al. |
| 5,439,912 | A | 8/1995 | Hubele |
| 5,446,067 | A | 8/1995 | Benoit et al. |
| 5,726,185 | A | 3/1998 | Alig et al. |
| 5,925,639 | A | 7/1999 | Doll et al. |
| 5,948,780 | A | 9/1999 | Peterson et al. |
| 6,008,220 | A | 12/1999 | Hupe et al. |
| 6,133,304 | A | 10/2000 | Peterson et al. |
| 6,169,103 | B1 | 1/2001 | Purchase et al. |
| 6,194,428 | B1 | 2/2001 | Urbahns et al. |
| 6,211,214 | B1 | 4/2001 | Kramer et al. |
| 6,214,822 | B1 | 4/2001 | Treiber et al. |
| 6,239,288 | B1 | 5/2001 | Purchase et al. |
| 6,248,765 | B1 | 6/2001 | Schwartz et al. |
| 6,251,926 | B1 | 6/2001 | Momose et al. |
| 6,288,063 | B1 | 9/2001 | Kluender et al. |
| 6,340,709 | B1 | 1/2002 | Bocan et al. |
| 6,399,612 | B1 | 6/2002 | Purchase et al. |
| 6,455,520 | B1 | 9/2002 | Brown et al. |
| 6,518,435 | B2 | 2/2003 | Yamane et al. |
| 6,541,521 | B1 | 4/2003 | Purchase et al. |
| 6,624,196 | B2 | 9/2003 | Purchase et al. |
| 7,022,725 | B2 | 4/2006 | Momose et al. |
| 7,049,318 | B2 | 5/2006 | Dominguez et al. |
| 7,105,549 | B2 | 9/2006 | Shao et al. |
| 7,345,178 | B2 | 3/2008 | Nunes et al. |
| 7,947,680 | B2 | 5/2011 | Jimenez et al. |
| 7,951,824 | B2 | 5/2011 | Jaeschke et al. |
| 7,994,338 | B2 | 8/2011 | Muchowski et al. |
| 8,071,631 | B2 | 12/2011 | Muchowski et al. |
| 8,198,275 | B2 | 6/2012 | Jimenez et al. |
| 8,536,186 | B2 * | 9/2013 | Wityak ............... C07D 213/79 514/256 |
| 8,883,785 | B2 | 11/2014 | Dominguez et al. |
| 9,145,373 | B2 * | 9/2015 | Wityak ............... C07D 213/79 514/256 |
| 9,260,422 | B2 * | 2/2016 | Dominguez ......... C07D 239/42 544/334 |
| 9,428,464 | B2 * | 8/2016 | Courtney ............. C07D 403/12 514/256 |
| 2002/0049207 | A1 | 4/2002 | McCarthy |
| 2004/0077557 | A1 | 4/2004 | Andreotti et al. |
| 2004/0204464 | A1 | 10/2004 | Al-Abed |
| 2004/0214817 | A1 | 10/2004 | Pierce et al. |
| 2004/0214888 | A1 | 10/2004 | Matsuura et al. |
| 2005/0070584 | A1 | 3/2005 | Havran et al. |
| 2005/0239854 | A1 | 10/2005 | Sugiyama et al. |
| 2005/0288308 | A1 | 12/2005 | Amrien et al. |
| 2006/0052606 | A1 | 3/2006 | Liebeschuetz et al. |
| 2006/0178388 | A1 | 8/2006 | Wrobleski et al. |
| 2006/0189806 | A1 | 8/2006 | Bernardini et al. |
| 2006/0223849 | A1 | 10/2006 | Mjalli et al. |
| 2006/0252751 | A1 | 11/2006 | Xue et al. |
| 2006/0252764 | A1 | 11/2006 | Guillemont et al. |
| 2006/0293339 | A1 | 12/2006 | Chakravarty et al. |
| 2007/0060573 | A1 | 3/2007 | Wortmann et al. |
| 2007/0275950 | A1 | 11/2007 | Miyata et al. |
| 2008/0019915 | A1 | 1/2008 | Hadida-Ruah et al. |
| 2008/0058391 | A1 | 3/2008 | Johnson et al. |
| 2008/0070937 | A1 | 3/2008 | Muchowski et al. |
| 2008/0077419 | A1 | 3/2008 | Santiago et al. |
| 2008/0113997 | A1 | 5/2008 | Sielecki-Dzurdz et al. |
| 2008/0187575 | A1 | 8/2008 | Kiebl et al. |
| 2008/0188452 | A1 | 8/2008 | Altenbach et al. |
| 2009/0036428 | A1 | 2/2009 | Kawakami et al. |
| 2009/0270405 | A1 | 10/2009 | Cook et al. |
| 2010/0022546 | A1 | 1/2010 | Jimenez et al. |
| 2010/0101643 | A1 | 4/2010 | Takahashi et al. |
| 2010/0152178 | A1 | 7/2010 | Osakada et al. |
| 2011/0015232 | A1 | 1/2011 | Charest et al. |
| 2011/0178086 | A1 | 7/2011 | Jimenez et al. |
| 2011/0183957 | A1 | 7/2011 | Wityak et al. |
| 2011/0230428 | A1 | 9/2011 | Wityak et al. |
| 2012/0041009 | A1 | 2/2012 | Mizuno |
| 2012/0329812 | A1 | 12/2012 | Wityak et al. |
| 2013/0029988 | A1 | 1/2013 | Dominguez et al. |
| 2013/0116216 | A1 | 5/2013 | Dominguez et al. |
| 2013/0331370 | A1 | 12/2013 | Wityak et al. |
| 2014/0329795 | A1 | 11/2014 | Courtney et al. |
| 2014/0329816 | A1 | 11/2014 | Dominguez et al. |
| 2015/0057238 | A1 | 2/2015 | Toledo-Sherman et al. |
| 2016/0257674 | A1 | 9/2016 | Dominguez et al. |
| 2016/0272611 | A1 | 9/2016 | Dominguez et al. |
| 2017/0209440 | A1 | 7/2017 | Dominguez et al. |

FOREIGN PATENT DOCUMENTS

| | | |
|---|---|---|
| EP | 1783116 | 5/2007 |
| EP | 1928842 | 6/2008 |
| EP | 2338887 | 6/2011 |
| EP | 2090570 | 12/2013 |
| FR | 2204406 | 5/1974 |
| JP | 01113377 | 5/1989 |
| JP | 07041459 | 2/1995 |
| JP | 2000198771 | 7/2000 |
| JP | 2002241358 | 8/2002 |
| JP | 2007-230963 | 9/2007 |
| JP | 2009-280521 | 12/2009 |
| WO | WO 95/23135 | 8/1995 |
| WO | WO 98/37079 A1 | 8/1998 |
| WO | WO 99/21583 | 5/1999 |
| WO | WO 01/34579 | 5/2001 |
| WO | WO 01/60781 | 8/2001 |
| WO | WO 2001/89457 | 11/2001 |
| WO | WO 02/060877 | 8/2002 |
| WO | WO 2002/085891 | 10/2002 |
| WO | WO 03/002536 | 1/2003 |
| WO | WO 03/022276 A1 | 3/2003 |
| WO | WO 03/029210 | 4/2003 |
| WO | WO 03/051833 | 6/2003 |
| WO | WO 03/066623 A1 | 8/2003 |
| WO | WO 2004/014844 A2 | 2/2004 |
| WO | WO 2004/032933 A1 | 4/2004 |
| WO | WO-2004026833 | 4/2004 |
| WO | WO 2004/058762 A1 | 7/2004 |
| WO | WO 2004/108686 | 12/2004 |
| WO | WO 2005/003123 A1 | 1/2005 |
| WO | WO 2005/037793 A1 | 4/2005 |
| WO | WO 2005/042498 A2 | 5/2005 |
| WO | WO 2005/079800 | 9/2005 |
| WO | WO 2005/079801 | 9/2005 |
| WO | WO 2005/079802 | 9/2005 |
| WO | WO 2005/095400 A1 | 10/2005 |
| WO | WO 2006/000371 | 1/2006 |
| WO | WO 2006/039718 | 4/2006 |
| WO | WO 2006/051270 | 5/2006 |
| WO | WO 2006/062093 A1 | 6/2006 |
| WO | WO 2006/086600 A1 | 8/2006 |
| WO | WO-2006133333 | 12/2006 |
| WO | WO 2007/017289 A2 | 2/2007 |
| WO | WO 2007/019416 A1 | 2/2007 |
| WO | WO 2007/024922 A1 | 3/2007 |
| WO | WO 2007/039470 | 4/2007 |
| WO | WO 2007/067836 A2 | 6/2007 |
| WO | WO 2007/070818 A1 | 6/2007 |
| WO | WO 2007/093542 | 8/2007 |
| WO | WO 2007/096072 | 8/2007 |
| WO | WO 2007/097403 | 8/2007 |

(56) References Cited

FOREIGN PATENT DOCUMENTS

| | | |
|---|---|---|
| WO | WO-2007087637 | 8/2007 |
| WO | WO 2008/002576 A2 | 1/2008 |
| WO | WO 2008/009963 A2 | 1/2008 |
| WO | WO 2008/022281 | 2/2008 |
| WO | WO 2008/022286 | 2/2008 |
| WO | WO 2008/023720 A1 | 2/2008 |
| WO | WO 2008/034008 A2 | 3/2008 |
| WO | WO 2008/095852 A1 | 8/2008 |
| WO | WO 2008/121877 A2 | 10/2008 |
| WO | WO 2008/152099 A2 | 12/2008 |
| WO | WO 2009/006389 | 1/2009 |
| WO | WO 2009/082346 A1 | 7/2009 |
| WO | WO 2009/148004 A1 | 12/2009 |
| WO | WO 2010/005783 A1 | 1/2010 |
| WO | WO 2010/017179 | 2/2010 |
| WO | WO 2010/020432 | 2/2010 |
| WO | WO 2010/044404 | 4/2010 |
| WO | WO 2010/045188 | 4/2010 |
| WO | WO 2010/052448 | 5/2010 |
| WO | WO 2010/055077 | 5/2010 |
| WO | WO 2010/079443 | 7/2010 |
| WO | WO 2010/100475 A1 | 9/2010 |
| WO | WO 2010/117323 | 10/2010 |
| WO | WO 2010/125402 | 11/2010 |
| WO | WO 2010/134478 A1 | 11/2010 |
| WO | WO 2011/008709 | 1/2011 |
| WO | WO 2011/043568 | 4/2011 |
| WO | WO 2011/046771 A1 | 4/2011 |
| WO | WO 2011/050323 A1 | 4/2011 |
| WO | WO 2011/091153 | 7/2011 |
| WO | WO 2011/104322 A1 | 9/2011 |
| WO | WO 2012/003387 A1 | 1/2012 |
| WO | WO 2012/035421 A2 | 3/2012 |
| WO | WO 2012/078777 | 6/2012 |
| WO | WO 2013/016488 A1 | 1/2013 |
| WO | WO 2013/033068 | 3/2013 |
| WO | WO 2013/033085 A1 | 3/2013 |
| WO | WO 2013/151707 | 10/2013 |

OTHER PUBLICATIONS

International Search Report issued in International Application No. PCT/US2012/52648 dated Nov. 2, 2012 (3 pages).
International Preliminary Report on Patentability along with Wirtten Opinion of the International Searching Authority for PCT/US2012/52648 dated Nov. 2, 2012 (5 pages).
Hurst et al., Intramolecular Diels-Alder reactions of α, β-unsaturated oxime ethers as 1-azadienes: synthesis of [c]-fused pyridines, *ScienceDirect*, Tetrahedron vol. 64 ,pp. 874-882, (2008).
Molina et al;, Unusual Reactivity of (Vinylimino) phosphoranes and Their Utility in the Preparation of Pyridine and Dihydropyridine Derivatives, *J. Organic Chemistry*, vol. 61, pp. 8094-8098, (1996).
Levin at al., Europium Catalyzed Intramolecular Oxazole Diels-Alder Reactions for the Synthesis of Benzopyrano [4,3-b]Pyridines and Benzo [h]-1,6-Naphthyridines, Tetrahedron Letters, vol. 30, No. 18, pp. 2355-2358 (1989).
Allen, "Pyrolysis of oximes of some y-cyano and y-nitro ketones," Canadian Journal of Chemistry (1965), 43(9), 2486-92.
Arzel, et al. A new synthesis of a-substituted 6-carbolines. Journal of Heterocyclic Chemistry vol. 34, Issue 4, pp. 1205-1210, 1997.
Berthel, et al., "Identification of phenyl-pyridine-2-carboxylic acid derivatives as novel cell cycle inhibitors with increased selectivity for cancer cells." Anti-Cancer Drugs, 13:359-366 (2002).
Blomquist et al., "Many-membered carbon rings. XVII. A paracyclophane possessing two gem-dimethyl groups," Journal of the American Chemical Society (1958), 80, 3405-8.
Bredereck, et al., "Foramid-Reaktionen, VIII. Eine neue pyrimidinsynthese." Chemische Berichte 90:942-52 (1957).
Brinkmann et al., 9 NATURE Reviews | Drug Discovery, 883-897 (2010).
Brown et al., "Product class 16: benzisothiazoles," Science of Synthesis (2002), 11, 573-625.

Bundgaard, Design of Prodrugs, Elsevier, 1985.
Chatterjea, et al., "Synthesis in 3-azafluorene group. Part III." J. Indian Chem. Soc., vol. LXI, 1028-1031 (1984).
Chemical Abstracts Service. CAS Reg. No. 1017484-83-1 (Apr. 27, 2008).
Chemical Abstracts Service. CAS Reg. No. 1017484-87-5 (Apr. 27, 2008).
Chemical Abstracts Service. CAS Reg. No. 1017484-91-1 (Apr. 27, 2008).
Chemical Abstracts Service. CAS Reg. No. 1017484-95-5 (Apr. 27, 2008).
Chemical Abstracts Service. CAS Reg. No. 52565-56-7 (1984), 1p.
Chemical Abstracts Service. CAS Reg. No. 55240-51-2 (1984), 1 p.
Chemical Abstracts Service. CAS Reg. No. 887407-77-4 (2006), 1 p.
Chemical Abstracts Service. CAS Reg. No. 1017394-18-1 (Apr. 25, 2008).
Chemical Abstracts Service. CAS Reg. No. 1017396-21-2 (Apr. 25, 2008).
Chemical Abstracts Service. CAS Reg. No. 1017396-26-7 (Apr. 25, 2008).
Chemical Abstracts Service. CAS Reg. No. 1017396-31-4 (Apr. 25, 2008).
Chemical Abstracts Service. CAS Reg. No. 1017438-20-8 (Apr. 25, 2008).
Chemical Abstracts Service. CAS Reg. No. 1017438-24-2 (Apr. 25, 2008).
Chemical Abstracts Service. CAS Reg. No. 1017438-28-6 (Apr. 25, 2008).
Chemical Abstracts Service. CAS Reg. No. 1017438-32-2 (Apr. 25, 2008).
Chemical Abstracts Service. CAS Reg. No. 1017438-36-6 (Apr. 25, 2008).
Chemical Abstracts Service. CAS Reg. No. 1017484-79-5 (Apr. 27, 2008).
Chemical Abstracts Service. CAS Reg. No. 1017484-99-9 (Apr. 27, 2008).
Chiarugi et al. J. Neurochem. 2001, 77, 1310-1318.
Child et al., "Fenbufen, a new anti-inflammatory analgesic: synthesis and structure-activity relations of analogs," Journal of Pharmaceutical Sciences (1977), 66(4), 466-76.
Clapham et al., Trifluoromethyl-substituted pyridyl- and pyrazolylboronic acids and esters: synthesis and Suzuki-Miyaura cross-coupling reactions, Organic & Biomolecular Chemistry, 7(10), pp. 2155-2161 (2009).
Collins, 1 Current Signal Transduction Therapy, 13-23, 13 (2006).
Connor et al., 441 Neuroscience Letters, 29-34 (2008).
Dalal et al. "Substituted Butyro Lactones. Part III. Synthesis of γ-(4-alkoxy-3- chlorophenyl)butyrolactones." J. Ind. Chem. 1958, 35, 742.
Damasio, Alzheimer's Disease and Related Dementias, Cecil Textbook of Medicine, 20th Edition, vol. 2, pp. 1992-1996, 1996.
Database Registry, Chemical Library Supplier: Ambinte, Entered STN: Apr. 25, 2008. (RN No. 1017438-16-2).
Douglas, Jr. Introduction to Viral Diseases, Cecil Textbook of Medicine, 20th Edition, vol. 2, pp. 1739-1747, 1996.
Eglinton, et al., "The chemistry of fungi. Part XXXV. A preliminary investigation of ergoflavin." View Online/Journal Homepage, 1833-1842 (1958).
EP Application No. 09805426. Suppl. Search Report dated Feb. 2, 2012.
Filosa, et al., "Synthesis and antiproliferative properties of N3/8-disubstituted 3,8-diazabicyclo[3.2.1]octane analogues of 3,8-bis[2-(3,4,5-trimethoxyphenyl)pyridine-4-yl]methyl-piperazine." Eur. J. Med. Chem. 42:293-306 (2007).
Furuya et al. "Cyanuric Chloride as a Mild and Active Beckmann Rearrangement Catalyst ," Journal of the American Chemical Society (2005), 127(32), 11240-11241.
Giorgini et al., 37 Nature Genetics, 526-531 (2005).
Girouard et al., 100 Journal of Applied Physiology, 328-335, 332 (2006).
Goldfarb, CAPLUS Abstract 151:92839 (2009).
Gregoire et al., 186 Behavioural Brain Research, 161-167 (2008).

(56) References Cited

OTHER PUBLICATIONS

Gura et al., Systems for identifying new drugs are often faulty, Science, 278:1041-1042, 1997.
Hametner et al., CAPLUS Abstract 135:241866 (2001).
Han, et al., "Lead optimization studies on FimH antagonists: discovery of potent and orally bioavailable ortho-substituted biphenyl mannosides." J. Med. Chem. 55:3945-3959 (2012).
Hassner et al., "Cycloadditions. 43. Stereospecific synthesis of functionalized Cyclopentanes," Tetrahedron Letters (1989), 30(42), 5803-6.
Hoffman et al., CAPLUS Abstract 117:7954 (1992).
Imoto et al. "Studies on non-thiazolidinedione antidiabetic agents. 2. Novel oxyiminoalkanoic acid derivatives as potent glucose and lipid lowering agents," Chemical & Pharmaceutical Bulletin (2003), 51(2), 138-151.
International Preliminary Report on Patentability, PCT/US2009/052667 (dated Feb. 8, 2011).
International Search Report and Written Opinion of PCT/US2015/040848 dated Oct. 23, 2015 (18 pages).
Johnson et al., Relationships between drug activity in NCI preclinical in vitro and in vivo models and early clinical trials, British Journal of Cancer, 84(10):1424-1431,2001.
Kato et al. CAPLUS Abstract 73:77194 (1970).
Kato et al., "The Vilsmeier reaction of methylpyrimidine derivatives." Yakugaku Zasshi 90(7):870-876 (1970).
Kemp et al., "N-Ethylbenzisoxazolium cation. I. Preparation and reactions with nucleophilic species," Tetrahedron (1965), 21(11), 3019-35.
Khachatryan et al. "Synthesis and heterocyclization of b-aroyl-a-diphenyl-phosphorylpropionic acids," Chemistry of Heterocyclic Compounds (New York, NY, United States) (Translation of Khimiya Geterotsiklicheskikh Soedinenii) (2004), 40(4), 446-451.
Khachikyan et al. "Reaction of b-Aroylacrylic Acids with Triphenylphosphine Hydrobromide and Certain Reactions of the Resulting Products," Russian Journal of General Chemistry (2005), 75(12), 1895-1898.
Kobayashi, et al., "A novel strategy for the synthesis of 2-arylpyridines using one-pot 6 π-azaelectrocyclization." Tetrahedron Ltrs., 49:4349-4351 (2008).
Kohler et al., "Isoxazoline oxides," Journal of the American Chemical Society (1926), 48, 2425-34.
Kort, et al., "Subtype-selective Nav1.8 sodium channel blockers: Identification of potent orally active nicotinamide derivatives." Bioorg. & Med. Chem. Ltrs. 20:6812-6815 (2010).
Kulkarni, et al., "Design and synthesis of novel heterobiaryl amides as metabotropic glutamate receptor subtype 5 antagonists." Bioorg. & Med. Chem. Ltrs. 17:2074-2079 (2007).
Lafferty et al. "The preparation and properties of certain pyridylpyrimidines and bidiazines as potential chelating agents for Iron(II)" J. Org. Chem. 1967, 32, 1591-1596.
Layzer, Degenerative Diseases of the Nervous System, Cecil Textbook of Medicine, 20th Edition, vol. 2, pp. 2050-2057, 1996.
LeWitt, 359 New England Journal of Medicine, 2468-2473 (2008).
Li, et al., "Discovering novel chemical inhibitors of human cyclophilin A: virtual screening, synthesis, and bioassay." Bioorganic & Medicinal Chemistry, 14:2209-2224 (2006).
Masaki et al., "Dehydration of 4-oximinocarboxylic acids with dicyclohexylcarbodiimide," Journal of Heterocyclic Chemistry (1965), 2(4), 376-8.
Mason et al., "Some Aryl Substituted 2-(4-Nitrophenyl)-4-oxo-4-phenylbutanoates and 3-(4-Nitrophenyl)-1-phenyl-1,4-butanediols and Related Compounds as Inhibitors of Rat Liver Microsomal Retinoic Acid Metabolising Enzymes," Journal of Enzyme Inhibition and Medicinal Chemistry (2003), 18(6), 511-528.
Maurin et al., "Structure of (E)-4-benzoylbutyramide oxime," Acta Crystallographica, Section C: Crystal Structure Communications (1992), C48(10), 1819-20.
Maurin et al., "Structures of 4-hydroxyimino-4-phenylbutanoic acid, C10H11NO3 (I), and 5-hydroxyimino-5-phenylpentanoic acid, C11H13NO3 (II), at 223 K," Acta Crystallographica, Section C: Crystal Structure Communications (1994), C50(1), 78-81.
McKinnon et al., "Fused heterocycles from o-acylbenzenethiol derivatives," Canadian Journal of Chemistry (1988), 66(6), 1405-9.
Migliara et al., "A new route for the preparation of pyrazolo[3,4-c]pyridines," Journal of Heterocyclic Chemistry (1979), 16(3), 577-9.
Migliara et al., "Synthesis of 1-hydroxy-2,4-diphenylpyrrolo[2,3-d]pyridazin-7(6H)-one," Journal of Heterocyclic Chemistry (1979), 16(1), 203.
Mikhaleva et al., CAPLUS Abstract 91:107951 (1979).
Mitchell et al., 369 The Lancet, 2031-2041 (2007).
Molina, et al., "Electrocylization of 3-azahexa-1,3,5-trienes: a convenient iminophosphorane-mediated preparation of 4-arylpyridines." Tetrahedron Ltrs. 34(23):3773-3776 (1993).
Molyneux, "The resorcinol-maleic anhydride condensation product. An unequivocal proof of structure," Journal of Organic Chemistry (1978), 43(13), 2730-1.
Nerurkar et al., "b-Arylglutaconic acids. IV. Synthesis of crotono- and valerolactones of b-arylglutaconic and glutaric acids," Journal of Organic Chemistry (1960), 25, 1491-5.
Oare et al., "Acyclic stereoselection. 46. Stereochemistry of the Michael addition of N,N-disubstituted amide and thioamide enolates to a,b-unsaturated ketones," Journal of Organic Chemistry (1990), 55(1), 132-57.
O'Brien et al., 2 The LANCET Neurology, 89-98, 96 (2003).
Osborne et al., "The chemistry of triazine derivatives II. The acylation of 2,4,6-trimethyl-s-triazine to triazinyl ketones and their facile isomerization to acetamidopyrimidines." J. Heterocyclic Chem. 1 (Jul. 1, 1964) pp. 145-150 (1964).
Overmars et al., "Fluvoxamine maleate: metabolism in man," European Journal of Drug Metabolism and Pharmacokinetics (1983), 8(3), 269-80.
Papet et al., CAPLUS Abstract 119:271098 (1993).
PCT/US2009/052560, International Search Report and Written Opinion, dated Sep. 29, 2009, 8 pages.
PCT/US2009/052667. International Search Report & Written Opinion dated Oct. 13, 2009.
PCT/US2011/021890. International Search Report dated Mar. 29, 2011.
PCT/US2012/052617. International Search Report & Written Opinion dated Oct. 22, 2012.
PCT/US2012/48254. International Search Report & Written Opinion dated Sep. 24, 2012.
Pearce et al., Failure modes in anticancer drug discovery and development, Cancer Drug Design and Discovery Edited by Stephen Neidle, Chapter 18, pp. 424-435 (2008).
Pimentel and McClellan, The Hydrogen Bond, Freeman, San Francisco, 1960.
Poupaert, Drug Design: Basic Principles and Applications, in 2 Encyclopedia of Pharmaceutical Technology 1362-1369, 1367 (James Swarbrick ed., 3rd ed., 2007).
Pratsch, et al., "Hydroxy- and aminophenyl radicals from arenediazonium salts." Chem. Eur. J. 17:4104-4108 (2011).
Proctor, et al., "Bridged-ring nitrogen compounds. part 5,1 synthesis of 2,6-methano-3-benzazonine ring-systems." JCS Perkin I, 1754-1762 (1981).
Sakaguchi, et al., "Library-directed solution- and solid-phase synthesis of 2,4-disubstituted pyridines: one-pot approach through 6 π-azaelectrocyclization." Chem. Asian. J. 4:1573-1577 (2009).
Sakamoto, et al. "Studies on pyrimidine derivatives. XV. Homolytic acylation and amidation of simply substituted pyrimidines." Chem. Pharm. Bull. 1980, 28, 202-207.
Sakamoto, et al., "Studies on pyrimidine derivatives. XVI. site selectivity in the homolytic substitution of simple pyrimidines." Chem. Pharm. Bull. 1980, 28, 571-577.
Saravanan et al., "Tandem Ring Opening and Oximation of Ethyl 3-Aroyl-1-cyano-4hydroxy-2,4,6-triarylcyclohexanecarboxylate by Hydroxylamine," Synthetic Communications (2007), 37(20), 3635-3648.

(56) References Cited

OTHER PUBLICATIONS

Sasse et al. "New Histamine H3-Receptor Ligands of the Proxifan Series: Imoproxifan and Other Selective Antagonists with High Oral in Vivo Potency," Journal of Medicinal Chemistry (2000), 43(17), 3335-3343.
Sathyasaikumar et al., Dysfunctional Kynurenine Pathway Metabolism in the R6/2 Mouse Model of Huntington's Disease, J Neurochem. 113(6), pp. 1416-1425, Jun. 2010.
Savarin et al. "Novel Intramolecular Reactivity of Oximes: Synthesis of Cyclic and Spiro-Fused Imines," Organic Letters (2007), 9(6), 981-983.
Saygili et al., CAPLUS Abstract 141:7086 (2004).
Schilt et al., CAPLUS Abstract 85:186182 (2 pages) (1976).
Schwarcz et al., 13 Nature Reviews I Neuroscience, 465-474 (2012).
Shah et al., 52 Biomedicine & Pharmacotherapy, 199-207 (2008).
Shao, et al., Phenoxyphenyl pyridines as novel state-dependent, high-potency sodium channel inhibitors. J. Med. Chem. 47:4277-4285 (2004).
Silverman, Prodrugs and Drug Delivery Systems, The Organic Chemistry of Drug Design and Drug action, Chapter 8, pp. 352-400, 1992.
Simone, Oncology: Introduction, Cecil Textbook of Medicine, 20th Edition, vol. 1, pp. 1004-1010, 1995.
Stevens et al., "Chemistry and structure of mitomycin C," Journal of Medicinal Chemistry (1965), 8(1), 1-10.
Tanimoto et al., "Synthesis of 6-alkoxy-3-aryl-6-(trimethylsilyloxy)-5,6-dihydro-4H-1,2-oxazines and their acid catalyzed hydrolysis leading to 3-aryl-5,6-dihydro-4H-1,2-oxazin-6-ones and (or) 4-aryl-4-(hydroxyimino)butyric acid esters," Journal of the Chemical Society, Perkin Transactions 1: Organic and Bio-Organic Chemistry (1972-1999) (1991), (12), 3153-7.
Testa, et al. Prodrug Design in, 5 Encyclopedia of Pharmaceutical Technology, 3008-3014 (J. Swarbrick ed., 3rd Ed. 2007).
Tomoeda et al., "A synthesis of 5-benzyl-2-pyrrolidinone," Yakugaku Zasshi (1966), 86(12), 1213-16.
Van Der Zanden et al., "Action of BF3-ether upon methylchavicol, the oximes of g-p-methoxy- and g-p-ethoxybenzoylbutyric acids and the oxime of benzophenone," Recueil des Travaux Chimiques des Pays-Bas et de la Belgique (1942), 61, 280-4.
Van Der Zanden et al., "Reduction products of g-anisoylbutyric acid, its oxime and the ethoxy homologs," Recueil des Travaux Chimiques des Pays-Bas et de la Belgique (1942), 61, 365-72.
Van Der Zanden, et al., "Polymers of methylchavicol. 1,5-Dianisyl-4-methyl-1-pentene," Recueil des Travaux Chimiques des Pays-Bas et de la Belgique (1943), 62, 383-92.
Van Muijlwijk-Koezen, et al., "Thiazole and thiadiazole analogues as a novel class of adenosine receptor antagonists." J. Med. Chem. 44:749-762 (2001).
Von Angerer, "Product class 12: pyrimidines." Science of Synthesis Houben-Weyl Methods of Molecular Transformations, Category 2, vol. 16 (2003).
Warshakoon, et al., "Design and synthesis of substituted pyridine derivatives as HIF-1α prolyl hydroxylase inhibitors." Bioorganic & Medicinal Chemistry Lett. 16:5616-5620 (2006).
Wienhoefer et al., CAPLUS Abstract 81 :169509 (1974).
Wilkerson et al. (Eur. J. Med. Chem., 1992, 27(6), 595).
WO2011091153 (PCT/US2011/021890) International Preliminary Report on Patentability dated Jul. 31, 2012.
WO2013/033085 International Search Report dated Nov. 2, 2012.
Written Opinion of the International Search Authority for PCT/US2009/004244, dated Sep. 14, 2009.
Zon et al., Nature Reviews Drug Discovery 4, 35 (2005).
Clercq. Anti-HIV drugs: 25 compounds approved within 25 years after the discovery of HIV. International Journal of Antimicrobial Agents. 2009; 33:307-320.
Dounay, et al. Challenges and Opportunities in the Discovery of New Therapeutics Targeting the Kynurenine Pathway. J Med Chem. Nov. 25, 2015;58(22):8762-82. doi: 10.1021/acs.jmedchem.5b00461. Epub Aug. 5, 2015.
Stone, et al. Kynurenine pathway inhibition as a therapeutic strategy for neuroprotection. FEBS J. Apr. 2012;279(8):1386-97. doi: 10.1111/j.1742-4658.2012.08487.x. Epub Mar. 27, 2012.
Wonodi, et al. Downregulated kynurenine 3-monooxygenase gene expression and enzyme activity in schizophrenia and genetic association with schizophrenia endophenotypes. Arch Gen Psychiatry. Jul. 2011;68(7):665-74. doi: 10.1001/archgenpsychiatry.2011.71.

\* cited by examiner

KYNURENINE-3-MONOOXYGENASE INHIBITORS, PHARMACEUTICAL COMPOSITIONS, AND METHODS OF USE THEREOF

This applications claims the benefit under 35 U.S.C. § 371 of PCT International Application No. PCT/US12/52648, filed Aug. 28, 2012, which in turn claims the benefit of priority of U.S. Application No. 61/528,998, filed Aug. 30, 2011, which is incorporated herein in its entirety for all purposes.

Provided herein are certain kynurenine-3-monooxygenase inhibitors, pharmaceutical compositions thereof, and methods of their use.

Kynurenine-3-monooxygenase (KMO) is an enzyme in the tryptophan degradation pathway that catalyzes the conversion of kynurenine (KYN) into 3-hydroxykynurenine (3-HK), which is further degraded to the excitotoxic NMDA receptor agonist QUIN (3-hydroxyanthranilate oxygenase). 3-OH-KYN and QUIN act synergistically, i.e. 3-OH-KYN significantly potentiates the excitotoxic actions of QUIN. Studies from several laboratories have provided evidence that the shift of KYN pathway metabolism away from the 3-OH-KYN/QUIN branch to increase the formation of the neuroprotectant KYNA in the brain leads to neuroprotection. In addition to having effects in the brain, the inhibition of KMO is further contemplated to impact peripheral tissues. Thus, the inhibition of KMO may be useful in the treatment of peripheral diseases as well as diseases of the brain. Furthermore, the relationship between KMO inhibition and elevations in AA (Anthranilic acid) could also have significant biological effects.

It has also been reported that KMO expression increases in inflammatory conditions or after immune stimulation. 3-OH-KYN, the product of its activity, accumulates in the brain of vitamin B-6 deficient neonatal rats and it causes cytotoxicity when added to neuronal cells in primary cultures or when locally injected into the brain. Recently, it was reported that relatively low concentrations (nanomolar) of 3-OH-KYN may cause apoptotic cell death of neurons in primary neuronal cultures. Structure-activity studies have in fact shown that 3-OH-KYN, and other o-amino phenols, may be subject to oxidative reactions initiated by their conversion to quinoneimines, a process associated with concomitant production of oxygen-derived free radicals. The involvement of these reactive species in the pathogenesis of ischemic neuronal death has been widely studied in the last several years and it has been shown that oxygen derived free radicals and glutamate mediated neurotransmission co-operate in the development of ischemic neuronal death.

It was also recently demonstrated that KMO activity is particularly elevated in the iris-ciliary body and that neo-formed 3-OH-KYN is secreted into the fluid of the lens. An excessive accumulation of 3-OH-KYN in the lens may cause cataracts.

QUIN is an agonist of a subgroup of NMDA receptors and when directly injected into brain areas it destroys most neuronal cell bodies sparing fibers en passant and neuronal terminals. QUIN is a relatively poor agonist of the NMDA receptor complex containing either NR2C or NR2D subunits, while it interacts with relatively high affinity with the NMDA receptor complex containing NR2A and NR2B subunits. The neurotoxicity profile found after intrastriatal injection of QUIN resembles that found in the basal nuclei of Huntington's disease patients: while most of the intrinsic striatal neurons are destroyed, NADH-diaphorase-staining neurons (which are now considered able to express nitric oxide synthetase) and neurons containing neuropeptide Y seem to be spared together with axon terminals and fiber en passant.

In vivo-infusion of KYNA has shown to modulate synaptic release of critical neurotransmitters implicated in cognitive processes and affective mental faculties, such as Acetylcholine, dopamine, and glutamate; therefore elevation of KYNA in brain can have effects in cognitive disorders and disorders arising from, or influenced by, changes in the levels of the neurotransmitters glutamate, dopamine, or Ach (such as Alzheimers, MCI, PD, schizophrenia, HD, OCD, Tourette's).

In vitro, the neurotoxic effects of the compound have been studied in different model systems with variable results: chronic exposure of organotypic cortico-striatal cultures to submicromolar concentration of QUIN causes histological signs of pathology, similar results have been obtained after chronic exposure of cultured neuronal cells.

In models of inflammatory neurological disorders such as experimental allergic encephalitis, bacterial and viral infections, forebrain global ischemia or spinal trauma, brain QUIN levels are extremely elevated. This increased brain QUIN concentration could be due to either an elevated circulating concentration of the excitotoxin or to an increased de novo synthesis in activated microglia or in infiltrating macrophages. In retrovirus-infected macaques, it has been proposed that most of the increased content of brain QUIN (approximately 98%) is due to local production. In fact, a robust increase in the activities of IDO, KMO and kynureninase has been found in areas of brain inflammation.

Previous studies have shown that agents able to increase brain KYNA content cause sedation, mild analgesia, increase in the convulsive threshold and neuroprotection against excitotoxic or ischemic damage. In addition to the above reported evidences, it has been recently demonstrated that a number of compounds able to increase brain KYNA formation may cause a robust decrease in glutamate (GLU) mediated neurotransmission by reducing GLU concentrations in brain extracellular spaces.

There remains a need for compounds that are effective inhibitors of KMO and may be used in treating neurodegenerative disorders.

Provided is at least one chemical entity chosen from compounds of Formula I

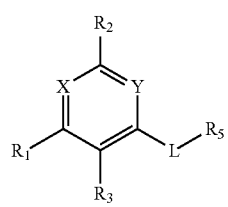

Formula I and pharmaceutically acceptable salts and prodrugs thereof wherein:

X and Y are independently chosen from —N— and —CH—, provided that at least one of X and Y is —N—;

$R_1$ is aryl or monocyclic heteroaryl, each of which is substituted with
a first group of the formula —Z—$R_6$ wherein
Z is chosen from —O—, —S—, —S(O)—, —S(O)$_2$—, —$CR_{11}R_{12}$—, —$OCR_{11}R_{12}$—, —$NR_{13}$—, —$NR_{13}CR_{11}R_{12}$—, —$CR_{11}R_{12}NR_{13}$—, and —C(O)— where $R_{11}$, $R_{12}$, and $R_{13}$ are independently chosen from hydrogen, lower alkyl, hydroxyl, and lower alkoxy,
$R_6$ is chosen from hydrogen, optionally substituted $C_1$-$C_6$ alkyl, optionally substituted cycloalkyl, optionally substituted aryl, optionally substituted heteroaryl, and optionally substituted heterocycloalkyl, provided that if Z is —O—, then $R_6$ is not optionally substituted benzyl or optionally substituted pyridylmethyl, or
$R_6$ and $R_{13}$, taken together with the nitrogen to which they are bound form an optionally substituted 5- to 7-membered heterocycloalkyl ring, and
a second group chosen from halo and lower alkyl optionally substituted with halo, or
$R_1$ is chosen from 2,3-dihydrobenzofuran-5-yl, chroman-6-yl, 1,3-benzodioxol-5-yl, 2,3-dihydro-1,4-benzodioxin-6-yl, 1,3-benzoxazol-5-yl, benzoimidazol-5-yl, 1,3-benzoxazol-6-yl, 2-oxo-2,3-dihydro-1,3-benzoxazol-5-yl, benzothiophen-5-yl, benzothiazol-5-yl, benzofuran-5-yl, 1H-indol-5-yl, 1H-indazol-5-yl, isoindolin-5-yl, benzo[c][1,2,5]oxadiazol-5-yl, 1,2,3,4-tetrahydroquinolin-6-yl, imidazo[1,2-a]pyridin-6-yl, pyrazolo[1,5-a]pyridine-5-yl, quinolin-6-yl, quinazolin-6-yl, quinazolin-7-yl, and quinoxalin-6-yl, each of which is optionally substituted, or
$R_1$ and $R_3$, taken together with intervening atoms form a bicyclic ring of the formula

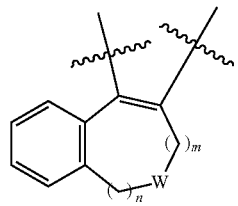

which is optionally substituted where m is 0 or 1 and n is 0 or 1, provided that at least one of m and n is 1 and W is —O—, or —N($R_8$)— where $R_8$ is hydrogen or lower alkyl;
$R_2$ is chosen from hydrogen and optionally substituted lower alkyl;
$R_3$ is chosen from hydrogen, halo, optionally substituted lower alkyl, hydroxyl, optionally substituted lower alkoxy, and optionally substituted amino;
L is chosen from —C(O)—, —C(O)O—, —C(O)N($R_4$)—, —C(O)N($OR_7$)—, —N($R_4$)S(O)$_2$—, —S(O)$_2$N($R_4$)—, and —C(O)N($R_4$)—S(O)$_2$—;
$R_4$ is chosen from hydrogen and lower alkyl;
$R_5$ is chosen from hydrogen, optionally substituted lower alkyl, optionally substituted aryl, optionally substituted heteroaryl, optionally substituted cycloalkyl, and optionally substituted heterocycloalkyl; provided that when L is —N($R_4$)S(O)$_2$—, then $R_5$ is not hydrogen, or
$R_4$ and $R_5$ taken together with the nitrogen to which they are bound form an optionally substituted 4- to 7-membered heterocycloalkyl ring, which is optionally fused to an optionally substituted cycloalkyl, optionally substituted heterocycloalkyl, optionally substituted aryl or optionally substituted heteroaryl ring; or
$R_3$ and $R_5$, taken together with the intervening atoms, form an optionally substituted 5- to 7-membered ring; and
$R_7$ is chosen from hydrogen and lower alkyl;
provided that the compound of Formula I is not chosen from
6-(3-chloro-4-methyl-phenyl)-pyrimidine-4-carboxylic acid methyl ester;
6-(3-chloro-4-methyl-phenyl)-pyrimidine-4-carboxylic acid;
6-(3-chloro-4-methoxy-phenyl)-pyrimidine-4-carboxylic acid methyl ester; and
6-(3-chloro-4-methoxy-phenyl)-pyrimidine-4-carboxylic acid.

Also provided is a pharmaceutical composition comprising at least one chemical entity described herein and at least one pharmaceutically acceptable excipient.

Also provided is a method of treating a condition or disorder mediated by Kynurenine 3-mono-oxygenase activity in a subject in need of such a treatment which method comprises administering to the subject a therapeutically effective amount of at least one chemical entity described herein.

Also provided is a method of treating a condition or disorder mediated by Kynurenine 3-mono-oxygenase activity in a subject in need of such a treatment which method comprises administering to the subject a therapeutically effective amount of at least one chemical entity described herein.

Also provided is a packaged pharmaceutical composition comprising at least one pharmaceutical composition described herein and instructions for using the composition to treat a subject suffering from a condition or disorder mediated by Kynurenine 3-mono-oxygenase activity.

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —CONH$_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having 1 to 4 carbons.

"Cycloalkyl" indicates a saturated hydrocarbon ring group, having the specified number of carbon atoms, usually from 3 to 7 ring carbon atoms. Examples of cycloalkyl groups include cyclopropyl, cyclobutyl, cyclopentyl, and cyclohexyl as well as bridged and caged saturated ring groups such as norbornane.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. An alkoxy group is further meant to encompass a cycloalkyl group, as defined above, that is likewise attached through an oxygen bridge. Alkoxy groups will usually have from 1 to 6 carbon atoms attached through the oxygen bridge. "Lower alkoxy" refers to alkoxy groups having 1 to 4 carbons.

"Aryl" encompasses:
5- and 6-membered carbocyclic aromatic rings, for example, benzene;
bicyclic ring systems wherein at least one ring is carbocyclic and aromatic, for example, naphthalene, indane, and tetralin; and
tricyclic ring systems wherein at least one ring is carbocyclic and aromatic, for example, fluorene.

For example, aryl includes 5- and 6-membered carbocyclic aromatic rings fused to a 5- to 7-membered heterocycloalkyl ring containing 1 or more heteroatoms chosen from N, O, and S, provided that the point of attachment is at the carbocyclic aromatic ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

The term "halo" includes fluoro, chloro, bromo, and iodo, and the term "halogen" includes fluorine, chlorine, bromine, and iodine.

"Heteroaryl" encompasses:
5- to 7-membered aromatic, monocyclic rings containing one or more, for example, from 1 to 4, or In some embodiments, from 1 to 3, heteroatoms chosen from N, O, and S, with the remaining ring atoms being carbon; and
bicyclic heterocycloalkyl rings containing one or more, for example, from 1 to 4, or In some embodiments, from 1 to 3, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl ring. For example, heteroaryl also includes a 5- or 6-membered heterocycloalkyl, aromatic ring fused to a 5- to 7-membered aryl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolyl, isoxazolinyl, oxazolyl, oxazolinyl, oxadiazolyl, thiazolinyl, thiadiazolinyl, tetrazolyl, thienyl, benzothiophenyl, furanyl, benzofuranyl, benzoimidazolinyl, benzooxazolyl, indolinyl, pyridizinyl, triazolyl, quinolinyl, pyrazolyl, and 5,6,7,8-tetrahydroisoquinoline. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

Substituted heteroaryl also includes ring systems substituted with one or more oxide ($—O^-$) substituents, such as pyridinyl N-oxides.

By "heterocycloalkyl" is meant a single aliphatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. "Heterocycloalkyl" also refers to 5- and 6-membered carbocyclic aromatic rings fused to a 5- to 7-membered heterocycloalkyl ring containing 1 or more heteroatoms chosen from N, O, and S, provided that the point of attachment is at the heterocycloalkyl ring. Suitable heterocycloalkyl groups include, for example (as numbered from the linkage position assigned priority 1), 2-pyrrolinyl, 2,4-imidazolidinyl, 2,3-pyrazolidinyl, 2-piperidyl, 3-piperidyl, 4-piperdyl, and 2,5-piperzinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

The term "substituted", as used herein, means that any one or more hydrogens on the designated atom or group is replaced with a selection from the indicated group, provided that the designated atom's normal valence is not exceeded. When a substituent is oxo (i.e., $=O$) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl (including without limitation lower alkyl), cycloalkyl, aryl (including without limitation phenyl), heterocycloalkyl (including without limitation morpholin-4-yl, 3,4-dihydroquinolin-1(2H)-yl, indolin-1-yl, 3-oxopiperazin-1-yl, piperidin-1-yl, piperazin-1-yl, pyrrolidin-1-yl, azetidin-1-yl, and isoindolin-2-yl), and heteroaryl (including without limitation pyridinyl), unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, —$O(C_1\text{-}C_2\ \text{alkyl})O$— (e.g., methylenedioxy-), —$SR^b$, guanidine, guanidine wherein one or more of the guanidine hydrogens are replaced with a lower-alkyl group, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$SOR^a$, —$SO_2R^a$, —$SO_2NR^bR^c$, and —$NR^cSO_2R^a$, where $R^a$ is chosen from optionally substituted $C_1\text{-}C_6$ alkyl, optionally substituted cycloalkyl, optionally substituted aryl, optionally substituted heterocycloalkyl, and optionally substituted heteroaryl;

$R^b$ is chosen from H, optionally substituted $C_1\text{-}C_6$ alkyl, optionally substituted cycloalkyl, optionally substituted aryl, optionally substituted heterocycloalkyl, and optionally substituted heteroaryl; and $R^c$ is chosen from hydrogen and optionally substituted $C_1\text{-}C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1\text{-}C_4$ alkyl, cycloalkyl, aryl, heterocycloalkyl, heteroaryl, aryl-$C_1\text{-}C_4$ alkyl-, heteroaryl-$C_1\text{-}C_4$ alkyl-, $C_1\text{-}C_4$ haloalkyl-, —$OC_1\text{-}C_4$ alkyl, —$OC_1\text{-}C_4$ alkylphenyl, —$C_1\text{-}C_4$ alkyl-OH, —$C_1\text{-}C_4$ alkyl-O—$C_1\text{-}C_4$ alkyl, —$OC_1\text{-}C_4$ haloalkyl, halo, —OH, —$NH_2$, —$C_1\text{-}C_4$ alkyl-$NH_2$, —$N(C_1\text{-}C_4$ alkyl)($C_1\text{-}C_4$ alkyl), —$NH(C_1\text{-}C_4$ alkyl), —$N(C_1\text{-}C_4$ alkyl)($C_1\text{-}C_4$ alkylphenyl), —$NH(C_1\text{-}C_4$ alkylphenyl), cyano, nitro, oxo (as a substituent for heteroaryl), —$CO_2H$, —$C(O)OC_1\text{-}C_4$ alkyl, —$CON(C_1\text{-}C_4$ alkyl)($C_1\text{-}C_4$ alkyl), —$CONH(C_1\text{-}C_4$ alkyl), —$CONH_2$, —$NHC(O)(C_1\text{-}C_4$ alkyl), —$NHC(O)$(phenyl), —$N(C_1\text{-}C_4$ alkyl)$C(O)(C_1\text{-}C_4$ alkyl), —$N(C_1\text{-}C_4$ alkyl)$C(O)$(phenyl), —$C(O)C_1\text{-}C_4$ alkyl, —$C(O)C_1\text{-}C_4$ phenyl, —$C(O)C_1\text{-}C_4$ haloalkyl, —$OC(O)C_1\text{-}C_4$ alkyl, —$SO_2(C_1\text{-}C_4$ alkyl), —$SO_2$(phenyl), —$SO_2(C_1\text{-}C_4$ haloalkyl), —$SO_2NH_2$, —$SO_2NH(C_1\text{-}C_4$ alkyl), —$SO_2NH$(phenyl), —$NHSO_2(C_1\text{-}C_4$ alkyl), —$NHSO_2$(phenyl), and —$NHSO_2$ ($C_1\text{-}C_4$ haloalkyl).

The term "substituted alkoxy" refers to alkoxy wherein the alkyl constituent is substituted (i.e., —O-(substituted alkyl)) wherein "substituted alkyl" is as described herein. "Substituted alkoxy" also includes glycosides (i.e., glycosyl groups) and derivatives of ascorbic acid.

The term "substituted amino" refers to the group —$NHR^d$ or —$NR^dR^d$ where each $R^d$ is independently chosen from: hydroxy, optionally substituted alkyl, optionally substituted cycloalkyl, optionally substituted acyl, aminocarbonyl, optionally substituted aryl, optionally substituted heteroaryl, optionally substituted heterocycloalkyl, optionally substituted alkoxycarbonyl, sulfinyl and sulfonyl, each as described herein, and provided that only one $R^d$ may be hydroxyl. The term "substituted amino" also refers to N-oxides of the groups —$NHR^d$, and $NR^dR^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Aminocarbonyl" encompasses a group of the formula —(C=O) (optionally substituted amino) wherein substituted amino is as described herein.

"Acyl" refers to the groups (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula $CH_3(C=O)$—.

By "alkoxycarbonyl" is meant an ester group of the formula (alkoxy)(C=O)— attached through the carbonyl carbon wherein the alkoxy group has the indicated number of carbon atoms. Thus a $C_1\text{-}C_6$ alkoxycarbonyl group is an alkoxy group having from 1 to 6 carbon atoms attached through its oxygen to a carbonyl linker.

By "amino" is meant the group —$NH_2$.

The term "sulfinyl" includes the groups: —S(O)-(optionally substituted ($C_1\text{-}C_6$)alkyl), —S(O)-optionally substituted aryl), —S(O)-optionally substituted heteroaryl), —S(O)-(optionally substituted heterocycloalkyl); and —S(O)-(optionally substituted amino).

The term "sulfonyl" includes the groups —$S(O_2)$-(optionally substituted ($C_1\text{-}C_6$)alkyl), —$S(O_2)$-optionally substituted aryl), —$S(O_2)$-optionally substituted heteroaryl), —$S(O_2)$-(optionally substituted heterocycloalkyl), —$S(O_2)$-(optionally substituted alkoxy), —$S(O_2)$-optionally substituted aryloxy), —$S(O_2)$-optionally substituted heteroaryloxy), —$S(O_2)$-(optionally substituted heterocyclyloxy); and —$S(O_2)$-(optionally substituted amino).

The term "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl are as described herein.

The term "substituted alkoxycarbonyl" refers to the group (substituted alkyl)-O—C(O)— wherein the group is attached to the parent structure through the carbonyl functionality and wherein substituted alkyl is as described herein.

"Glycosides" refer to any of a number of sugar derivatives that contain a non-sugar group bonded to an oxygen or nitrogen atom of a sugar and that on hydrolysis yield that sugar. An example of a glycosyl group is glucosyl.

"Derivatives of ascorbic acid" or "ascorbic acid derivatives" refer to any of a number of derivatives that contain a non-sugar group bonded to an oxygen or nitrogen atom of ascorbic acid and that on hydrolysis yield ascorbic acid (i.e., (R)-5-((S)-1,2-dihydroxyethyl)-3,4-dihydroxyfuran-2(5H)-one).

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, such compounds include Z- and E-forms (or cis- and trans-forms) of compounds with carbon-carbon double bonds. Where compounds described herein exist in various tautomeric forms, the term "compound" is intended to include all tautomeric forms of the compound. Such compounds also include crystal forms including polymorphs and clathrates. Similarly, the term "salt" is intended to include all tautomeric forms and crystal forms of the compound.

Chemical entities include, but are not limited to compounds described herein and all pharmaceutically acceptable forms thereof. Pharmaceutically acceptable forms of the compounds recited herein include pharmaceutically acceptable salts, prodrugs, and mixtures thereof. In some embodiments, the compounds described herein are in the form of pharmaceutically acceptable salts and prodrugs. Hence, the terms "chemical entity" and "chemical entities" also encompass pharmaceutically acceptable salts, prodrugs, and mixtures thereof.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—$(CH_2)_n$—COOH where n is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of chemical entities described herein. In some embodiments, the "prodrugs" described herein include any compound that becomes a compound of Formula I when administered to a patient, e.g., upon metabolic processing of the prodrug. Examples of prodrugs include derivatives of functional groups, such as a carboxylic acid group, in the compounds of Formula I. Exemplary prodrugs of a carboxylic acid group include, but are not limited to, carboxylic acid esters such as alkyl esters, hydroxyalkyl esters, arylalkyl esters, and aryloxyalkyl esters. Other exemplary prodrugs include lower alkyl esters such as ethyl ester, acyloxyalkyl esters such as pivaloyloxymethyl (POM), glycosides, and ascorbic acid derivatives.

Other exemplary prodrugs include amides of carboxylic acids. Exemplary amide prodrugs include metabolically labile amides that are formed, for example, with an amine and a carboxylic acid. Exemplary amines include $NH_2$, primary, and secondary amines such as $NHR^x$, and $NR^xR^y$, wherein $R^x$ is hydrogen, $(C_1-C_{18})$-alkyl, $(C_3-C_7)$-cycloalkyl, $(C_3-C_7)$-cycloalkyl-$(C_1-C_4)$-alkyl-, $(C_6-C_{14})$-aryl which is unsubstituted or substituted by a residue $(C_1-C_2)$-alkyl, $(C_1-C_2)$-alkoxy, fluoro, or chloro; heteroaryl-, $(C_6-C_{14})$-aryl-$(C_1-C_4)$-alkyl- where aryl is unsubstituted or substituted by a residue $(C_1-C_2)$-alkyl, $(C_1-C_2)$-alkoxy, fluoro, or chloro; or heteroaryl-$(C_1-C_4)$-alkyl- and in which $R^y$ has the meanings indicated for $R^x$ with the exception of hydrogen or wherein $R^x$ and $R^y$, together with the nitrogen to which they are bound, form an optionally substituted 4- to 7-membered heterocycloalkyl ring which optionally includes one or two additional heteroatoms chosen from nitrogen, oxygen, and sulfur. A discussion of prodrugs is provided in T. Higuchi and V. Stella, Pro-drugs as Novel Delivery Systems, Vol. 14 of the A.C.S. Symposium Series, in Edward B. Roche, ed., Bioreversible Carriers in Drug Design, American Pharmaceutical Association and Pergamon Press, 1987, and in Design of Prodrugs, ed. H. Bundgaard, Elsevier, 1985.

A "solvate" is formed by the interaction of a solvent and a compound. The term "compound" is intended to include solvates of compounds. Similarly, "salts" includes solvates of salts. Suitable solvates are pharmaceutically acceptable solvates, such as hydrates, including monohydrates and hemi-hydrates.

A "chelate" is formed by the coordination of a compound to a metal ion at two (or more) points. The term "compound" is intended to include chelates of compounds. Similarly, "salts" includes chelates of salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound'.

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry (G. C. Pimentel and A. L. McClellan, The Hydrogen Bond, Freeman, San Francisco, 1960; R. Taylor and O. Kennard, "Hydrogen Bond Geometry in Organic Crystals", Accounts of Chemical Research, 17, pp. 320-326 (1984)).

"Hydrogen bond acceptor" refers to a group comprising an oxygen or nitrogen, such as an oxygen or nitrogen that is $sp^2$-hybridized, an ether oxygen, or the oxygen of a sulfoxide or N-oxide.

The term "hydrogen bond donor" refers to an oxygen, nitrogen, or heteroaromatic carbon that bears a hydrogen-.group containing a ring nitrogen or a heteroaryl group containing a ring nitrogen.

As used herein the terms "group", "radical" or "fragment" are synonymous and are intended to indicate functional groups or fragments of molecules attachable to a bond or other fragments of molecules.

The term "active agent" is used to indicate a chemical entity which has biological activity. In some embodiments, an "active agent" is a compound having pharmaceutical utility. For example an active agent may be an anti-neurodegenerative therapeutic.

The term "therapeutically effective amount" of a chemical entity described herein means an amount effective, when administered to a human or non-human subject, to provide a therapeutic benefit such as amelioration of symptoms, slowing of disease progression, or prevention of disease e.g., a therapeutically effective amount may be an amount sufficient to decrease the symptoms of a disease responsive to inhibition of KMO activity and modulation of kynurenine pathway metabolites (such as kynurenine, kynurenic acid, anthranilic acid, 3-OH-kynurenine, 3-OH anthranilic acid, or quinolinic acid). In some embodiments, a therapeutically effective amount is an amount sufficient to treat the symptoms of neurodegenerative pathway or disease. In some embodiments a therapeutically effective amount is an amount sufficient to reduce the signs or side effects of a neurodegenerative disease. In some embodiments, a therapeutically effective amount of a chemical entity is an amount sufficient to prevent a significant increase or significantly reduce the level of neuronal cell death. In some embodiments, a therapeutically effective amount of a chemical entity is an amount sufficient to prevent a significant increase or significantly reduce the level of QUIN associated with neuronal cell death. In some embodiments, a therapeutically effective amount of a chemical entity is an amount sufficient to effect an increase in the level of KYNA associated with neuronal cell health. In some embodiments, a therapeutically effective amount of a chemical entity is an amount sufficient to increase the anticonvulsant and neuroprotective properties associated with lowered levels of QUIN and increased levels of KYNA. In some embodiments, a therapeutically effective amount is an amount sufficient to modulate an inflammatory process in the body, including but not limited to inflammation in the brain, spinal cord, and peripheral nervous system, or meninges. In some embodiments, a therapeutically effective amount is an amount sufficient to modulate the production of cytokines responsible for mounting an effective immune response (such as IL-1 beta or TNF-alpha) or an amount sufficient to affect monocyte/macrophage pro-inflammatory activity in the periphery or in the brain in conditions where the blood-brain barrier is compromised, such as in multiple sclerosis).

In methods described herein for treating a neurodegenerative disorder, a therapeutically effective amount may also be an amount sufficient, when administered to a patient, to detectably slow the progression of the neurodegenerative disease, or prevent the patient to whom the chemical entity is given from presenting symptoms of the neurodegenerative disease. In some methods described herein for treating a neurodegenerative disease, a therapeutically effective amount may also be an amount sufficient to produce a detectable decrease in the level of neuronal cell death. For example, in some embodiments a therapeutically effective amount is an amount of a chemical entity described herein sufficient to significantly decrease the level of neuronal death by effecting a detectable decrease in the amount of QUIN, and an increase in the amount of kynurenine, KYNA, or anthranilic acid.

In addition, an amount is considered to be a therapeutically effective amount if it is characterized as such by at least one of the above criteria or experimental conditions, regardless of any inconsistent or contradictory results under a different set of criteria or experimental conditions.

The term "inhibition" indicates a significant decrease in the baseline activity of a biological activity or process. "Inhibition of KMO activity" refers to a decrease in KMO activity as a direct or indirect response to the presence of at least one chemical entity described herein, relative to the activity of KMO in the absence of at least one chemical entity. The decrease in activity may be due to the direct interaction of the compound with KMO, or due to the interaction of the chemical entity(ies) described herein with one or more other factors that in turn affect KMO activity.

For example, the presence of the chemical entity(ies) may decrease KMO activity by directly binding to the KMO, by causing (directly or indirectly) another factor to decrease KMO activity, or by (directly or indirectly) decreasing the amount of KMO present in the cell or organism.

"Inhibition of KMO activity" refers to a decrease in KMO activity as a direct or indirect response to the presence of at least one chemical entity described herein, relative to the activity of KMO in the absence of the at least one chemical entity. The decrease in activity may be due to the direct interaction of the compound with KMO or with one or more other factors that in turn affect KMO activity.

Inhibition of KMO activity also refers to an observable inhibition of 3-HK and QUIN production in a standard assay such as the assay described below. The inhibition of KMO activity also refers to an observable increase in the production of KYNA. In some embodiments, the chemical entity described herein has an $IC_{50}$ value less than or equal to 1 micromolar. In some embodiments, the chemical entity has an $IC_{50}$ value less than or equal to less than 100 micromolar. In some embodiments, the chemical entity has an $IC_{50}$ value less than or equal to 10 nanomolar.

"KMO activity" also includes activation, redistribution, reorganization, or capping of one or more various KMO membrane-associated proteins (such as those receptors found in the mitochondria), or binding sites can undergo redistribution and capping that can initiate signal transduction. KMO activity also can modulate the availability of kynurenine, which can effect the synthesis or production of QUIN, KYNA, anthranilic acid, and/or 3-HK.

A "disease responsive to inhibition of KMO activity" is a disease in which inhibiting KMO provides a therapeutic benefit such as an amelioration of symptoms, decrease in disease progression, prevention or delay of disease onset, prevention or amelioration of an inflammatory response, or inhibition of aberrant activity and/or death of certain cell-types (such as neuronal cells).

"Treatment" or "treating" means any treatment of a disease in a patient, including:
a) preventing the disease, that is, causing the clinical symptoms of the disease not to develop;
b) inhibiting the progression of the disease;
c) slowing or arresting the development of clinical symptoms; and/or
d) relieving the disease, that is, causing the regression of clinical symptoms.

"Subject" or "patient' refers to an animal, such as a mammal, that has been or will be the object of treatment, observation or experiment. The methods described herein may be useful in both human therapy and veterinary applications. In some embodiments, the subject is a mammal; and in some embodiments the subject is human.

Provided is at least one chemical entity chosen from compounds of Formula I

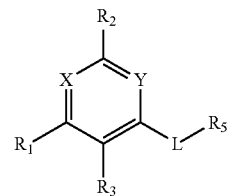

Formula I and pharmaceutically acceptable salts and prodrugs thereof wherein:
X and Y are independently chosen from —N— and —CH—, provided that at least one of X and Y is —N—;

$R_1$ is aryl or monocyclic heteroaryl, each of which is substituted with
a first group of the formula —Z—$R_6$ wherein
Z is chosen from —O—, —S—, —S(O)—, —S(O)$_2$—, —CR$_{11}$R$_{12}$—, —OCR$_{11}$R$_{12}$—, —NR$_{13}$—, —NR$_{13}$CR$_{11}$R$_{12}$—, —CR$_{11}$R$_{12}$NR$_{13}$—, and —C(O)— where $R_{11}$, $R_{12}$, and $R_{13}$ are independently chosen from hydrogen, lower alkyl, hydroxyl, and lower alkoxy,
$R_6$ is chosen from hydrogen, optionally substituted $C_1$-$C_6$ alkyl, optionally substituted cycloalkyl, optionally substituted aryl, optionally substituted heteroaryl, and optionally substituted heterocycloalkyl, provided that if Z is —O—, then $R_6$ is not optionally substituted benzyl or optionally substituted pyridylmethyl, or
$R_6$ and $R_{13}$, taken together with the nitrogen to which they are bound form an optionally substituted 5- to 7-membered heterocycloalkyl ring, and
a second group chosen from halo and lower alkyl optionally substituted with halo, or
$R_1$ is chosen from 2,3-dihydrobenzofuran-5-yl, chroman-6-yl, 1,3-benzodioxol-5-yl, 2,3-dihydro-1,4-benzodioxin-6-yl, 1,3-benzoxazol-5-yl, 1,3-benzoxazol-6-yl, 2-oxo-2,3-dihydro-1,3-benzoxazol-5-yl, benzothiophen-5-yl, benzothiazol-5-yl, benzoimidazol-5-yl, benzofuran-5-yl, 1H-indol-5-yl, 1H-indazol-5-yl, isoindolin-5-yl, benzo[c][1,2,5]oxadiazol-5-yl, 1,2,3,4-tetrahydroquinolin-6-yl, imidazo[1,2-a]pyridin-6-yl, pyrazolo[1,5-a]pyridine-5-yl, quinolin-6-yl, quinazolin-6-yl, quinazolin-7-yl, and quinoxalin-6-yl, each of which is optionally substituted,
or
$R_1$ and $R_3$, taken together with intervening atoms form a bicyclic ring of the formula

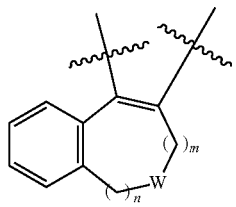

which is optionally substituted where m is 0 or 1 and n is 0 or 1, provided that at least one of m and n is 1 and W is —O—, or —N($R_8$)— where $R_8$ is hydrogen or lower alkyl;
$R_2$ is chosen from hydrogen and optionally substituted lower alkyl;
$R_3$ is chosen from hydrogen, halo, optionally substituted lower alkyl, hydroxyl, optionally substituted lower alkoxy, and optionally substituted amino;
L is chosen from —C(O)—, —C(O)O—, —C(O)N(R$_4$)—, —C(O)N(OR$_7$)—, —N(R$_4$)S(O)$_2$—, —S(O)$_2$N(R$_4$)—, and —C(O)N(R$_4$)—S(O)$_2$—;
$R_4$ is chosen from hydrogen and lower alkyl;
$R_5$ is chosen from hydrogen, optionally substituted lower alkyl, optionally substituted aryl, optionally substituted heteroaryl, optionally substituted cycloalkyl, and optionally substituted heterocycloalkyl; provided that when L is —N(R$_4$)S(O)$_2$—, then $R_5$ is not hydrogen, or
$R_4$ and $R_5$ taken together with the nitrogen to which they are bound form an optionally substituted 4- to 7-membered heterocycloalkyl ring, which is optionally fused to an optionally substituted cycloalkyl, optionally substituted heterocycloalkyl, optionally substituted aryl or optionally substituted heteroaryl ring; or
$R_3$ and $R_5$, taken together with the intervening atoms, form an optionally substituted 5- to 7-membered ring; and
$R_7$ is chosen from hydrogen and lower alkyl;
provided that the compound of Formula I is not chosen from
6-(3-chloro-4-methyl-phenyl)-pyrimidine-4-carboxylic acid methyl ester;
6-(3-chloro-4-methyl-phenyl)-pyrimidine-4-carboxylic acid;
6-(3-chloro-4-methoxy-phenyl)-pyrimidine-4-carboxylic acid methyl ester; and
6-(3-chloro-4-methoxy-phenyl)-pyrimidine-4-carboxylic acid.

In some embodiments, $R_1$ is phenyl substituted with
a first group of the formula —Z—$R_6$ wherein Z is chosen from —O—, —S—, —S(O)—, —S(O)$_2$—, and —CR$_{11}$R$_{12}$—; and $R_6$ is chosen from hydrogen, optionally substituted $C_1$-$C_6$ alkyl, optionally substituted cycloalkyl, and optionally substituted heterocycloalkyl, and
a second group chosen from halo and lower alkyl optionally substituted with halo.

In some embodiments, $R_1$ is pyridinyl substituted with
a first group of the formula —Z—$R_6$ wherein Z is chosen from —O—, —S—, —S(O)—, —S(O)$_2$—, and —CR$_{11}$R$_{12}$—; and $R_6$ is chosen from hydrogen, optionally substituted $C_1$-$C_6$ alkyl, optionally substituted cycloalkyl, and optionally substituted heterocycloalkyl, and
a second group chosen from halo and lower alkyl optionally substituted with halo.

In some embodiments, Z is —O—.
In some embodiments, Z is —S—.
In some embodiments, Z is —S(O)$_2$—.
In some embodiments, Z is —CR$_{11}$R$_{12}$—.
In some embodiments, $R_6$ is chosen from hydrogen, methyl, difluoromethyl, trifluoromethyl, ethyl, 2,2,2-trifluoro-1-methyl-ethyl, isopropyl, (S)-sec-butyl, (R)-sec-butyl, cyclopropyl, cyclobutyl, cyclopentyl, 2-morpholin-4-yl-ethyl, 2-piperidin-1-yl-ethyl, pyrrolidin-3-yl, and tetrahydro-furan-3-yl.

In some embodiments, $R_1$ is chosen from 3-chloro-4-cyclobutoxy-phenyl, 3-chloro-4-cyclopentyloxy-phenyl, 3-chloro-4-cyclopropoxy-phenyl, 3-chloro-4-isopropoxy-phenyl, 3-chloro-4-methoxy-phenyl, [4-chloro-3-(2-morpholin-4-yl-ethoxy)-phenyl, 3-chloro-4-(2-piperidin-1-yl-ethoxy)-phenyl, 3-chloro-4-(pyrrolidin-3-yloxy)-phenyl, 4-(S)-sec-butoxy-3-chloro-phenyl, 4-(R)-sec-butoxy-3-chloro-phenyl, 4-chloro-3-(tetrahydro-furan-3-yloxy)-phenyl, 3-chloro-4-trifluoromethoxy-phenyl, 3-chloro-4-(2,2,2-trifluoro-1-methyl-ethoxy, 3-methoxy-phenyl, 4-methoxy-phenyl, 3,4-dimethoxyphenyl, 3-chloro-4-isopropylphenyl, 3-fluoro-4-methylphenyl, and 3-fluoro-4-isopropylphenyl, 3,4-bis(methylsulfanyl)phenyl, 3,4-bis(methylsulfonyl)phenyl, 3,4-bis(trifluoromethoxy)phenyl, 3-chloro-4-(difluoromethoxy)phenyl, 3-chloro-4-(methylsulfanyl)phenyl, 3-chloro-4-(methylsulfonyl)phenyl, 3-chloro-4-(trifluoromethoxy)phenyl, 3-chloro-4-(cyclopropoxymethyl)phenyl, 3-chloro-4-(cyclopropylmethyl)phenyl, 3-chloro-4-(cyclopropanesulfinyl)phenyl, 3-chloro-4-(cyclopropanesulfonyl)phenyl, 3-chloro-4-[cyclopropyl(hydroxy)methyl]phenyl, 3-chloro-4-(1-cyclopropoxyethyl)phenyl, 3-chloro-4-cyclopropanecarbonylphenyl, 3-chloro-4-cyclopropylphenyl, 4-(aziridin-1-ylmethyl)-3-chlorophenyl, 3-chloro-4-[(dimethylamino)methyl]phenyl, 3-chloro-4-(cyclopropylamino)phenyl, 3-chloro-4-[cyclopropyl(methyl)amino]phenyl, 3-chloro-4-[(cyclopropylamino)methyl]phenyl, 3-chloro-4-{[cyclopropyl(methyl)amino]methyl}phenyl, 3-chloro-4-(1-methoxycyclopropyl)phenyl, 4-chloro-3-[(1,1,1-trifluoropropan-2-yl)oxy]phenyl, 4-chloro-3-(trifluoromethoxy)phenyl, 4-chloro-3-(2-methylpropoxy)phenyl, 4-chloro-3-(propan-2-yloxy)phenyl, 4-chloro-3-(propan-2-yloxy)phenyl, 4-chloro-3-methoxyphenyl, 4-chloro-3-cyclopropoxyphenyl, and 3-chloro-4-{[1-(morpholin-4-yl)propan-2-yl]oxy}phenyl.

In some embodiments, $R_1$ is chosen from 3-chloro-4-methoxy-phenyl, 3-chloro-4-(trifluoromethoxy)phenyl, 3-chloro-4-cyclobutoxy-phenyl, 3-chloro-4-cyclopropoxyphenyl, 3-chloro-4-isopropoxy-phenyl, 3-chloro-4-methoxy-phenyl, 3-chloro-4-(pyrrolidin-3-yloxy)-phenyl, 4-(S)-sec-butoxy-3-chloro-phenyl, 4-(R)-sec-butoxy-3-chloro-phenyl, 4-chloro-3-(tetrahydro-furan-3-yloxy)-phenyl, 3-chloro-4-trifluoromethoxy-phenyl, 3-chloro-4-(2,2,2-trifluoro-1-methyl-ethoxy, 3-methoxy-phenyl, 4-methoxyphenyl, 3,4-dimethoxyphenyl, 3-chloro-4-isopropylphenyl, 3-fluoro-4-methylphenyl, and 3-fluoro-4-isopropylphenyl, 3,4-bis(trifluoromethoxy)phenyl, 3-chloro-4-(difluoromethoxy)phenyl, 3-chloro-4-(trifluoromethoxy)phenyl, 3-chloro-4-(cyclopropoxymethyl)phenyl, 3-chloro-4-(cyclopropylmethyl)phenyl, 3-chloro-4-(cyclopropanesulfinyl)phenyl, 3-chloro-4-(cyclopropanesulfonyl)phenyl, 3-chloro-4-[cyclopropyl(hydroxy)methyl]phenyl, 3-chloro-4-(1-cyclopropoxyethyl)phenyl, 3-chloro-4-cyclopropanecarbonylphenyl, 3-chloro-4-cyclopropylphenyl, 4-(aziridin-1-ylmethyl)-3-chlorophenyl, 3-chloro-4-[(dimethylamino)methyl]phenyl, 3-chloro-4-(cyclopropylamino)phenyl, 3-chloro-4-[cyclopropyl(methyl)amino]phenyl, 3-chloro-4-[(cyclopropylamino)methyl]phenyl, 3-chloro-4-{[cyclopropyl(methyl)amino]methyl}phenyl, 3-chloro-4-(1-methoxycyclopropyl)phenyl, 4-chloro-3-[(1,1,1-trifluoropropan-2-yl)oxy]phenyl, 4-chloro-3-(trifluoromethoxy)phenyl, 4-chloro-3-(2-methylpropoxy)phenyl, 4-chloro-3-(propan-2-yloxy)phenyl, 4-chloro-3-(propan-2-yloxy)phenyl, 4-chloro-3-methoxyphenyl, and 4-chloro-3-cyclopropoxyphenyl.

In some embodiments, $R_1$ is chosen from 1,3-benzodioxol-5-yl, chroman-6-yl, 2,3-dihydrobenzofuran-5-yl, benzofuran-5-yl, 2,3-dihydro-1H-isoindol-5-yl, 1,3-benzoxazol-5-yl, 2-oxo-2,3-dihydro-1,3-benzoxazol-5-yl, 1,3-benzoxazol-5-yl, imidazo[1,2-a]pyridin-6-yl, 1,3-benzoxazol-6-yl, quinolin-6-yl, and pyrazolo[1,5-a]pyridin-5-yl, each of which is optionally substituted with one or two groups chosen from halo, lower alkyl optionally substituted with halo, cycloalkyl, and lower alkoxy optionally substituted with halo.

In some embodiments, $R_1$ is chosen from 1,3-benzodioxol-5-yl, 2,2-difluoro-1,3-benzodioxol-5-yl, 8-chloro-chroman-6-yl, 7-chloro-benzofuran-5-yl, 7-chloro-2-cyclopropyl-2,3-dihydro-1H-isoindol-5-yl, 7-chloro-2-methyl-1,3-benzoxazol-5-yl, 7-chloro-2-oxo-2,3-dihydro-1,3-benzoxazol-5-yl, 7-chloro-3-methyl-2-oxo-2,3-dihydro-1,3-benzoxazol-5-yl, 7-chloro-2-cyclopropyl-1,3-benzoxazol-5-yl, 8-chloroimidazo[1,2-a]pyridin-6-yl, 4-chloro-1,3-benzoxazol-6-yl, quinolin-6-yl, and pyrazolo[1,5-a]pyridin-5-yl.

In some embodiments, $R_1$ is chosen from 1,3-benzodioxol-5-yl, 2,2-difluoro-1,3-benzodioxol-5-yl, 8-chloro-chroman-6-yl, 7-chloro-benzofuran-5-yl, 7-chloro-2-methyl-1,3-benzoxazol-5-yl, 7-chloro-2-cyclopropyl-1,3-benzoxazol-5-yl, 8-chloroimidazo[1,2-a]pyridin-6-yl, 4-chloro-1,3-benzoxazol-6-yl, quinolin-6-yl, and pyrazolo[1,5-a]pyridin-5-yl.

In some embodiments, $R_2$ is hydrogen.
In some embodiments, $R_2$ is lower alkyl.
In some embodiments, $R_2$ is methyl or ethyl.
In some embodiments, $R_2$ is methyl.
In some embodiments, $R_3$ is hydrogen.
In some embodiments, $R_3$ is fluoro or chloro.
In some embodiments, $R_3$ is methyl.
In some embodiments, $R_3$ is —$CH_2OH$.
In some embodiments, X is —N—.
In some embodiments, Y is —N—.
In some embodiments, X and Y are —N—.
In some embodiments, L is —C(O)O—.
In some embodiments, L is —C(O)N($R_4$)—.
In some embodiments, L is —N($R_4$)S(O)$_2$—.
In some embodiments, $R_4$ is hydrogen.
In some embodiments, $R_5$ is lower alkyl.
In some embodiments, $R_5$ is hydrogen.

In some embodiments, $R_4$ and $R_5$ taken together with the nitrogen to which they are bound form an optionally substituted 5- to 7-membered heterocycloalkyl ring. In some embodiments, $R_4$ and $R_5$ taken together with the nitrogen to which they are bound form a ring chosen from 3-oxopiperazin-1-yl, 5,6-dihydro-[1,2,4]triazolo[4,3-a]pyrazin-7(8H)-yl, 4-oxohexahydropyrrolo[3,4-c]pyrrol-2(1H)-yl, piperidin-1-yl, azetidin-3-yl, 5-oxo-1,4-diazepan-1-yl, 1,4-diazepan-1-yl, 5,6-dihydroimidazo[1,2-a]pyrazin-7(8H)-yl, 3-oxo-3,4-dihydroquinoxalin-1(2H)-yl, 7,8-dihydro-1,6-naphthyridin-6(5H)-yl, 4-oxohexahydropyrrolo[1,2-a]pyrazin-2(1H)-yl, 4-oxodihydro-1H-pyrido[1,2-a]pyrazin-2(6H,7H,8H,9H,9aH)-yl, pyrrolidin-1-yl, 1,1-dioxido-1,2,5-thiadiazinan-5-yl, 5,7-dihydro-6H-pyrrolo[3,4-d]pyrimidin-6-yl, 5,7-dihydro-6H-pyrrolo[3,4-b]pyridin-6-yl, and 2,4,5,7-tetrahydro-6H-pyrazolo[3,4-c]pyridin-6-yl, each of which is optionally substituted. In some embodiments, the optional substituents are one or two groups independently chosen from halo, lower alkyl optionally substituted with halo, cycloalkyl, and lower alkoxy optionally substituted with halo.

Also provided is at least one chemical entity chosen from compounds of Formula II

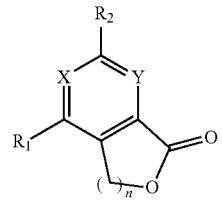

Formula II and pharmaceutically acceptable salts and prodrugs thereof, wherein n is chosen from 1 and 2 and wherein $R_1$, $R_2$, X, and Y are as described for compounds of Formula I.

In some embodiments, n is 1. In some embodiments, n is 2.

Also provided is a compound chosen from
6-(4-Chloro-3-methoxy-phenyl)-pyrimidine-4-carboxylic acid,
6-(3-Amino-4-chloro-phenyl)-pyrimidine-4-carboxylic acid,
6-[4-Chloro-3-(tetrahydro-furan-3-yloxy)-phenyl]-pyrimidine-4-carboxylic acid,
6-[4-Chloro-3-(tetrahydro-furan-3-yloxy)-phenyl]-pyrimidine-4-carboxylic acid pyridin-3-ylamide,
6-[4-Chloro-3-(2-morpholin-4-yl-ethoxy)-phenyl]-pyrimidine-4-carboxylic acid pyridin-3-yl-amide,
6-(3-Chloro-4-isopropyl-phenyl)-pyrimidine-4-carboxylic acid,
6-(3-Fluoro-4-methyl-phenyl)-pyrimidine-4-carboxylic acid,
6-(3-Chloro-4-isopropoxy-phenyl)-pyrimidine-4-carboxylic acid,
6-(3-Chloro-4-isopropoxy-phenyl)-2-methyl-pyrimidine-4-carboxylic acid,
6-(3-Fluoro-4-methyl-phenyl)-2-methyl-pyrimidine-4-carboxylic acid,
6-(3-Chloro-4-cyclopentyloxy-phenyl)-pyrimidine-4-carboxylic acid,
6-(3-Chloro-4-trifluoromethoxy-phenyl)-pyrimidine-4-carboxylic acid,
6-(3-Fluoro-4-isopropyl-phenyl)-pyrimidine-4-carboxylic acid,
6-(4-(R)-sec-Butoxy-3-chloro-phenyl)-pyrimidine-4-carboxylic acid,
6-(4-(S)-sec-Butoxy-3-chloro-phenyl)-pyrimidine-4-carboxylic acid,
6-(3-Chloro-4-cyclopropoxy-phenyl)-pyrimidine-4-carboxylic acid,
6-[3-Chloro-4-(2,2,2-trifluoro-1-methyl-ethoxy)-phenyl]-pyrimidine-4-carboxylic acid,
4-(3-Chloro-4-cyclopropoxy-phenyl)-pyridine-2-carboxylic acid,
6-(4-(R)-sec-Butoxy-3-chloro-phenyl)-pyridine-4-carboxylic acid,
6-(4-(S)-sec-Butoxy-3-chloro-phenyl)-pyridine-4-carboxylic acid,
4-(3-Chloro-4-isopropoxy-phenyl)-pyridine-2-carboxylic acid,
4-(3-Chloro-4-trifluoromethoxy-phenyl)-pyridine-2-carboxylic acid,
6-(3-Chloro-4-cyclobutoxy-phenyl)-pyrimidine-4-carboxylic acid,
6-[3-Chloro-4-(2-piperidin-1-yl-ethoxy)-phenyl]-pyrimidine-4-carboxylic acid,
6-Quinolin-6-yl-pyrimidine-4-carboxylic acid,
6-(8-Chloro-chroman-6-yl)-pyrimidine-4-carboxylic acid,
6-(7-Chloro-benzofuran-5-yl)-pyrimidine-4-carboxylic acid,
6-[3-Chloro-4-(pyrrolidin-3-yloxy)-phenyl]-pyrimidine-4-carboxylic acid,
6-(8-chloro-1-methyl-1,2,3,4-tetrahydroquinolin-6-yl)pyrimidine-4-carboxylic acid,
6-(8-chloroquinolin-6-yl)pyrimidine-4-carboxylate,
N-[6-(3-chloro-4-cyclopropoxyphenyl)pyrimidin-4-yl]benzenesulfonamide,
N-[6-(3-chloro-4-cyclopropoxyphenyl)pyrimidin-4-yl]-4-fluorobenzene-1-sulfonamide,
N-[6-(3-chloro-4-cyclopropoxyphenyl)pyrimidin-4-yl]-4-(trifluoromethoxy)benzene-1-sulfonamide,
N-[6-(3-chloro-4-cyclopropoxyphenyl)pyrimidin-4-yl]-3-(trifluoromethoxy)benzene-1-sulfonamide,
N-[6-(3-chloro-4-cyclopropoxyphenyl)pyrimidin-4-yl]-2-fluorobenzene-1-sulfonamide,
N-[6-(3-chloro-4-cyclopropoxyphenyl)pyrimidin-4-yl]cyclopropanesulfonamide,
6-(8-chloro-1,2,3,4-tetrahydroquinolin-6-yl)pyrimidine-4-carboxylate,
6-(3-chloro-4-cyclopropoxyphenyl)-5-methylpyrimidine-4-carboxylate,
6-{3-chloro-4-[2-(morpholin-4-yl)ethoxy]phenyl}pyrimidine-4-carboxylate,
6-[3-chloro-4-(cyclopropylmethoxy)phenyl]pyrimidine-4-carboxylate,
6-[3-chloro-4-(oxetan-3-yloxy)phenyl]pyrimidine-4-carboxylate,
4-(3-chloro-4-cyclopropoxyphenyl)-5H,7H-furo[3,4-d]pyrimidin-7-one,
6-(3-chloro-4-cyclopropoxyphenyl)-5-(hydroxymethyl)pyrimidine-4-carboxylic acid,
4-(3-chloro-4-cyclopropoxyphenyl)-5H,6H,8H-pyrano[3,4-d]pyrimidin-8-one,
[(2R,3S,4S,5R)-3,4,5,6-tetrahydroxyoxan-2-yl]methyl 6-(3-chloro-4-cyclopropoxyphenyl)pyrimidine-4-carboxylate,
6-(3-chloro-4-{[1-(morpholin-4-yl)propan-2-yl]oxy}phenyl)pyrimidine-4-carboxylic acid,
6-[3-chloro-4-(cyclopropoxymethyl)phenyl]pyrimidine-4-carboxylic acid,
6-[3-chloro-4-(cyclopropylmethyl)phenyl]pyrimidine-4-carboxylic acid,
6-[3-chloro-4-(cyclopropylsulfanyl)phenyl]pyrimidine-4-carboxylic acid,
6-[3-chloro-4-(cyclopropanesulfinyl)phenyl]pyrimidine-4-carboxylic acid,
6-[3-chloro-4-(cyclopropanesulfonyl)phenyl]pyrimidine-4-carboxylic acid,
6-{3-chloro-4-[cyclopropyl(hydroxy)methyl]phenyl}pyrimidine-4-carboxylic acid,
6-[3-chloro-4-(1-cyclopropoxyethyl)phenyl]pyrimidine-4-carboxylic acid,
6-(3-chloro-4-cyclopropanecarbonylphenyl)pyrimidine-4-carboxylic acid,
6-(3-chloro-4-cyclopropylphenyl)pyrimidine-4-carboxylic acid,
6-[4-(aziridin-1-ylmethyl)-3-chlorophenyl]pyrimidine-4-carboxylic acid,
6-{3-chloro-4-[(dimethylamino)methyl]phenyl}pyrimidine-4-carboxylic acid
6-[3-chloro-4-(cyclopropylamino)phenyl]pyrimidine-4-carboxylic acid,
6-{3-chloro-4-[cyclopropyl(methyl)amino]phenyl}pyrimidine-4-carboxylic acid,
6-{3-chloro-4-[(cyclopropylamino)methyl]phenyl}pyrimidine-4-carboxylic acid,
6-(3-chloro-4-{[cyclopropyl(methyl)amino]methyl}phenyl)pyrimidine-4-carboxylic acid,
6-(7-chloro-2-cyclopropyl-2,3-dihydro-1H-isoindol-5-yl)pyrimidine-4-carboxylic acid,
6-[3-chloro-4-(furan-2-yl)phenyl]pyrimidine-4-carboxylic acid,
6-[3-chloro-4-(1-methoxycyclopropyl)phenyl]pyrimidine-4-carboxylic acid,
6-(2,3-dihydro-1,4-benzodioxin-6-yl)pyrimidine-4-carboxylic acid,
6-(7-chloro-2-methyl-1,3-benzoxazol-5-yl)pyrimidine-4-carboxylic acid, 6-(7-chloro-2-oxo-2,3-dihydro-1,3-benzoxazol-5-yl)pyrimidine-4-carboxylic acid,
6-(7-chloro-3-methyl-2-oxo-2,3-dihydro-1,3-benzoxazol-5-yl)pyrimidine-4-carboxylic acid,
6-(7-chloro-2-cyclopropyl-1,3-benzoxazol-5-yl)pyrimidine-4-carboxylic acid,
6-{8-chloroimidazo[1,2-a]pyridin-6-yl}pyrimidine-4-carboxylic acid,
6-(4-chloro-1,3-benzoxazol-6-yl)pyrimidine-4-carboxylic acid,
6-(quinolin-6-yl)pyrimidine-4-carboxylic acid,
6-{pyrazolo[1,5-a]pyridin-5-yl}pyrimidine-4-carboxylic acid,
6-(4-chloro-3-cyclopropoxyphenyl)pyrimidine-4-carboxylic acid,
6-(4-chloro-3-methoxyphenyl)pyrimidine-4-carboxylic acid,
6-[4-chloro-3-(propan-2-yloxy)phenyl]pyrimidine-4-carboxylic acid,
6-[4-chloro-3-(2-methylpropoxy)phenyl]pyrimidine-4-carboxylic acid,
6-[4-chloro-3-(trifluoromethoxy)phenyl]pyrimidine-4-carboxylic acid,
6-{4-chloro-3-[(1,1,1-trifluoropropan-2-yl)oxy]phenyl}pyrimidine-4-carboxylic acid,
6-(benzo[d][1,3]dioxol-5-yl)pyrimidine-4-carboxylic acid,
6-(2,2-difluorobenzo[d][1,3]dioxol-5-yl)pyrimidine-4-carboxylic acid,
6-(2,3-dihydrobenzo[b][1,4]dioxin-6-yl)pyrimidine-4-carboxylic acid,
6-(7-chlorobenzo[b]thiophen-5-yl)pyrimidine-4-carboxylic acid,
6-(7-chlorobenzo[d]thiazol-5-yl)pyrimidine-4-carboxylic acid,
6-(7-chlorobenzo[d]oxazol-5-yl)pyrimidine-4-carboxylic acid,
6-(7-chlorobenzo[c][1,2,5]oxadiazol-5-yl)pyrimidine-4-carboxylic acid,
6-(7-chloro-2,3,3a,7a-tetrahydrobenzofuran-5-yl)pyrimidine-4-carboxylic acid,
6-(7-chloro-3a,7a-dihydro-1H-indol-5-yl)pyrimidine-4-carboxylic acid,
6-(7-chloro-1-methyl-3a,7a-dihydro-1H-indazol-5-yl)pyrimidine-4-carboxylic acid,
6-(8-chloroquinazolin-6-yl)pyrimidine-4-carboxylic acid,
6-(5-chloroquinazolin-7-yl)pyrimidine-4-carboxylic acid,
6-(8-chloroquinoxalin-6-yl)pyrimidine-4-carboxylic acid,
6-(8-chloro-1,2,3,4-tetrahydroquinolin-6-yl)pyrimidine-4-carboxylic acid,
6-(7-chloro-1H-benzo[d]imidazol-5-yl)pyrimidine-4-carboxylic acid,
6-(3-chloro-4-(1-methylcyclopropyl)phenyl)pyrimidine-4-carboxylic acid,
6-(3-chloro-4-(1-(trifluoromethyl)cyclopropyl)phenyl)pyrimidine-4-carboxylic acid,
6-(3-chloro-4-(3-methyloxetan-3-yl)phenyl)pyrimidine-4-carboxylic acid,
6-(3-chloro-4-(pyrrolidin-1-yl)phenyl)pyrimidine-4-carboxylic acid,
6-(3-chloro-4-(pyrrolidin-3-yl)phenyl)pyrimidine-4-carboxylic acid,
6-(3-chloro-4-(pyrrolidin-2-yl)phenyl)pyrimidine-4-carboxylic acid,
6-(3-chloro-4-(1H-imidazol-2-yl)phenyl)pyrimidine-4-carboxylic acid,
6-(3-chloro-4-(1H-pyrrol-2-yl)phenyl)pyrimidine-4-carboxylic acid,
6-(4-tert-butyl-3-chlorophenyl)pyrimidine-4-carboxylic acid, and
7-chloro-8-cyclopropoxy-5H-chromeno[4,3-d]pyrimidine-4-carboxylic acid.

or a pharmaceutically acceptable salt or prodrug thereof.
Also provided is a compound chosen from
6-[3-chloro-4-(methylsulfanyl)phenyl]pyrimidine-4-carboxylic acid,
6-[3-chloro-4-(methylsulfinyl)phenyl]pyrimidine-4-carboxylic acid,
6-[3-chloro-4-(methylsulfonyl)phenyl]pyrimidine-4-carboxylic acid,
6-{3-chloro-4-[cyclopropyl(hydroxy)methyl]phenyl}pyrimidine-4-carboxylic acid,
6-(3-chloro-4-cyclopropanecarbonylphenyl)pyrimidine-4-carboxylic acid,
6-[3-chloro-4-(methoxymethyl)phenyl]pyrimidine-4-carboxylic acid,
6-[3-chloro-4-(1-methoxyethyl)phenyl]pyrimidine-4-carboxylic acid,
6-{3-chloro-4-[(dimethylamino)methyl]phenyl}pyrimidine-4-carboxylic acid,
6-[3-chloro-4-(cyclopropylamino)phenyl]pyrimidine-4-carboxylic acid,
6-{3-chloro-4-[cyclopropyl(methyl)amino]phenyl}pyrimidine-4-carboxylic acid,
6-(3-chloro-4-(pyrrolidin-1-yl)phenyl)pyrimidine-4-carboxylic acid,
6-(7-chloro-2-methyl-1,3-benzoxazol-5-yl)pyrimidine-4-carboxylic acid,
6-(8-chloroquinoxalin-6-yl)pyrimidine-4-carboxylic acid,
6-(7-chloro-2,3-dihydro-1-benzofuran-5-yl)pyrimidine-4-carboxylic acid,
6-(7-chloro-2-cyclopropyl-1,3-benzoxazol-5-yl)pyrimidine-4-carboxylic acid,
6-(4-chloro-2-methyl-1,3-benzoxazol-6-yl)pyrimidine-4-carboxylic acid,
6-(7-chloro-3-methyl-2-oxo-2,3-dihydro-1,3-benzoxazol-5-yl)pyrimidine-4-carboxylic acid,
6-(2H-1,3-benzodioxol-5-yl)pyrimidine-4-carboxylic acid,
4-(3,4-dichlorophenyl)-5-methylpyridine-2-carboxylic acid,
6-(3-chloro-4-{[1-(morpholin-4-yl)propan-2-yl]oxy}phenyl)pyrimidine-4-carboxylic acid,
6-[3-chloro-4-(cyclopropoxymethyl)phenyl]pyrimidine-4-carboxylic acid,
6-[3-chloro-4-(cyclopropylmethyl)phenyl]pyrimidine-4-carboxylic acid,
6-[3-chloro-4-(1-cyclopropoxyethyl)phenyl]pyrimidine-4-carboxylic acid,
6-(3-chloro-4-cyclopropylphenyl)pyrimidine-4-carboxylic acid,
6-[4-(aziridin-1-ylmethyl)-3-chlorophenyl]pyrimidine-4-carboxylic acid,
6-{3-chloro-4-[(cyclopropylamino)methyl]phenyl}pyrimidine-4-carboxylic acid,
6-(3-chloro-4-{[cyclopropyl(methyl)amino]methyl}phenyl)pyrimidine-4-carboxylic acid,
6-(7-chloro-2-cyclopropyl-2,3-dihydro-1H-isoindol-5-yl)pyrimidine-4-carboxylic acid,
6-[3-chloro-4-(furan-2-yl)phenyl]pyrimidine-4-carboxylic acid,
6-[3-chloro-4-(1-methoxycyclopropyl)phenyl]pyrimidine-4-carboxylic acid,
6-(2,3-dihydro-1,4-benzodioxin-6-yl)pyrimidine-4-carboxylic acid,
6-(7-chloro-2-oxo-2,3-dihydro-1,3-benzoxazol-5-yl)pyrimidine-4-carboxylic acid, 6-{8-chloroimidazo[1,2-a]pyridin-6-yl}pyrimidine-4-carboxylic acid,
6-(4-chloro-1,3-benzoxazol-6-yl)pyrimidine-4-carboxylic acid,
6-(quinolin-6-yl)pyrimidine-4-carboxylic acid,
6-{pyrazolo[1,5-a]pyridin-5-yl}pyrimidine-4-carboxylic acid,
6-(4-chloro-3-cyclopropoxyphenyl)pyrimidine-4-carboxylic acid,
6-(4-chloro-3-methoxyphenyl)pyrimidine-4-carboxylic acid,
6-[4-chloro-3-(propan-2-yloxy)phenyl]pyrimidine-4-carboxylic acid,
6-[4-chloro-3-(2-methylpropoxy)phenyl]pyrimidine-4-carboxylic acid,
6-[4-chloro-3-(trifluoromethoxy)phenyl]pyrimidine-4-carboxylic acid,
6-{4-chloro-3-[(1,1,1-trifluoropropan-2-yl)oxy]phenyl}pyrimidine-4-carboxylic acid,
6-(2,2-difluorobenzo[d][1,3]dioxol-5-yl)pyrimidine-4-carboxylic acid,
6-(2,3-dihydrobenzo[b][1,4]dioxin-6-yl)pyrimidine-4-carboxylic acid,
6-(7-chlorobenzo[b]thiophen-5-yl)pyrimidine-4-carboxylic acid,
6-(7-chlorobenzo[d]thiazol-5-yl)pyrimidine-4-carboxylic acid,
6-(7-chlorobenzo[d]oxazol-5-yl)pyrimidine-4-carboxylic acid,
6-(7-chlorobenzo[c][1,2,5]oxadiazol-5-yl)pyrimidine-4-carboxylic acid,
6-(7-chloro-3a,7a-dihydro-1H-indol-5-yl)pyrimidine-4-carboxylic acid,
6-(7-chloro-1-methyl-3a,7a-dihydro-1H-indazol-5-yl)pyrimidine-4-carboxylic acid,
6-(8-chloroquinazolin-6-yl)pyrimidine-4-carboxylic acid,
6-(5-chloroquinazolin-7-yl)pyrimidine-4-carboxylic acid,
6-(7-chloro-1H-benzo[d]imidazol-5-yl)pyrimidine-4-carboxylic acid,
6-(3-chloro-4-(1-methylcyclopropyl)phenyl)pyrimidine-4-carboxylic acid,
6-(3-chloro-4-(1-(trifluoromethyl)cyclopropyl)phenyl)pyrimidine-4-carboxylic acid,
6-(3-chloro-4-(3-methyloxetan-3-yl)phenyl)pyrimidine-4-carboxylic acid,
6-(3-chloro-4-(pyrrolidin-2-yl)phenyl)pyrimidine-4-carboxylic acid,
6-(3-chloro-4-(1H-imidazol-2-yl)phenyl)pyrimidine-4-carboxylic acid,
6-(3-chloro-4-(1H-pyrrol-2-yl)phenyl)pyrimidine-4-carboxylic acid,
6-(4-tert-butyl-3-chlorophenyl)pyrimidine-4-carboxylic acid, and
7-chloro-8-cyclopropoxy-5H-chromeno[4,3-d]pyrimidine-4-carboxylic acid,
or a pharmaceutically acceptable salt or prodrug thereof.

Methods for obtaining the chemical entities described herein will be apparent to those of ordinary skill in the art, suitable procedures being described, for example, in examples below, and in the references cited herein.

Provided is a method of inhibiting the catalytic activity of KMO, comprising contacting said KMO with an effective amount of at least one chemical entity described herein.

Also provided is a method of treating a condition or disorder mediated by KMO activity in a subject in need of such a treatment, comprising administering to the subject a therapeutically effective amount of at least one chemical entity described herein.

Also provided is a method of treating a neurodegenerative pathology mediated by KMO activity in a subject in need of such a treatment, comprising administering to the subject a therapeutically effective amount of at least one chemical entity described herein.

Also provided is a method for treating disorders mediated by (or at least in part by) the presence 3-OH-KYN, QUIN and/or KYNA. Also provided is a method of treating a degenerative or inflammatory condition in which an increased synthesis in the brain of QUIN, 3-OH-KYN or increased release of GLU are involved and which may cause neuronal damage.

Such diseases include, for example, Huntington's disease and other polyglutamine disorders such as spinocerebellar ataxias neurodegenerative diseases, psychiatric of neurological diseases or disorders, Alzheimer's disease, Parkinson's disease, amyotropic lateral sclerosis, Creutzfeld-Jacob disease, trauma-induced neurodegeneration, high-pressure neurological syndrome, dystonia, olivopontocerebellar atrophy, amyotrophic lateral sclerosis, multiple sclerosis, epilepsy, consequences of stroke, cerebral ischemia, ischemic disorders including stroke (focal ischemia), hypoxia, multi-infarct dementia, consequences of cerebral trauma or damage, damage to the spinal cord, Dementia such as senile dementia and AIDS-dementia complex, AIDS-induced encephalopathy, other infection related encephalopathy, viral or bacterial meningitis, infectious diseases caused by viral, bacterial and other parasites, for example, general central nervous system (CNS) infections such as viral, bacterial or parasites, for example, poliomyelitis, Lyme disease (*Borrelia burgdorferi* infection) septic shock, and malaria, cancers, cancers with cerebral localization, hepatic encephalopathy, systemic lupus, analgesia and opiate withdrawal symptoms, feeding behavior, psychiatric disorders, such as insomnia, depression, schizophrenia, severe deficit in working memory, severe deficit in long term memory storage, decrease in cognition, severe deficit in attention, severe deficit in executive functioning, slowness in information processing, slowness in neural activity, anxiety, generalized anxiety disorders, panic anxiety, obsessive compulsive disorders, social phobia, performance anxiety, post-traumatic stress disorder, acute stress reaction, adjustment reaction, separation anxiety disorder, alcohol withdrawal anxiety, depressive disorders, disorders of the developing or aged brain, diabetes, and complications thereof, Tourette's syndrome, Fragile X syndrome, autism spectrum disorders, disorders that cause severe and pervasive impairment in thinking feeling, language and the ability to relate to others, mood disorders, psychological disorders characterized by abnormalities of emotional state, such as without limitation, bipolar disorder, unipolar depression, major depression, ondougenous depression, involutional depression, reactive depression, psychotic depression, depression caused by underlying medical conditions, depressive disorders, cyclothymic disorders, dysthymic disorders, mood disorders due to general medical condition, mood disorders not otherwise specified and substance-induced mood disorders. Such disease also include, for example, Acute necrotizing Pancreatitis, AIDS (disease), Analgesia, Aseptic meningitis, Brain disease, for example, Gilles de la Tourette syndrome, Asperger syndrome, Rett syndrome, pervasive developmental disorders, aging-related Brain disease, and developmental Brain disease, burnout syndrome, carbon monoxide poisoning, cardiac arrest or insufficiency and hemorrhagic shock (global brain ischemia), cataract formation and aging of the eye, Central nervous system disease, Cerebrovascular disease, chronic fatigue syndrome, Chronic Stress, Cognitive disorders, convulsive Disorders, such as variants of Grand mal and petit mal epilepsy and Partial Complex Epilepsy, Diabetes mellitus, Disease of the nervous system (e.g., dyskinesia, L-DOPA induced movement disorders, drug addiction, pain and cataract), Drug dependence, Drug withdrawal, feeding disorders, Guillain Barr Syndrome and other neurophaties, Hepatic encephalopathy, Immune disease, immunitary disorders and therapeutic treatment aimed at modifying biological responses (for instance administrations of interferons or interleukins), Inflammation (systemic inflammatory response syndrome), inflammatory disorders of the central and/or peripheral nervous system, Injury (trauma, polytrauma), Mental and behavioral disorders, Metabolic disease, pain disease, or disorder selected from a group of inflammatory pain, neurophathic pain or migraine, allodynia, hyperalgesis pain, phantom pain, neurophatic pain related to diabetic neuropathy, Multiple organ failure, near drowning, Necrosis, neoplasms of the brain, neoplastic disorders including lymphomas and other malignant blood disorders, Nervous system disease (high-pressure neurol. Syndrome, infection), nicotine addiction and other addictive disorders including alcoholism, *cannabis*, benzodiazepine, barbiturate, morphine and cocaine dependence, change in appetite, sleep disorders, changes in sleep patern, lack of energy, fatigue, low self steem, self-reproach inappropriate guilt, frequent thoughts of death or suicide, plans or attemps to commit suicide, feelings of hopelessness and worthlessness, psychomotor agitation or retardation, diminished capacity for thinking, concentration, or decisiveness, as a Neuroprotective agents, Pain, Post-traumatic stress disorder, Sepsis, Spinal cord disease, Spinocerebellar ataxia, Systemic lupus erythematosis, traumatic damage to the brain and spinal cord, and tremor syndromes and different movement disorders (diskynesia). Poor balance, brakykinesia, rigidity, tremor, change in speech, loss of facial expression, micrographia, difficulty swallowing, drooling, dementia, confussion, fear, sexual disfunction, language impairment, impairment in decision making, violent outbursts, aggression, hallucination, apathy, impairment in abstract thinking.

Such diseases include, for example, cardiovascular diseases, which refers to diseases and disorders of the heart and circulatory system. These diseases are often associated with dyslipoproteinemias and/or dyslipidemias. Cardiovascular diseases include but are not limited to cardiomegaly, atherosclerosis, myocardial infarction, and congestive heart failure, coronary heart disease, hypertension and hypotension.

Other such diseases include hyperproliferative diseases of benign or malignant behaviour, in which cells of various tissues and organs exhibit aberrant patterns of growth, proliferation, migration, signaling, senescence, and death. Generally hyperpoliferative disease refers to diseases and disorders associated with, the uncontrolled proliferation of cells, including but not limited to uncontrolled growth of organ and tissue cells resulting in cancers and benign tumors. Hyperproliferative disorders associated with endothelial cells can result in diseases of angiogenesis such as angiomas, endometriosis, obesity, Age-related Macular Degeneration and various retinopaties, as well as the proliferation of ECs and smooth muscle cells that cause restenosis as a consequence of stenting in the treatment of atherosclerosis. Hyperproliferative disorders involving fibroblasts (i.e., fibrogenesis) include but are not limited to disorders of excessive scaring (i.e., fibrosis) such as Age-related Macular Degeneration, cardiac remodeling and failure associated with myocardial infarction, excessive wound healing such as commonly occurs as a consequence of surgery or injury, keloids, and fibroid tumors and stenting.

Additional diseases include transplant rejection (suppression of T-cells) and graft vs host disease, chronic kidney disease, systemic inflammatory disorders, brain inflammatory disorders including malaria and African trypanosomiasis, stroke, and pneumococcal meningitis.

Also provided are methods of treatment in which at least one chemical entity described herein is the only active agent given to the subject and also includes methods of treatment in which at least one chemical entity described herein is given to the subject in combination with one or more additional active agents.

In general, the chemical entities described herein will be administered in a therapeutically effective amount by any of the accepted modes of administration for agents that serve similar utilities. The actual amount of the compound, i.e., the active ingredient, will depend upon numerous factors such as the severity of the disease to be treated, the age and relative health of the subject, the potency of the compound used, the route and form of administration, and other factors well know to the skilled artisan. The drug can be administered at least once a day, such as once or twice a day.

In some embodiments, the chemical entities described herein are administered as a pharmaceutical composition. Accordingly, provided are pharmaceutical compositions comprising at least one chemical entity described herein, together with at least one pharmaceutically acceptable vehicle chosen from carriers, adjuvants, and excipients.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the chemical entity is sufficient to provide a practical quantity of material for administration per unit dose of the chemical entity.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENS; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the chemical entity described herein.

Effective concentrations of at least one chemical entity described herein are mixed with a suitable pharmaceutically acceptable vehicle. In instances in which the chemical entity exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate.

Upon mixing or addition of a chemical entity described herein, the resulting mixture may be a solution, suspension, emulsion or the like. The form of the resulting mixture depends upon a number of factors, including the intended mode of administration and the solubility of the chemical entity in the chosen vehicle. The effective concentration sufficient for ameliorating the symptoms of the disease treated may be empirically determined.

Chemical entities described herein may be administered orally, topically, parenterally, intravenously, by intramuscular injection, by inhalation or spray, sublingually, transdermally, via buccal administration, rectally, as an ophthalmic solution, or by other means, in dosage unit formulations.

Pharmaceutical compositions may be formulated for oral use, such as for example, tablets, troches, lozenges, aqueous or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral pharmaceutical compositions contain from 0.1 to 99% of at least one chemical entity described herein. In some embodiments, oral pharmaceutical compositions contain at least 5% (weight %) of at least one chemical entity described herein. Some embodiments contain from 25% to 50% or from 5% to 75% of at least one chemical entity described herein.

Orally administered pharmaceutical compositions also include liquid solutions, emulsions, suspensions, powders, granules, elixirs, tinctures, syrups, and the like. The pharmaceutically acceptable carriers suitable for preparation of such compositions are well known in the art. Oral pharmaceutical compositions may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such pharmaceutical compositions may also contain a demulcent.

Chemical entities described herein can be incorporated into oral liquid preparations such as aqueous or oily suspensions, solutions, emulsions, syrups, or elixirs, for example. Moreover, pharmaceutical compositions containing these chemical entities can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, Avicel RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These pharmaceutical compositions may be preserved by the addition of an anti-oxidant such as ascorbic acid.

Pharmaceutical compositions may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

Such pharmaceutical compositions may also be coated by conventional methods, typically with pH or time-dependent coatings, such that the chemical entity is released in the gastrointestinal tract in the vicinity of the desired topical application, or at various times to extend the desired action.

Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables.

Chemical entities described herein may be administered parenterally in a sterile medium. Parenteral administration includes subcutaneous injections, intravenous, intramuscular, intrathecal injection or infusion techniques. Chemical entities described herein, depending on the vehicle and concentration used, can either be suspended or dissolved in the vehicle. Advantageously, adjuvants such as local anesthetics, preservatives and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

Chemical entities described herein may also be administered in the form of suppositories for rectal administration of the drug. These pharmaceutical compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

Chemical entities described herein may be formulated for local or topical application, such as for topical application to the skin and mucous membranes, such as in the eye, in the form of gels, creams, and lotions and for application to the eye. Topical pharmaceutical compositions may be in any form including, for example, solutions, creams, ointments, gels, lotions, milks, cleansers, moisturizers, sprays, skin patches, and the like.

Such solutions may be formulated as 0.01%-10% isotonic solutions, pH 5-7, with appropriate salts. Chemical entities described herein may also be formulated for transdermal administration as a transdermal patch.

Topical pharmaceutical compositions comprising at least one chemical entity described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, *arachis* oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The chemical entities described herein may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other pharmaceutical compositions useful for attaining systemic delivery of the chemical entity include sublingual, buccal and nasal dosage forms. Such pharmaceutical compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Pharmaceutical compositions for inhalation typically can be provided in the form of a solution, suspension or emulsion that can be administered as a dry powder or in the form of an aerosol using a conventional propellant (e.g., dichlorodifluoromethane or trichlorofluoromethane).

The pharmaceutical compositions may also optionally comprise an activity enhancer. The activity enhancer can be chosen from a wide variety of molecules that function in different ways to enhance or be independent of therapeutic effects of the chemical entities described herein. Particular classes of activity enhancers include skin penetration enhancers and absorption enhancers.

Pharmaceutical compositions may also contain additional active agents that can be chosen from a wide variety of molecules, which can function in different ways to enhance the therapeutic effects of at least one chemical entity described herein. These optional other active agents, when present, are typically employed in the pharmaceutical compositions at a level ranging from 0.01% to 15%. Some embodiments contain from 0.1% to 10% by weight of the composition. Other embodiments contain from 0.5% to 5% by weight of the composition.

Also provided are packaged pharmaceutical compositions. Such packaged compositions include a pharmaceutical composition comprising at least one chemical entity described herein, and instructions for using the composition to treat a subject (typically a human patient). In some embodiments, the instructions are for using the pharmaceutical composition to treat a subject suffering a condition or disorder mediated by Kynurenine 3-mono-oxygenase activity. The packaged pharmaceutical composition can include providing prescribing information; for example, to a patient or health care provider, or as a label in a packaged pharmaceutical composition. Prescribing information may include for example efficacy, dosage and administration, contraindication and adverse reaction information pertaining to the pharmaceutical composition.

In all of the foregoing the chemical entities can be administered alone, as mixtures, or in combination with other active agents.

The methods described herein include methods for treating Huntington's disease, including treating memory and/or cognitive impairment associated with Huntington's disease, comprising administering to a subject, simultaneously or sequentially, at least one chemical entity described herein and one or more additional agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. In methods using simultaneous administration, the agents can be present in a combined composition or can be administered separately. As a result, also provided are pharmaceutical compositions comprising at least one chemical entity described herein and one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. Similarly, also provided arepackaged pharmaceutical compositions containing a pharmaceutical composition comprising at least one chemical entity described herein, and another composition comprising one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone.

Also provided are methods for treating Parkinson's disease, including treating memory and/or cognitive impairment associated with Parkinson's disease, comprising administering to a subject, simultaneously or sequentially, at least one chemical entity described herein and one or more additional agents used in the treatment of Parkinson's disease such as, but not limited to, Levodopa, Parlodel, Permax, Mirapex, Tasmar, Contan, Kemadin, Artane, and Cogentin. In methods using simultaneous administration, the agents can be present in a combined composition or can be administered separately. Also provided are pharmaceutical compositions comprising at least one chemical entity described herein, and one or more additional pharmaceutical agents used in the treatment of Parkinson's disease, such as, but not limited to, Levodopa, Parlodel, Permax, Mirapex, Tasmar, Contan, Kemadin, Artane, and Cogentin. Also provided are packaged pharmaceutical compositions containing a pharmaceutical composition comprising at least one chemical entity described herein, and another composition comprising one or more additional pharmaceutical agents gent used in the treatment of Parkinson's disease such as, but not limited to, Levodopa, Parlodel, Permax, Mirapex, Tasmar, Contan, Kemadin, Artane, and Cogentin.

Also provided are methods for treating memory and/or cognitive impairment associated with Alzheimer's disease, comprising administering to a subject, simultaneously or sequentially, at least one chemical entity described herein and one or more additional agents used in the treatment of Alzheimer's disease such as, but not limited to, Reminyl, Cognex, Aricept, Exelon, Akatinol, Neotropin, Eldepryl, Estrogen and Cliquinol. In methods using simultaneous administration, the agents can be present in a combined composition or can be administered separately. Also provided are pharmaceutical compositions comprising at least one chemical entity described herein, and one or more additional pharmaceutical agents used in the treatment of Alzheimer's disease such as, but not limited to, Reminyl, Cognex, Aricept, Exelon, Akatinol, Neotropin, Eldepryl, Estrogen and Cliquinol. Similarly, also provided are packaged pharmaceutical compositions containing a pharmaceutical composition comprising at least one chemical entity described herein, and another composition comprising one or more additional pharmaceutical agents used in the treatment of Alzheimer's disease such as, but not limited to Reminyl, Cognex, Aricept, Exelon, Akatinol, Neotropin, Eldepryl, Estrogen and Cliquinol.

Also provided are methods for treating memory and/or cognitive impairment associated with dementia or cognitive impairment comprising administering to a subject, simultaneously or sequentially, at least one chemical entity and one or more additional agents used in the treatment of dementia such as, but not limited to, Thioridazine, Haloperidol, Risperidone, Cognex, Aricept, and Exelon. In methods using simultaneous administration, the agents can be present in a combined composition or can be administered separately. Also provided are pharmaceutical compositions comprising at least one chemical entity described herein, and one or more additional pharmaceutical agents used in the treatment of dementia such as, but not limited to, Thioridazine, Haloperidol, Risperidone, Cognex, Aricept, and Exelon. Also provided are packaged pharmaceutical compositions containing a pharmaceutical composition comprising at least one chemical entity described herein, and another composition comprising one or more additional pharmaceutical agents used in the treatment of dementia such as, but not limited to, Thioridazine, Haloperidol, Risperidone, Cognex, Aricept, and Exelon.

Also provided are methods for treating memory and/or cognitive impairment associated with epilepsy comprising administering to a subject, simultaneously or sequentially, at least one chemical entity described herein and one or more additional agents used in the treatment of epilepsy such as, but not limited to, Dilantin, Luminol, Tegretol, Depakote, Depakene, Zarontin, Neurontin, Barbita, Solfeton, and Felbatol. In methods using simultaneous administration, the agents can be present in a combined composition or can be administered separately. Also provided are pharmaceutical compositions comprising at least one chemical entity described herein, and one or more additional pharmaceutical agents used in the treatment of epilepsy such as, but not limited to, Dilantin, Luminol, Tegretol, Depakote, Depakene, Zarontin, Neurontin, Barbita, Solfeton, and Felbatol.

Also provided are packaged pharmaceutical compositions containing a pharmaceutical composition comprising at least one chemical entity described herein, and another composition comprising one or more additional pharmaceutical agents used in the treatment of epilepsy such as, but not limited to, Dilantin, Luminol, Tegretol, Depakote, Depakene, Zarontin, Neurontin, Barbita, Solfeton, and Felbatol.

Also provided are methods for treating memory and/or cognitive impairment associated with multiple sclerosis comprising administering to a subject, simultaneously or sequentially, at least one chemical entity described herein and one or more additional agents used in the treatment of multiple sclerosis such as, but not limited to, Detrol, Ditropan XL, OxyContin, Betaseron, Avonex, Azothioprine, Methotrexate, and Copaxone. In methods using simultaneous administration, the agents can be present in a combined composition or can be administered separately. Also provided are pharmaceutical compositions comprising at least one chemical entity described herein, and one or more additional pharmaceutical agents used in the treatment of multiple sclerosis such as, but not limited to, Detrol, Ditropan XL, OxyContin, Betaseron, Avonex, Azothioprine, Methotrexate, and Copaxone. Also provided are packaged pharmaceutical compositions containing a pharmaceutical composition comprising at least one chemical entity described herein, and another composition comprising one or more additional pharmaceutical agents used in the treatment of multiple sclerosis such as, but not limited to, Detrol, Ditropan XL, OxyContin, Betaseron, Avonex, Azothioprine, Methotrexate, and Copaxone.

When used in combination with one or more additional pharmaceutical agent or agents, the described herein may be administered prior to, concurrently with, or following administration of the additional pharmaceutical agent or agents.

The dosages of the compounds described herein depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The chemical entities described herein are typically administered at dosage levels and in a manner customary for KMO inhibitors. For example, the chemical entities can be administered, in single or multiple doses, by oral administration at a dosage level of generally 0.001-100 mg/kg/day, for example, 0.01-100 mg/kg/day, such as 0.1-70 mg/kg/day, for example, 0.5-10 mg/kg/day. Unit dosage forms can contain generally 0.01-1000 mg of at least one chemical entity described herein, for example, 0.1-50 mg of at least one chemical entity described herein. For intravenous administration, the compounds can be administered, in single or multiple dosages, at a dosage level of, for example, 0.001-50 mg/kg/day, such as 0.001-10 mg/kg/day, for example, 0.01-1 mg/kg/day. Unit dosage forms can contain, for example, 0.1-10 mg of at least one chemical entity described herein.

A labeled form of a chemical entity described herein can be used as a diagnostic for identifying and/or obtaining compounds that have the function of modulating an activity of KMO as described herein. The chemical entities described herein may additionally be used for validating, optimizing, and standardizing bioassays.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In carrying out the procedures of the methods described herein, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

EXAMPLES

The chemical entities, compositions, and methods described herein are further illustrated by the following non-limiting examples.

As used herein, the following abbreviations have the following meanings. If an abbreviation is not defined, it has its generally accepted meaning CDI=carbonyldiimidazole DCM=dichloromethane DME=dimethyl ether DMEM=Dulbecco's modified Eagle's medium DMF=N,N-dimethylformamide DMSO=dimethylsulfoxide EDC.HCl=1-Ethyl-3-(3-dimethylaminopropyl)carbodiimide hydrochloride EtOH=ethanol $Et_2O$=diethylether EtOAc=ethyl acetate g=gram hr=hour hrs=hours HOBt=1-Hydroxybenzotriazol LiHMDS=lithium hexamethyl-disilazide LC/MS=liquid chromatography/mass spectrometry mg=milligram min=minutes mL=milliliter mmol=millimoles mM=millimolar ng=nanogram nm=nanometer nM=nanomolar PBS=phosphate buffered saline rt=room temperature TBME=t-butyl methyl ether
THF=tetrahydrofuran
TMOF=trimethylorthoformate
μL=microliter
μM=micromolar
1 g/1 ml=1 vol Experimental Commercially available reagents and solvents (HPLC grade) were used without further purification.

Thin-layer chromatography (TLC) analysis was performed with Kieselgel 60 F254 (Merck) plates and visualized using UV light. Microwave reactions were carried out using CEM focussed microwaves.

Analytical HPLC-MS was performed on Agilent HP1100 and Shimadzu 2010, systems using reverse phase Atlantis dC18 columns (5 μm, 2.1×50 mm), gradient 5-100% B (A=water/0.1% formic acid, B=acetonitrile/0.1% formic acid) over 3 min, injection volume 3 μl, flow=1.0 ml/min. UV spectra were recorded at 215 nm using a Waters 2487 dual wavelength UV detector or the Shimadzu 2010 system. Mass spectra were obtained over the range m/z 150 to 850 at a sampling rate of 2 scans per second using Waters ZMD and over m/z 100 to 1000 at a sampling rate of 2 Hz using Electrospray ionisation, by a Shimadzu 2010 LC-MS system or analytical HPLC-MS was performed on Agilent HP1100 and Shimadzu 2010, systems using reverse phase Water Atlantis dC18 columns (3 μm, 2.1×100 mm), gradient 5-100% B (A=water/0.1% formic acid, B=acetonitrile/0.1% formic acid) over 7 min, injection volume 3 μl, flow=0.6 ml/min. UV spectra were recorded at 215 nm using a Waters 2996 photo diode array or on the Shimadzu 2010 system. Mass spectra were obtained over the range m/z 150 to 850 at a sampling rate of 2 scans per second using Waters ZQ and over m/z 100 to 1000 at a sampling rate of 2 Hz using Electrospray ionisation, by a Shimadzu 2010 LC-MS system. Data were integrated and reported using OpenLynx and OpenLynx Browser software or via Shimadzu PsiPort software.

Example 1

Reaction Scheme 1

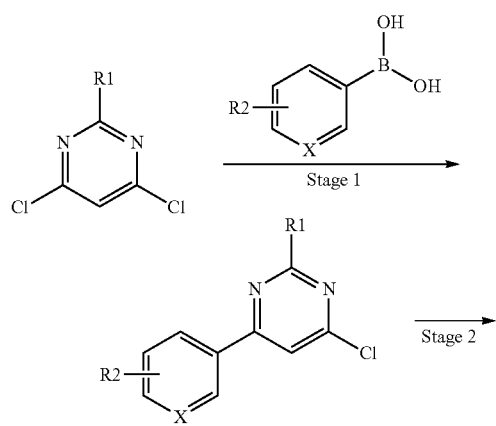

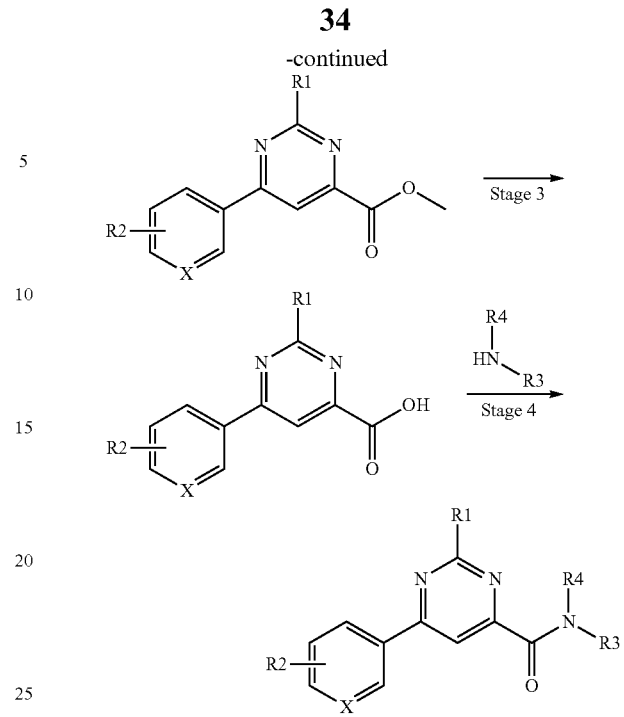

Referring to Reaction Scheme 1, Stage 1, to a stirred suspension of dichloropyrimidine (1 eq) in 1,4-dioxane (15 vol) was added boronic acid (0.7 eq) and Pd(PPh3)4 (0.025 eq). A 2M K2CO3 solution (7.5 vol) was added to the resulting mixture, which was heated at 90° C. overnight under an atmosphere of N2. The reaction mixture was cooled to room temperature and concentrated in vacuo. The residue was dissolved in EtOAc:water (1:1) (100 vol) and the resulting solution filtered through celite. The organic layer was separated and the aqueous layer further extracted with EtOAc (50 vol). The combined organic layers were washed with saturated aqueous NaCl (20 vol), dried over Na2SO4, filtered and the solvent removed in vacuo. The resulting residue was purified by flash column chromatography (eluent: [0:1 to 1:19] EtOAc:heptane) to afford the required target compounds.

Referring to Reaction Scheme 1, Stage 2, 4-chloro-6-substituted-phenyl-pyrimidine (1 eq), PdCl2(dppf).DCM (0.05 eq) and triethylamine (2 eq) were suspended in degassed MeOH (50 vol) in a bomb fitted with a magnetic stirrer bar. The atmosphere in the reaction vessel was replaced with N2 by successive evacuation and charging with N2 gas (this process was repeated three times). The bomb was then flushed with CO by successive charging with CO and evacuation. The vessel was pressurised to 5 bar of CO and heated at 50° C. with stirring for 5 hours. The reaction vessel was allowed to cool to room temperature before venting CO and flushing with N2. The reaction mixture was concentrated in vacuo and the resulting residue dissolved in EtOAc (30 vol) and water (30 vol). The solution was filtered through cotton wool and the organic layer was separated, washed with saturated aqueous NaCl (15 vol), dried over Na2SO4, filtered and concentrated under reduced pressure. Purification by flash column chromatography (eluent: [0:1 to 1:9] EtOAc:heptane) yielded the target compounds.

Referring to Reaction Scheme 1, Stage 3, 6-substituted-phenyl-pyrimidine-4-carboxylic acid methyl ester (1 eq) was suspended in MeOH (20 vol), 1M NaOH solution (20 vol) and stirred at room temperature for 4 hours. The reaction mixture was acidified with 2M HCl. Soluble products were extracted with DCM (2×20 vol) and the combined organic layers were dried over MgSO4, filtered and concentration under reduced pressure afforded the target compounds. Insoluble products were filtered, washed with water (3×10 vol) and heptane (3×10 vol) before drying in vacuo to yield the target compounds.

Referring to Reaction Scheme 1, Stage 4, the required amide analogues were prepared following the procedures described in method A, B, C or D.

The following compounds were prepared substantially as described above.

| Structure | Molecular Weight | Mass Spec Result |
|---|---|---|
| 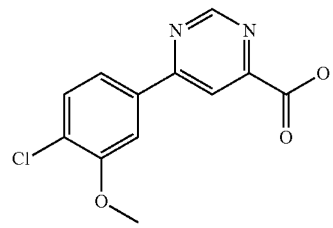 [SMILES: COc1cc(-c2cc(C(=O)O)ncn2)ccc1Cl] | 264.67 | [M + H]$^+$ = 265/267, 100% @ rt = 3.53 and 3.70 min |
| 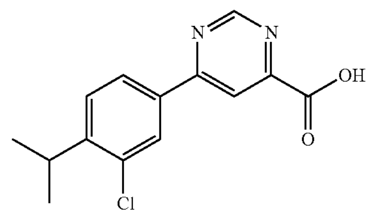 [SMILES: CC(C)c1ccc(-c2cc(C(=O)O)ncn2)cc1Cl] | 276.72 | [M + H]$^+$ = 277/279, 99.9% @ rt = 4.32 min |
| 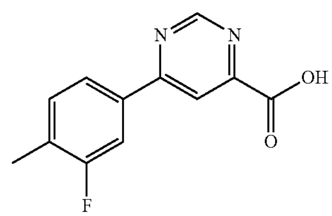 [SMILES: Cc1ccc(-c2cc(C(=O)O)ncn2)cc1F] | 232.22 | [M + H]$^+$ = 232, 100% @ rt = 3.52 min |
| 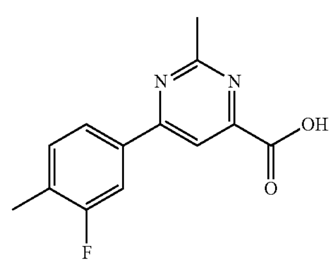 [SMILES: Cc1nc(C(=O)O)cc(-c2ccc(C)c(F)c2)n1] | 246.24 | [M + H]$^+$ = 247, 100% @ rt = 3.66 min |
| 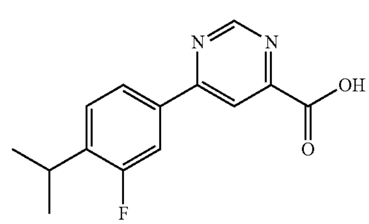 [SMILES: CC(C)c1ccc(-c2cc(C(=O)O)ncn2)cc1F] | 260.27 | [M + H]$^+$ = 261.4, 100% @ rt = 4.13 min |
| 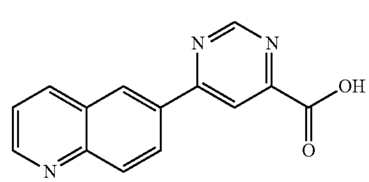 [SMILES: O=C(O)c1cc(-c2ccc3ncccc3c2)ncn1] | 251.25 | [M + H]$^+$ = 252, 99% @ rt = 2.32 min |

| Structure | Molecular Weight | Mass Spec Result |
|---|---|---|
| (structure shown) | 319.75 | [M + H]+ = 320, 97% @ rt = 2.29 min |

Example 2

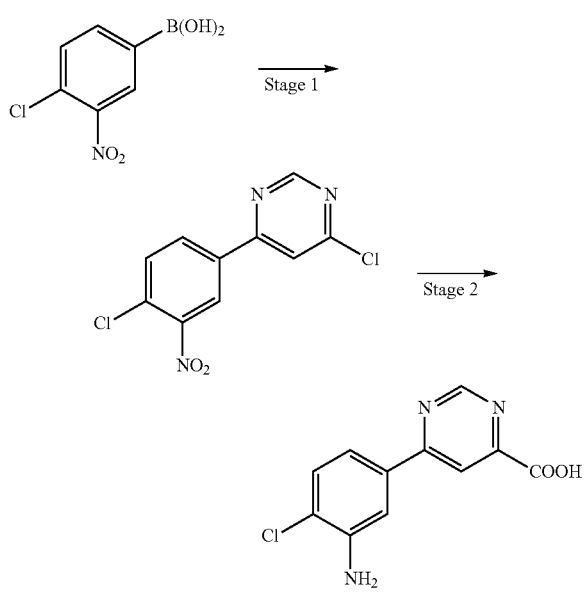

Reaction Scheme 2

Referring to Reaction Scheme 2, Stage 1, to a degassed stirred solution of 4-chloro-3-nitro-benzene boronic acid (1 eq) and 4,6-dichloropyrimidine (1.44 eq) in 1,4-dioxane (16 vol) and 2N K2CO3 (8 vol) was added Pd(PPh3)4 (0.06 eq) and the mixture heated to 90° C. for 3.75 hours under an atmosphere of nitrogen gas. The cooled reaction mixture had the solvents removed under reduced pressure. DCM (25 vol) and water (25 vol) were then added and the undissolved material removed by filtration through celite. The organic phase from the filtrate was concentrated under reduced pressure whilst adsorbing on to silica gel (8.2 g). The residue was purified using dry flash chromatography (gradient up to 10% EtOAc:heptane) to afford the target compound.

Referring to Reaction Scheme 2, Stage 2, in a metal vessel equipped to carry out high pressure reactions, a degassed suspension of 4-chloro-6-(4-chloro-3-nitro-phenyl)-pyrimidine (1 eq) was stirred in MeOH (62 vol). Triethylamine (2 eq) and Pd(PPh3)4 (0.05 eq) was then added and the vessel sealed. The vessel was then charged with carbon monoxide gas to a pressure of 5 bar and heated to 50° C. for 18 hours. After extrusion of excess carbon monoxide gas, the organic solvent was concentrated under reduced pressure. To the residue was added DCM (26 vol) and the undissolved material was filtered off and washed with DCM (10 vol). The filtrate was washed with 2N HCl (10 vol), a 1:1 mixture of water and brine (10 vol) and then concentrated under reduce pressure whilst adsorbing onto silica gel (3.2 g). The residue was purified by dry flash column chromatography (gradient up to 60% EtOAc:heptane) to give a mixture of products, the major identified as the methyl ester. The solid was then dissolved in 2N HCl (30 vol) and washed with TBME (1×30 vol & 1×20 vol). The aqueous layer was adjusted to pH7 and the precipitate formed was filtered off, washed with water (2×5 vol) and air dried to afford the target compound.

| Structure | Molecular Weight | Mass Spec Result |
|---|---|---|
| (structure shown) | 249.66 | [M + H]+ = 250/252, 96% @ rt = 3.43 min |

Example 3

Reaction Scheme 3

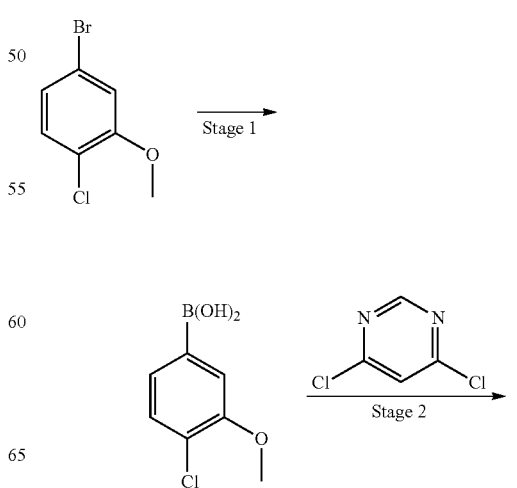

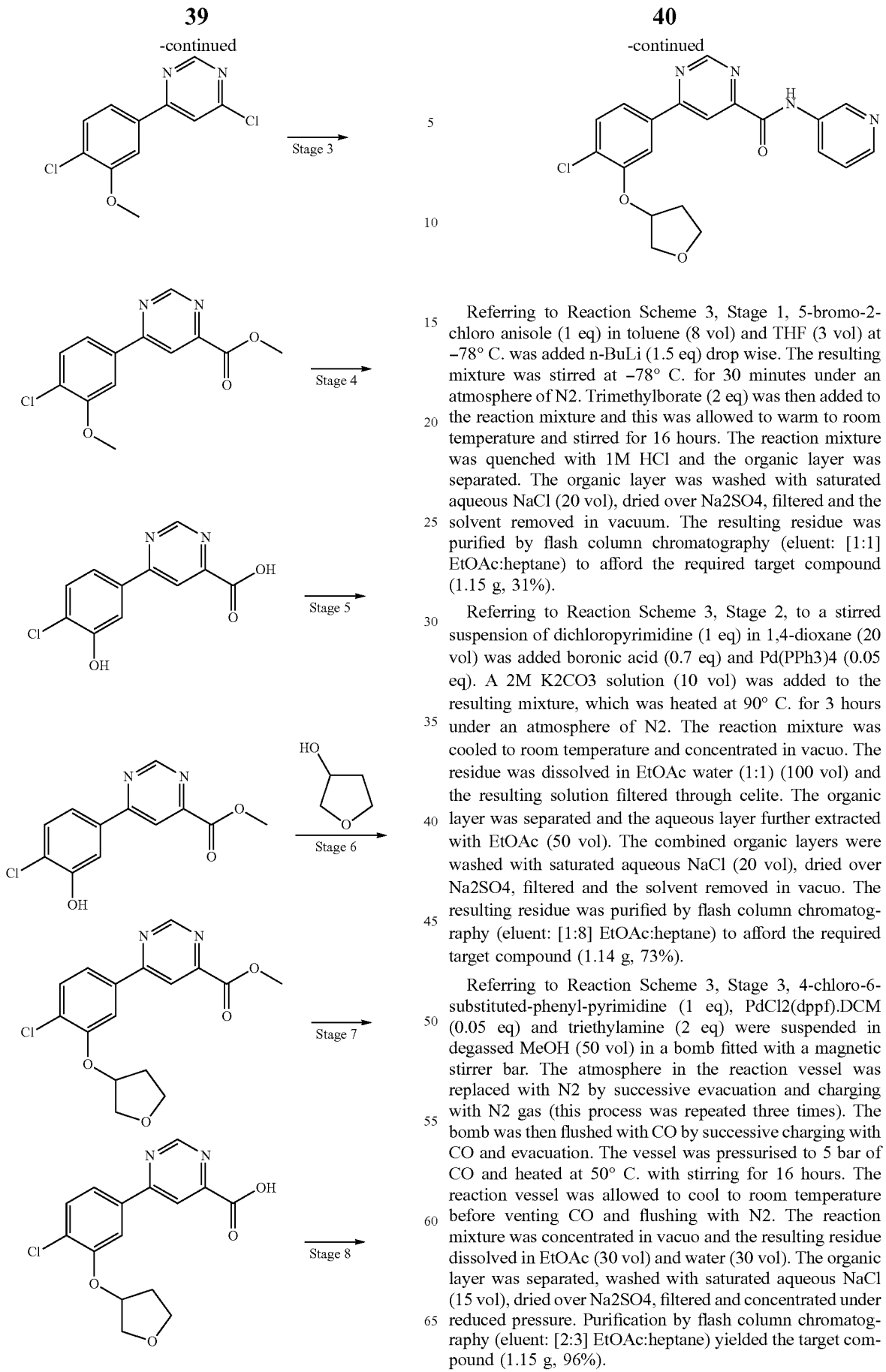

Referring to Reaction Scheme 3, Stage 1, 5-bromo-2-chloro anisole (1 eq) in toluene (8 vol) and THF (3 vol) at −78° C. was added n-BuLi (1.5 eq) drop wise. The resulting mixture was stirred at −78° C. for 30 minutes under an atmosphere of N2. Trimethylborate (2 eq) was then added to the reaction mixture and this was allowed to warm to room temperature and stirred for 16 hours. The reaction mixture was quenched with 1M HCl and the organic layer was separated. The organic layer was washed with saturated aqueous NaCl (20 vol), dried over Na2SO4, filtered and the solvent removed in vacuum. The resulting residue was purified by flash column chromatography (eluent: [1:1] EtOAc:heptane) to afford the required target compound (1.15 g, 31%).

Referring to Reaction Scheme 3, Stage 2, to a stirred suspension of dichloropyrimidine (1 eq) in 1,4-dioxane (20 vol) was added boronic acid (0.7 eq) and Pd(PPh3)4 (0.05 eq). A 2M K2CO3 solution (10 vol) was added to the resulting mixture, which was heated at 90° C. for 3 hours under an atmosphere of N2. The reaction mixture was cooled to room temperature and concentrated in vacuo. The residue was dissolved in EtOAc water (1:1) (100 vol) and the resulting solution filtered through celite. The organic layer was separated and the aqueous layer further extracted with EtOAc (50 vol). The combined organic layers were washed with saturated aqueous NaCl (20 vol), dried over Na2SO4, filtered and the solvent removed in vacuo. The resulting residue was purified by flash column chromatography (eluent: [1:8] EtOAc:heptane) to afford the required target compound (1.14 g, 73%).

Referring to Reaction Scheme 3, Stage 3, 4-chloro-6-substituted-phenyl-pyrimidine (1 eq), PdCl2(dppf).DCM (0.05 eq) and triethylamine (2 eq) were suspended in degassed MeOH (50 vol) in a bomb fitted with a magnetic stirrer bar. The atmosphere in the reaction vessel was replaced with N2 by successive evacuation and charging with N2 gas (this process was repeated three times). The bomb was then flushed with CO by successive charging with CO and evacuation. The vessel was pressurised to 5 bar of CO and heated at 50° C. with stirring for 16 hours. The reaction vessel was allowed to cool to room temperature before venting CO and flushing with N2. The reaction mixture was concentrated in vacuo and the resulting residue dissolved in EtOAc (30 vol) and water (30 vol). The organic layer was separated, washed with saturated aqueous NaCl (15 vol), dried over Na2SO4, filtered and concentrated under reduced pressure. Purification by flash column chromatography (eluent: [2:3] EtOAc:heptane) yielded the target compound (1.15 g, 96%).

Referring to Reaction Scheme 3, Stage 4, to a solution of 6-Substituted-phenyl-pyrimidine-4-carboxylic acid methyl ester (1 eq) in DCM (80 vol) at −78° C. was added BBr3 (3 eq) under nitrogen. The reaction mixture was warm to 0° C. and stirred for 1 hour then allowed to stir at room temperature for 16 hours. The reaction mixture was poured into ice (100 vol) and extracted with EtOAc (150 vol). The organic layer was separated, washed with saturated aqueous NaCl (15 vol), dried over Na2SO4, filtered and concentrated under reduced pressure. The crude mixture (0.45 g) was used in the next step without further purification.

Referring to Reaction Scheme 3, Stage 5, a solution of 6-substituted-phenyl-pyrimidine-4-carboxylic acid (1 eq) in MeOH (100 vol) was added concentrated H2SO4 (2 drops). The reaction mixture was refluxed for 4 hours. The reaction mixture was concentrated in vacuo and the resulting residue dissolved in EtOAc (30 vol) and water (30 vol). The organic layer was separated, washed with saturated aqueous NaCl (15 vol), dried over Na2SO4, filtered and concentrated under reduced pressure. The crude mixture (0.48 g) was used in the next step without further purification.

Referring to Reaction Scheme 3, Stage 6, to a solution of 6-substituted-phenyl-pyrimidine-4-carboxylic acid methyl ester (1.05 eq) in THF (10 vol) were added 3-hydroxy furan (1 eq) and PPh3 (1.5 eq) under nitrogen. The reaction mixture was cooled to 0° C. and DIAD (1.5 eq) was added slowly. Reaction mixture was allowed to warm to room temperature and stirred for 16 hours. The reaction mixture was concentrated in vacuo and the resulting residue was triturated with EtOAc and heptane (1:2) and solid was filtered to give the desired compound (0.42 g, 70%).

Referring to Reaction Scheme 3, Stage 7, 6-substituted-phenyl-pyrimidine-4-carboxylic acid methyl ester (1 eq) was suspended in THF (20 vol), 2M NaOH (3.14 ml, 6.28 mmol, 5 eq) and stirred at room temperature for 4 hours. The THF was removed under vacuo, MeCN (10 vol) was added and the reaction mixture was acidified with 6M HCl. The resulting solid was filtered and washed with water and a mixture of MeCN: water (1:1) to give desired product (0.335 g, 83%).

Referring to Reaction Scheme 3, Stage 3, the required amide analogue was prepared following the procedure described in method B.

The following compounds were prepared substantially as described above.

| Structure | Molecular Weight | Mass Spec Result |
|---|---|---|
| 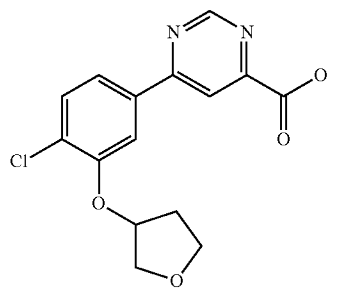 [SMILES: O=C(O)c1cc(-c2ccc(Cl)c(OC3CCOC3)c2)ncn1] | 320.73 | [M + H]+ = 321/323, 100% @ rt = 3.55-3.82 min |
| 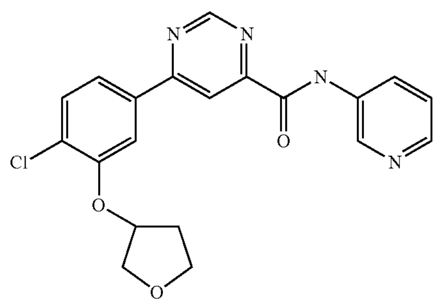 [SMILES: O=C(Nc1cccnc1)c1cc(-c2ccc(Cl)c(OC3CCOC3)c2)ncn1] | 396.84 | [M + H]+ = 397/399, 98% @ rt = 3.7 min |

Example 4

Reaction Scheme 4

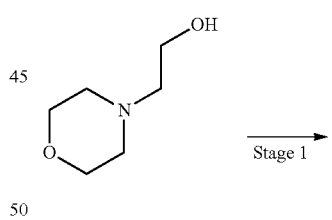

Stage 1

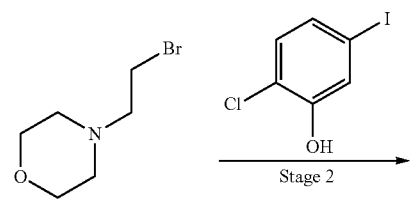

Stage 2

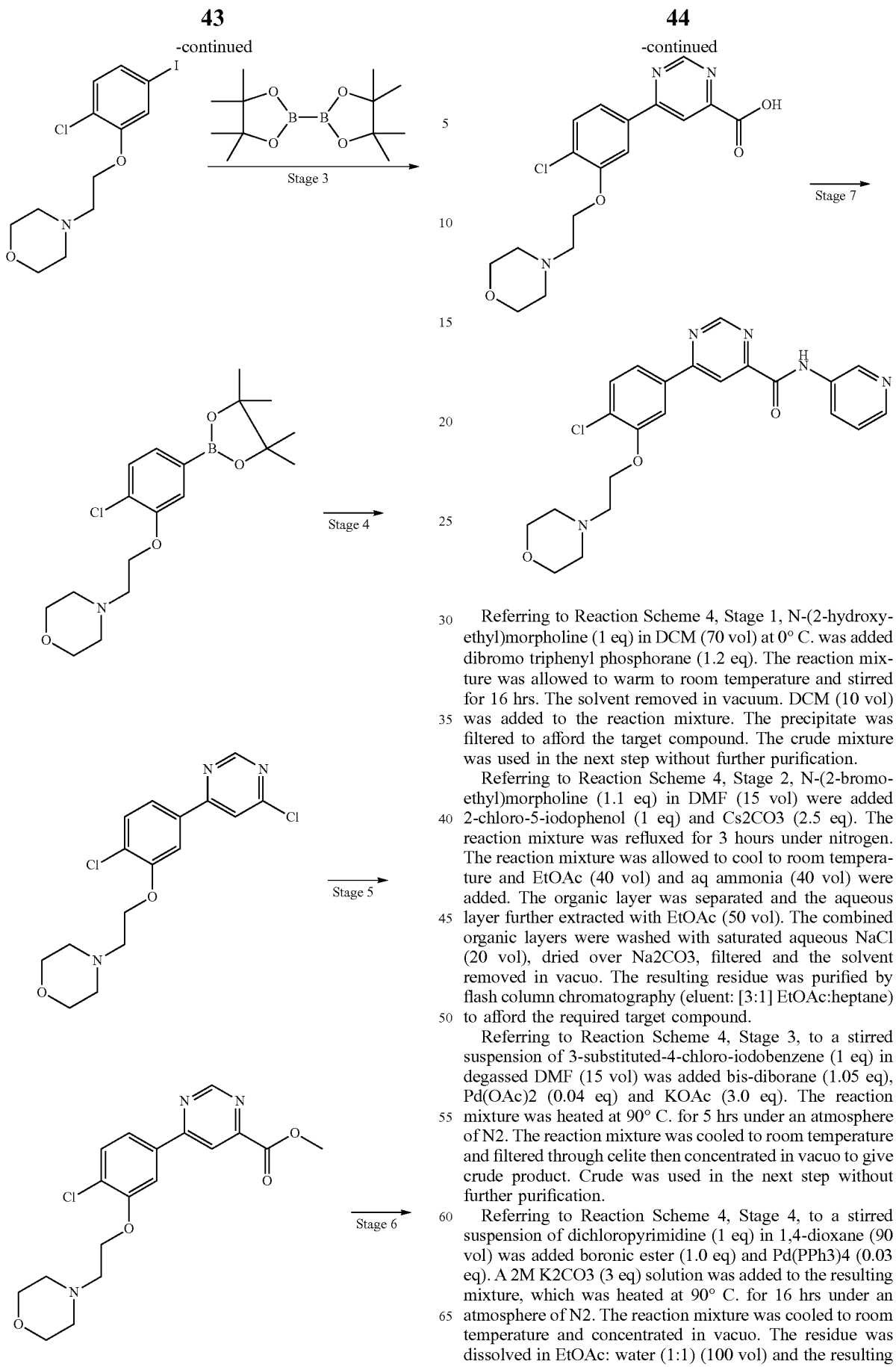

Referring to Reaction Scheme 4, Stage 1, N-(2-hydroxyethyl)morpholine (1 eq) in DCM (70 vol) at 0° C. was added dibromo triphenyl phosphorane (1.2 eq). The reaction mixture was allowed to warm to room temperature and stirred for 16 hrs. The solvent removed in vacuum. DCM (10 vol) was added to the reaction mixture. The precipitate was filtered to afford the target compound. The crude mixture was used in the next step without further purification.

Referring to Reaction Scheme 4, Stage 2, N-(2-bromoethyl)morpholine (1.1 eq) in DMF (15 vol) were added 2-chloro-5-iodophenol (1 eq) and Cs2CO3 (2.5 eq). The reaction mixture was refluxed for 3 hours under nitrogen. The reaction mixture was allowed to cool to room temperature and EtOAc (40 vol) and aq ammonia (40 vol) were added. The organic layer was separated and the aqueous layer further extracted with EtOAc (50 vol). The combined organic layers were washed with saturated aqueous NaCl (20 vol), dried over Na2CO3, filtered and the solvent removed in vacuo. The resulting residue was purified by flash column chromatography (eluent: [3:1] EtOAc:heptane) to afford the required target compound.

Referring to Reaction Scheme 4, Stage 3, to a stirred suspension of 3-substituted-4-chloro-iodobenzene (1 eq) in degassed DMF (15 vol) was added bis-diborane (1.05 eq), Pd(OAc)2 (0.04 eq) and KOAc (3.0 eq). The reaction mixture was heated at 90° C. for 5 hrs under an atmosphere of N2. The reaction mixture was cooled to room temperature and filtered through celite then concentrated in vacuo to give crude product. Crude was used in the next step without further purification.

Referring to Reaction Scheme 4, Stage 4, to a stirred suspension of dichloropyrimidine (1 eq) in 1,4-dioxane (90 vol) was added boronic ester (1.0 eq) and Pd(PPh3)4 (0.03 eq). A 2M K2CO3 (3 eq) solution was added to the resulting mixture, which was heated at 90° C. for 16 hrs under an atmosphere of N2. The reaction mixture was cooled to room temperature and concentrated in vacuo. The residue was dissolved in EtOAc: water (1:1) (100 vol) and the resulting solution filtered through celite. The organic layer was separated and the aqueous layer further extracted with EtOAc (50 vol). The combined organic layers were washed with saturated aqueous NaCl (20 vol), dried over Na2SO4, filtered and the solvent removed in vacuo. The resulting residue was purified by flash column chromatography (eluent: [3:1] EtOAc:heptane) to afford the required target compound.

Referring to Reaction Scheme 4, Stage 5, 4-chloro-6-substituted-phenyl-pyrimidine (1 eq), PdCl2(dppf).DCM (0.05 eq) and triethylamine (2 eq) were suspended in degassed MeOH (50 vol) in a bomb fitted with a magnetic stirrer bar. The atmosphere in the reaction vessel was replaced with N2 by successive evacuation and charging with N2 gas (this process was repeated three times). The bomb was then flushed with CO by successive charging with CO and evacuation. The vessel was pressurised to 5 bar of CO and heated at 50° C. with stirring for 16 hours. The reaction vessel was allowed to cool to room temperature before venting CO and flushing with N2. The reaction mixture was concentrated in vacuo and the resulting residue dissolved in EtOAc (30 vol) and water (30 vol). The organic layer was separated, washed with saturated aqueous NaCl (15 vol), dried over Na2SO4, filtered and concentrated under reduced pressure. Purification by re-crystallisation using MeOH yielded the target compound.

Referring to Reaction Scheme 4, Stage 6, 6-substituted-phenyl-pyrimidine-4-carboxylic acid methyl ester (1 eq) was suspended in THF (20 vol), 2M NaOH (2.5 eq) and stirred at room temperature for 4 hours. Solvent (THF) was removed and reaction mixture was acidified with 2M HCl. Resulting solid was filtered and was with water to give desired product. Referring to Reaction Scheme 4, Stage 7, the required amide analogue was prepared following the procedure described in method B.

The following compounds were prepared substantially as described above.

| Structure | Molecular Weight | Mass Spec Result |
|---|---|---|
| 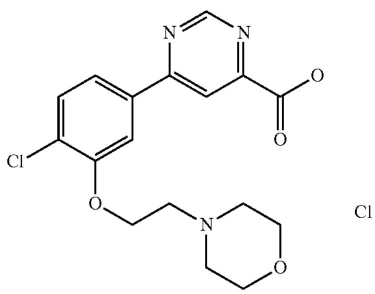 [SMILES: O=C(O)c1cc(-c2ccc(Cl)c(OCCN3CCOCC3)c2)ncn1 ; Cl] | 400.26 | [M + H]$^+$ = 364, 98% @ rt = 2.41 min |
| 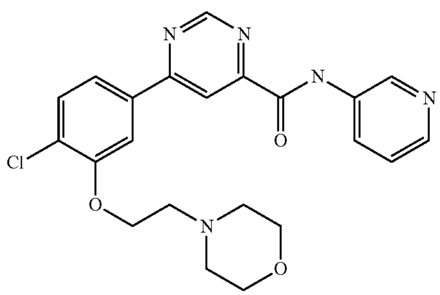 [SMILES: O=C(Nc1cccnc1)c1cc(-c2ccc(Cl)c(OCCN3CCOCC3)c2)ncn1] | 439.91 | [M + H]$^+$ = 440, 99% @ rt = 2.54 min |
| 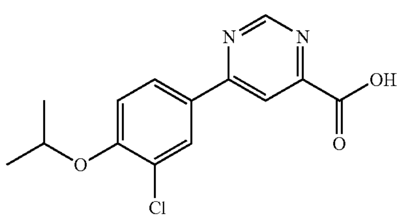 [SMILES: CC(C)Oc1ccc(-c2cc(C(=O)O)ncn2)cc1Cl] | 292.72 | [M + H]$^+$ = 293/295, 100% @ rt = 4.18 min |
| 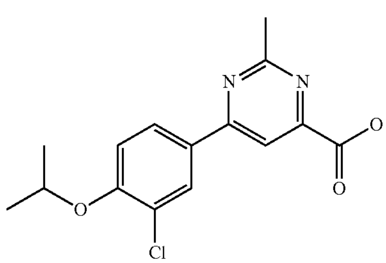 [SMILES: Cc1nc(C(=O)O)cc(-c2ccc(OC(C)C)c(Cl)c2)n1] | 306.75 | [M + H]$^+$ = 307/309, 100% @ rt = 4.10 min |

-continued

| Structure | Molecular Weight | Mass Spec Result |
|---|---|---|
| 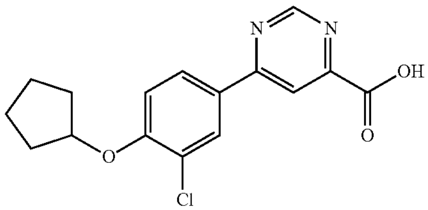 [SMILES: O=C(O)c1cc(-c2ccc(OC3CCCC3)c(Cl)c2)ncn1] | 318.76 | [M + H]⁺ = 319, 100% @ rt = 4.61 min |
| | 306.75 | [M + H]⁺ = 307/309, 100% @ rt = 4.37 min |
| | 306.75 | [M + H]⁺ = 307/309, 100% @ rt = 4.37 min |
| 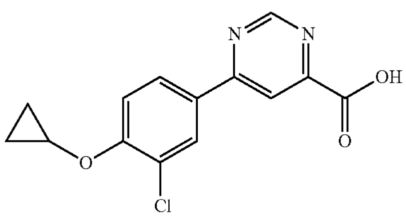 [SMILES: O=C(O)c1cc(-c2ccc(OC3CC3)c(Cl)c2)ncn1] | 290.71 | [M + H]⁺ = 291/293, 100% @ rt = 3.93 min |
| 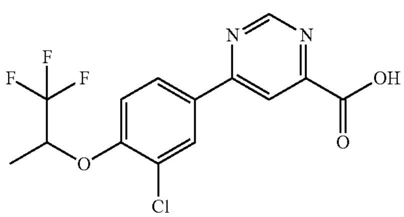 [SMILES: CC(Oc1ccc(-c2cc(C(=O)O)ncn2)cc1Cl)C(F)(F)F] | 346.69 | [M + H]⁺ = 347/349, 92/8% @ rt = 4.22 |
| 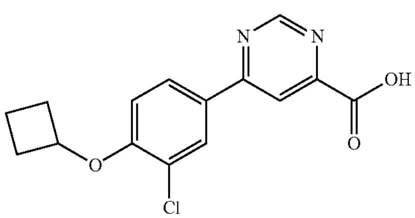 [SMILES: O=C(O)c1cc(-c2ccc(OC3CCC3)c(Cl)c2)ncn1] | 304.79 | [M + H]⁺ = 305/307, 100% @ rt = 4.20 min |
| 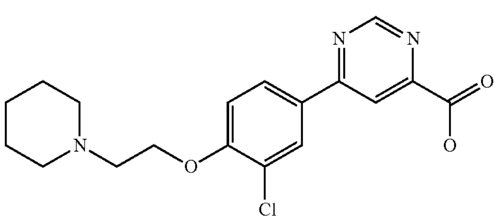 [SMILES: O=C(O)c1cc(-c2ccc(OCCN3CCCCC3)c(Cl)c2)ncn1] | 360.82 | [M + H]⁺ = 362/364, 100% @ rt = 2.55 min |

-continued

| Structure | Molecular Weight | Mass Spec Result |
|---|---|---|
| 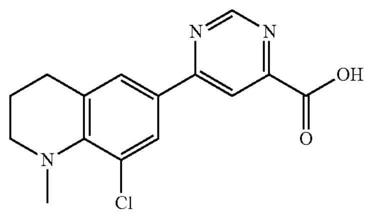 [SMILES: CN1CCCc2cc(-c3cc(C(=O)O)ncn3)cc(Cl)c21] | 303.75 | [M + H]+ = 304, 100% @ rt = 3.78 min |
| 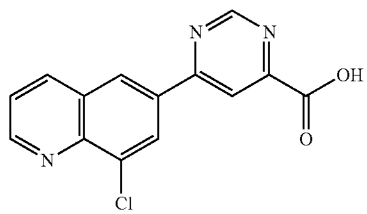 [SMILES: O=C(O)c1cc(-c2cc(Cl)c3ncccc3c2)ncn1] | 307.67 | [M + H]+ = 286/288, 99% @ rt = 3.26 min |
| 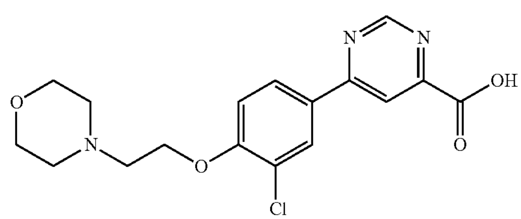 [SMILES: O=C(O)c1cc(-c2ccc(OCCN3CCOCC3)c(Cl)c2)ncn1] | 363.8 | [M + H]+ = 364/366 100% @ rt = 2.29 min |
| 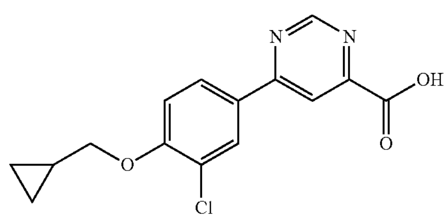 [SMILES: O=C(O)c1cc(-c2ccc(OCC3CC3)c(Cl)c2)ncn1] | 302.72 | [M − Na]− = 303/305 100% @ rt = 4.14 min |
| 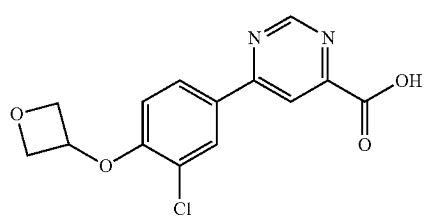 [SMILES: O=C(O)c1cc(-c2ccc(OC3COC3)c(Cl)c2)ncn1] | 305.89 | [M + H]+ = 307/309, 95% @ rt = 3.37 min |
| 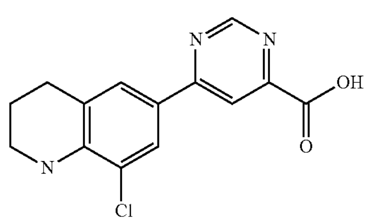 [SMILES: O=C(O)c1cc(-c2cc(Cl)c3c(c2)CCCN3)ncn1] | 289.71 | [M + H]+ = 290, 100% @ rt = 3.74 min |

Example 5

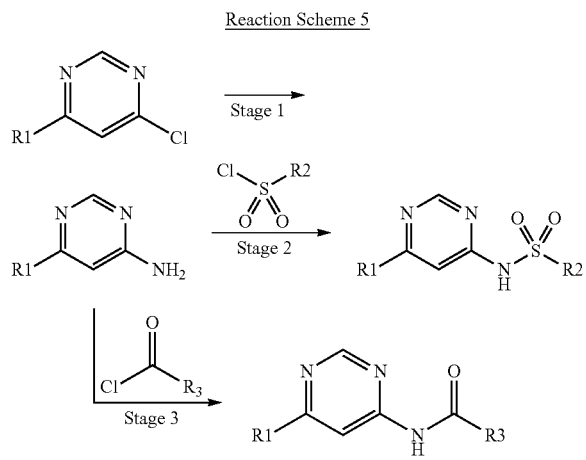

Reaction Scheme 5

Referring to Reaction Scheme 5, Stage 1, 4-(chloro-6-substituted)-phenyl-pyrimidine (1 eq) was suspended in 1,4-dioxane (3 vol) and ammonium hydroxide (6 vol) was added to the suspension. The reaction mixture was heated at 95° C. in a pressure tube for 16 hours with stirring. The reaction mixture was cooled to room temperature and the precipitate was filtered off and washed with water to yield the target compound.

Referring to Reaction Scheme 5, Stage 2, 6-(substituted-phenyl)-pyrimidin-4-ylamine (1 eq) was suspended in 1,4-dioxane (20 vol). Sodium hydride (6 eq) was added and the suspension was stirred for 1 hour at ambient temperature. 3-Pyridinesulfonyl chloride or benzenesulfonyl chloride (1.2 eq) were added and the reaction mixture was stirred at 80° C. for 24 hours. In the case of pyridinesulfonyl chloride derivative, the reaction was quenched by the addition of water and the solvent was removed in vacuo. Purification by flash column chromatography (eluent: [0:1 to 1:4] MeOH:EtOAc) afforded the target compound. In the case of benzenesulfonyl chloride derivative, acetonitrile/water was added and the solid filtered off. The filtrate was concentrated in vacuo and the residue was triturated in EtOAc to furnish the sodium salt as a powder. The sodium salt was then washed with a citric acid aqueous solution followed by water and dried to furnish the desired compound.

Referring to Reaction Scheme 5, Stage 3, 6-substituted-phenyl-pyrimidin-4-ylamine (1 eq) was suspended in 1,4-dioxane or DMF (20 vol). Sodium hydride (3 eq) was added and the suspension stirred for 10 to 60 minutes at room temperature. The appropriate acid chloride (1.5 eq) was added and the reaction mixture stirred at room temperature for 1 hour. The reaction was monitored by LCMS. If the reaction was not complete, sodium hydride (1 eq) was added to the reaction mixture, which was then heated at 50° C. for 16 hours. Upon completion, the reaction was quenched with water. If precipitation occurred, the precipitate was filtered and purified further by flash column chromatography using an appropriate eluent, if not the desired material was extracted with EtOAc. The organic layer was washed with saturated aqueous NaCl solution, dried with MgSO4, filtered and the solvent removed in vacuo. The desired compound was further purified either by trituration or prep HPLC when required.

The following compounds were prepared substantially as described above.

| Structure | Molecular Weight | Mass Spec Result |
|---|---|---|
| 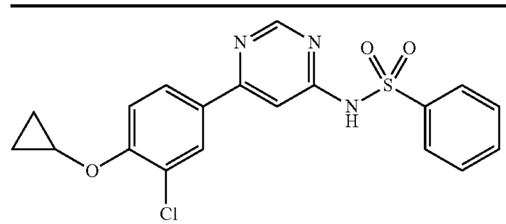 | 401.87 | [M + H]+ = 402, 99% @ rt = 4.53 min |
| 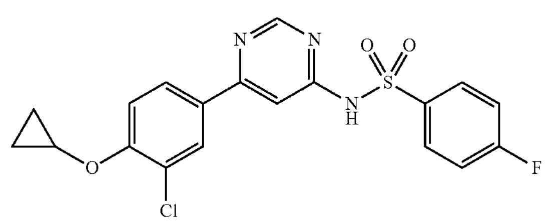 [SMILES: O=S(=O)(Nc1cc(-c2ccc(OC3CC3)c(Cl)c2)ncn1)c1ccc(F)cc1] | 419.87 | [M + H]+ = 420, 100% @ rt = 4.61 min |
| 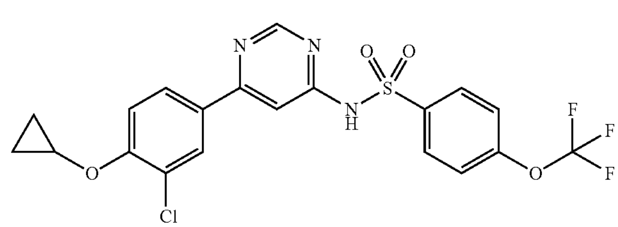 [SMILES: O=S(=O)(Nc1cc(-c2ccc(OC3CC3)c(Cl)c2)ncn1)c1ccc(OC(F)(F)F)cc1] | 485.87 | [M + H]+ = 486, 100% @ rt = 5.01 min |

| Structure | Molecular Weight | Mass Spec Result |
|---|---|---|
| (structure: 6-(3-chloro-4-cyclopropoxyphenyl)-N-(3-(trifluoromethoxy)phenylsulfonyl)pyrimidin-4-amine) | 485.87 | [M + H]+ = 487, 100% @ rt = 4.91 min |
| (structure: 6-(3-chloro-4-cyclopropoxyphenyl)-N-(2-fluorophenylsulfonyl)pyrimidin-4-amine) | 419.87 | [M + H]+ = 420, 99.5% @ rt = 4.51 min |
| (structure: 6-(3-chloro-4-cyclopropoxyphenyl)-N-(cyclopropylsulfonyl)pyrimidin-4-amine) | 365.84 | [M + H]+ = 366, 100% @ rt = 4.28 min |

Example 6

Reaction Scheme 6

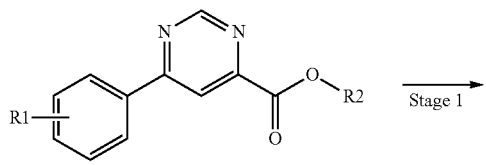

Stage 1

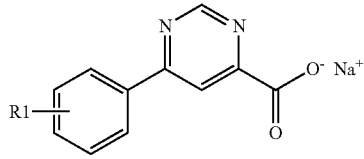

Referring to Reaction Scheme 6, Stage 1, to a stirred solution of 6-(3-chloro-phenyl)-pyrimidine-4-carboxylic acid (1 eq) or 6-(3,4-dichloro-phenyl)-pyrimidine-4-carboxylic acid methyl ester in THF (20 vol) was added dropwise a 1M NaOH solution. The mixture was stirred at ambient temperature and the resulting precipitate was filtered and washed with water/THF or with water then heptane to furnish the described salts.

| Structure | Molecular Weight | Mass Spec Result |
|---|---|---|
| (structure: sodium 6-(3-chloro-4-cyclopropoxyphenyl)pyrimidine-4-carboxylate) | 312.68 | [M + H]+ = 291/293, 100% @ rt = 3.97 min |

-continued
| Structure | Molecular Weight | Mass Spec Result |
|---|---|---|
| 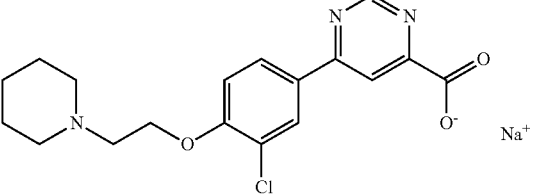 | 383.81 | [M + H]⁺ = 362/364, 100% @ rt = 2.55 min |
| 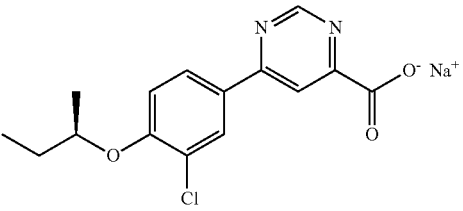 [SMILES: CC[C@@H](C)Oc1ccc(-c2cc(C(=O)[O-])ncn2)cc1Cl ; [Na+]] | 328.73 | [M + H]⁺ = 307/309, 100% @ rt = 4.35 min |
| 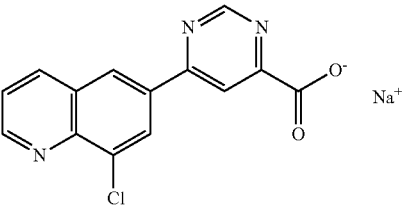 [SMILES: O=C([O-])c1cc(-c2cc(Cl)c3ncccc3c2)ncn1 ; [Na+]] | 307.67 | [M + H]+ = 286/288, 99% @ rt = 3.26 min |
| 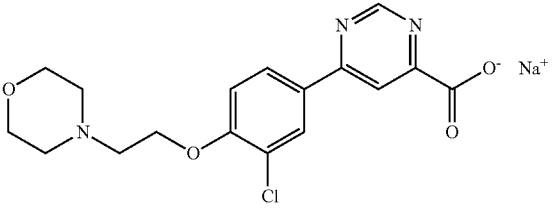 [SMILES: O=C([O-])c1cc(-c2ccc(OCCN3CCOCC3)c(Cl)c2)ncn1 ; [Na+]] | 385.8 | [M − Na + 2H]+ = 364/366 100% @ rt = 2.29 min |
| 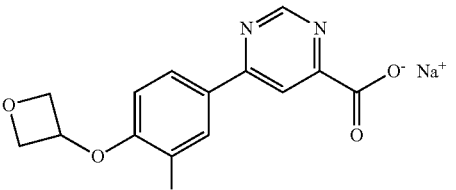 | 328.69 | [M + H]+ = 307/309, 87% @ rt = 3.37 min |

Example 7

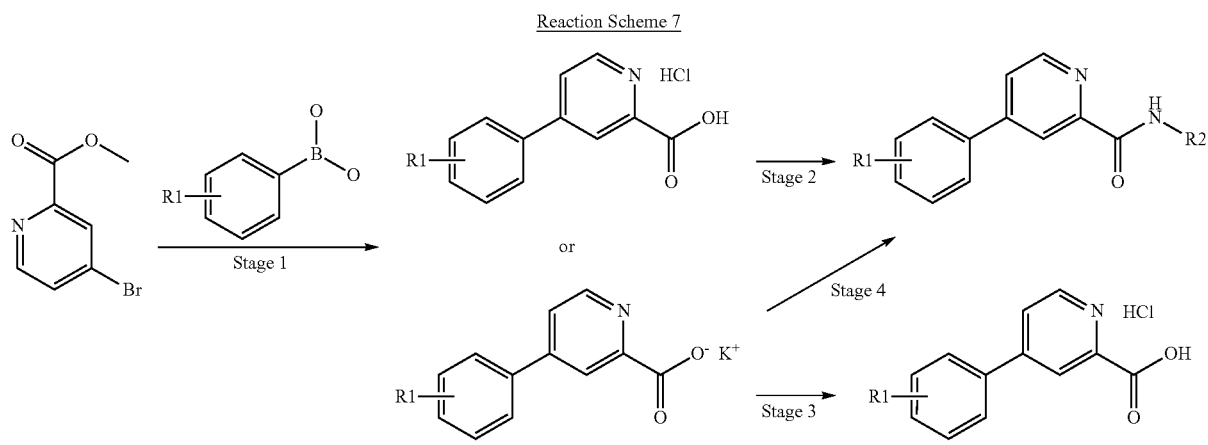

Reaction Scheme 7

Referring to Reaction Scheme 7, Stage 1, to a stirred suspension of 4-bromo-pyridine-2-carboxylic acid methyl ester (1 eq) in 1,4-dioxane (20 vol) was added the appropriate substituted phenyl boronic acid (1.1 eq) and Pd(PPh3)4 (0.05 eq). A 2M K2CO3 solution (7.5 vol) was added and the reaction mixture was heated at 90° C. with stirring for 16 hours under an atmosphere of N2. The reaction mixture was cooled to room temperature and the resulting precipitate was isolated by filtration to furnish the acid intermediate as the potassium salt, which was used without further purification in the stage. In the case of the 3-chlorophenyl analogue no precipitate was formed upon cooling, hence the solvent was removed in vacuo. The resulting residue was dissolved in EtOAc and water. Both phases were separated. EtOAc was removed in vacuo and the resulting residue was purified by flash column chromatography (eluent: [5:95] methanol:DCM) to furnish the desired 4-(3-chloro-phenyl)-pyridine-2-carboxylic acid methyl ester. The aqueous phase was acidified and the resulting precipitate was isolated by filtration and used as such in stage 2. Further purification was carried out by prep HPLC to furnish the required 4-(3-chloro-phenyl)-pyridine-2-carboxylic acid.

Referring to Reaction Scheme 7, Stage 2, the required amide analogues were prepared following the procedure described in method A from 4-(3-chloro-phenyl)-pyridine-2-carboxylic acid, hydrochloride salt and were purified by trituration in acetonitrile/water (1/1) or in water followed by heptane.

Referring to Reaction Scheme 7, Stage 3, the potassium salt isolated in stage 1 was suspended in HCl (2M) and stirred at ambient temperature for 2 hours. The solid was filtered and washed with water to furnish the desired target compound.

Referring to Reaction Scheme 7, Stage 4, the required amide analogues were prepared following the procedure described in method A from 4-(substituted-phenyl)-pyridine-2-carboxylic acid potassium salt and were purified by trituration in acetonitrile/water (1/1) or in water followed by heptane.

The following compounds were prepared substantially as described above.

| Structure | Molecular Weight | Mass Spec Result |
|---|---|---|
| 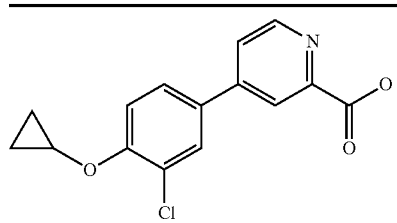 | 289.72 | [M + H]$^+$ = 290/292, 98% @ rt = 3.31 min |
| 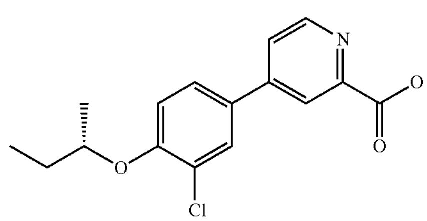 [SMILES: CC[C@H](C)Oc1ccc(-c2ccnc(C(=O)O)c2)cc1Cl] | 305.76 | [M + H]$^+$ = 306/308, 99% @ rt = 3.73 min |

-continued

| Structure | Molecular Weight | Mass Spec Result |
|---|---|---|
| 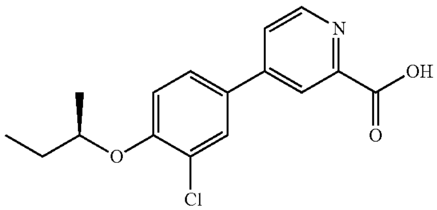 [SMILES: CC[C@@H](C)Oc1ccc(-c2ccnc(C(=O)O)c2)cc1Cl] | 305.76 | [M + H]+ 306/308, 99% @ rt = 3.71 min |
| 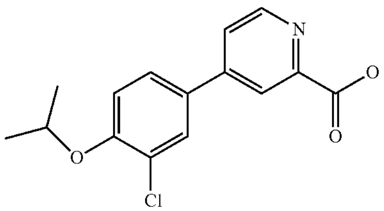 [SMILES: CC(C)Oc1ccc(-c2ccnc(C(=O)O)c2)cc1Cl] | 291.74 | [M + H]+ = 292/294, 100% @ rt = 3.44 min |

Example 8

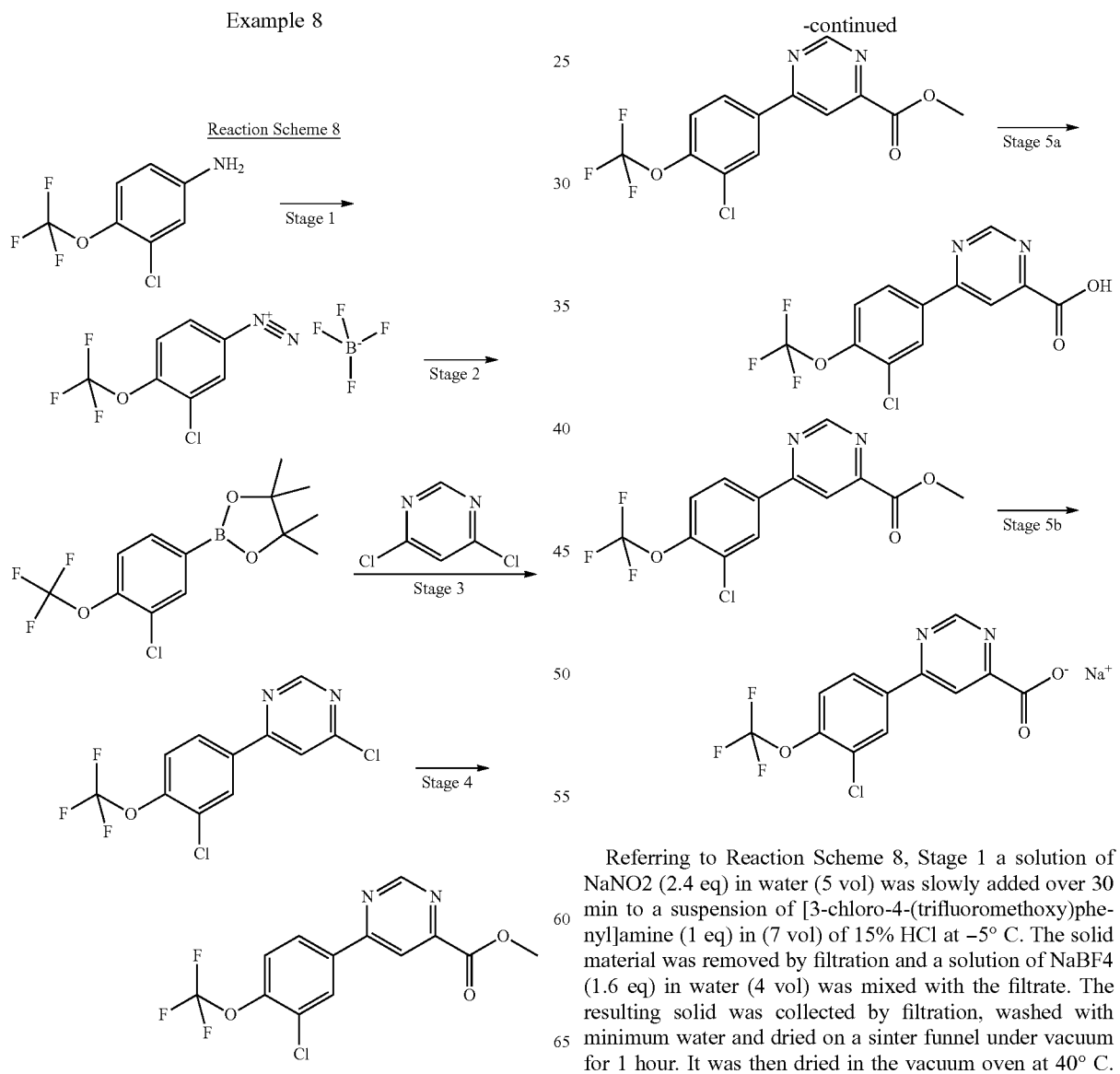

Reaction Scheme 8

Referring to Reaction Scheme 8, Stage 1 a solution of NaNO2 (2.4 eq) in water (5 vol) was slowly added over 30 min to a suspension of [3-chloro-4-(trifluoromethoxy)phenyl]amine (1 eq) in (7 vol) of 15% HCl at −5° C. The solid material was removed by filtration and a solution of NaBF4 (1.6 eq) in water (4 vol) was mixed with the filtrate. The resulting solid was collected by filtration, washed with minimum water and dried on a sinter funnel under vacuum for 1 hour. It was then dried in the vacuum oven at 40° C. until constant weight to give the required product.

Referring to Reaction Scheme 8, Stage 2, 3-chloro-4-(trifluoromethoxy)benzene-1-diazonium tetrafluoroboranide (1 eq) was mixed with bis(pinacolato) diboron (1.05 eq) in a flask cooled by an ice bath. MeOH (8 vol) was added and the mixture was de-gassed with nitrogen for 10 minutes before PdCl2(dppf)2.DCM (0.025 eq) was added. The mixture was stirred at room temperature overnight before analysis by LCMS. The reaction was evaporated to dryness, re-dissolved in DCM, dry loaded onto silica and purified by dry flash chromatography running a slow gradient from 0-20% EtOAc in heptane. Clean fractions were combined and evaporated to dryness to give the required product as an oil.

Referring to Reaction Scheme 8, Stage 3, 4,6-dichloro-pyrimidine (1 eq) and 2-[3-chloro-4-(trifluoromethoxy)phenyl]-4,4,5,5-tetramethyl-1,3,2-dioxaborolane (0.7 eq) were dissolved in dioxane (12 vol) at room temperature and 2M potassium carbonate (2 eq) was added. The solution was degassed with nitrogen for 5 minutes. Pd(PPh3)4 (0.05 eq) was added and the reaction was stirred at 90° C. for 2 hours before analysis by LCMS. The reaction was cooled to room temperature and the solvent was evaporated. DCM was added and the organic layer was washed with water, brine and dried using MgSO4. The solvent was evaporated to dryness to give an oil which was purified by dry-flash chromatography eluting with 0-6% EtOAc in heptane. The resulting oil was dried in the vacuum oven at 40° C. to give the required product.

Referring to Reaction Scheme 8, Stage 4, 4-Chloro-6-(3-chloro-4-trifluoromethoxy-phenyl)-pyrimidine (1 eq), and triethylamine (2 eq) were dissolved in MeOH and degassed for 5 minutes with nitrogen. Pd(dppf)2Cl2.DCM (0.05 eq) was added and the reaction was sealed inside a 500 ml bomb. The bomb was charged with CO (5 bar) and heated at 50° C. overnight before analysis by LCMS. The reaction was cooled to room temperature and the solvent evaporated. The residue was re-dissolved in EtOAc and washed with water, brine and dried using MgSO4. The solvent was evaporated and the resulting solid purified by dry flash chromatography eluting with 30-40% EtOAc in heptane to give the required product.

Referring to Reaction Scheme 8, Stage 5a, 6-(3-Chloro-4-trifluoromethoxy-phenyl)-pyrimidine-4-carboxylic acid methyl ester was dissolved in THF (16 vol) and 2M NaOH (2 eq) was added. The reaction mixture was allowed to stir at room temperature for 17 hours. Water (32 vol) was added and the mixture extracted with EtOAc (2×32 vol). 2 M HCl (2 eq) was added and the solution extracted with EtOAc (3×32 vol). The combined organic layers were dried over MgSO4 and the solvent removed to dryness. The crude compound was re-crystallised from acetonitrile (20 vol), filtered and dried in a vacuum oven at 40° C. to give the desired target 6-(3-chloro-4-trifluoromethoxy-phenyl)-pyrimidine-4-carboxylic acid.

Referring to Reaction Scheme 8, Stage 5b, 6-(3-Chloro-4-trifluoromethoxy-phenyl)-pyrimidine-4-carboxylic acid methyl ester was dissolved in THF. 2M NaOH (2 eq) was added and the reaction was stirred at room temperature for 12 hours before analysis by LCMS. The reaction was evaporated to dryness and the resulting solid was washed with water and diethyl ether. The solid was dried in a vacuum oven at 40° C. to give the target compound 6-(3-chloro-4-trifluoromethoxy-phenyl)-pyrimidine-4-carboxylic acid as a sodium salt.

The following compounds were prepared substantially as described above.

| Structure | Molecular Weight | Mass Spec Result |
|---|---|---|
| ![structure] | 318.64 | $[M + H]^+$ = 319/321, 74% @ rt = 4.32 min |
| ![structure] | 340.62 | $[M + H]^+$ = 319/321, 100% @ rt = 4.19 min |

Example 9

Reaction Scheme 9

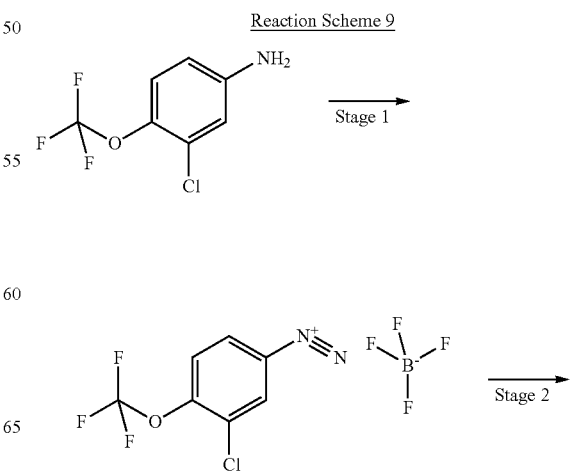

Stage 1

Stage 2

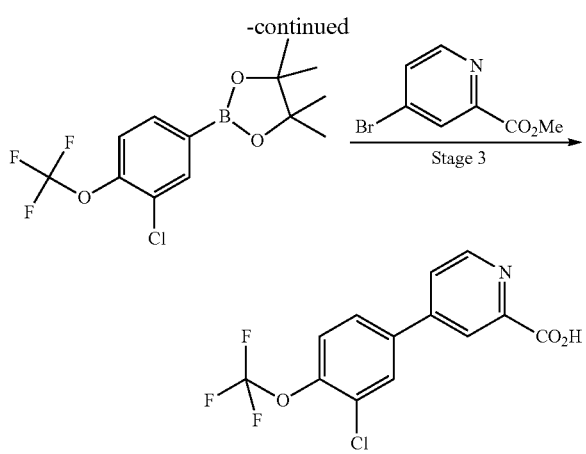

Referring to Reaction Scheme 9, Stage 1 a solution of NaNO2 (2.4 eq) in water (5 vol) was slowly added over 30 min to a suspension of [3-chloro-4-(trifluoromethoxy)phenyl]amine (1 eq) in (7 vol) of 15% HCl at −5° C. The solid material was removed by filtration and a solution of NaBF4 (1.6 eq) in water (4 vol) was mixed with the filtrate. The resulting solid was collected by filtration, washed with minimum water and dried on a sinter funnel under vacuum for 1 hour. It was then dried in the vacuum oven at 40° C. until constant weight to give the required product.

Referring to Reaction Scheme 9, Stage 2, 3-chloro-4-(trifluoromethoxy)benzene-1-diazonium tetrafluoroboranide (1 eq) was mixed with bis(pinacolato) diboron (1.05 eq) in a flask cooled by an ice bath. MeOH (8 vol) was added and the mixture was de-gassed with nitrogen for 10 minutes before PdCl2(dppf)2.DCM (0.025 eq) was added. The mixture was stirred at room temperature overnight before analysis by LCMS. The reaction was evaporated to dryness, re-dissolved in DCM, dry loaded onto silica and purified by dry flash chromatography running a slow gradient from 0-20% EtOAc in heptane. Clean fractions were combined and evaporated to dryness to give the required product as an oil.

Referring to Reaction Scheme 9, Stage 3, to a stirred suspension of 4-bromo-pyridine-2-carboxylic acid methyl ester (1 eq) in 1,4-dioxane (20 vol) was added the appropriate substituted phenyl boronic acid (1.1 eq) and Pd(PPh3)4 (0.05 eq). A 2M K2CO3 solution (7.5 vol) was added and the reaction mixture was heated at 90° C. with stirring for 16 hours under an atmosphere of N2. The reaction mixture was cooled to room temperature and the resulting precipitate was isolated by filtration to furnish the acid product as the potassium salt which was suspended in HCl (2M) and stirred at ambient temperature for 2 hours. The solid was filtered and washed with water to furnish the desired target compound.

The following compounds were prepared substantially as described above.

| Structure | Molecular Weight | Mass Spec Result |
|---|---|---|
| 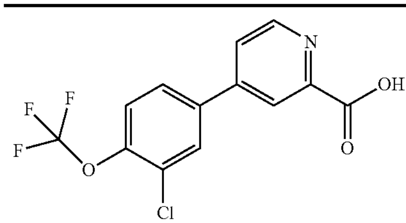 | 317.65 | $[M + H]^+$ = 317, 100% @ rt = 3.76 min |

Example 10

Reaction Scheme 10

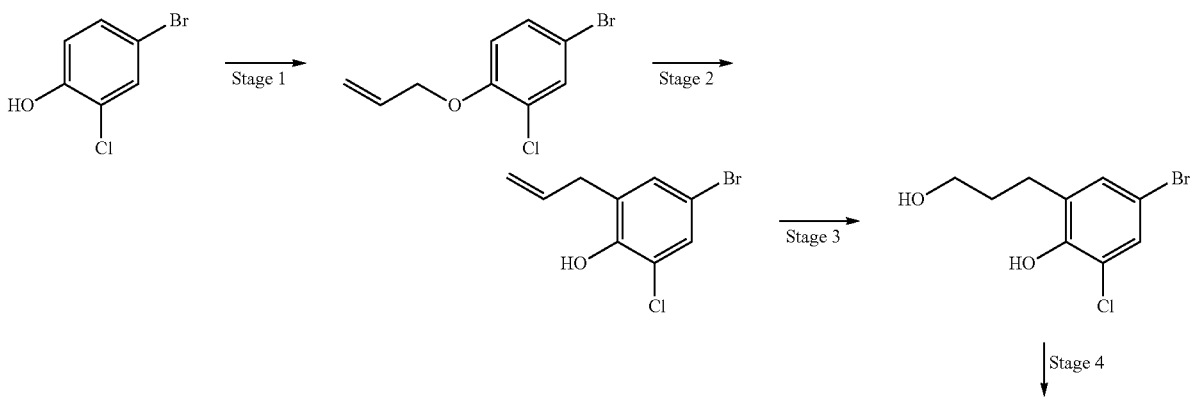

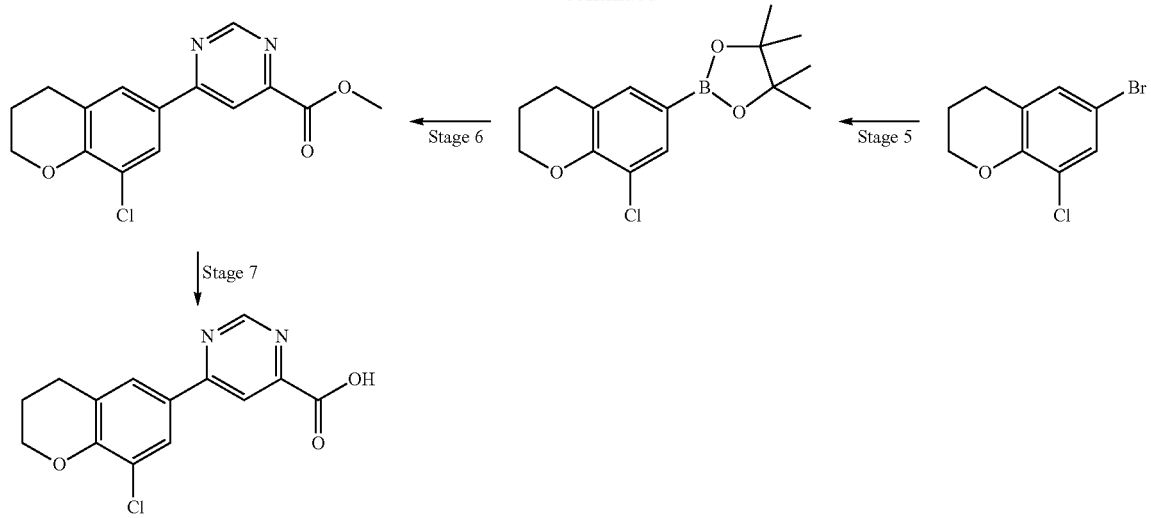

Referring to Reaction Scheme 10, Stage 1. Sodium hydride (1.1 eq) was added portion wise to a cool (0° C.), stirred solution of 4-bromo-2-chlorophenol (1.0 eq) in DMF (6 vol) and the mixture stirred at this temperature under a nitrogen atmosphere for 30 minutes. After this time, 3-bromoprop-1-ene (1.1 eq) was added dropwise and the reaction mixture was allowed to warm to room temperature before being stirred at this temperature overnight. After this time, the reaction mixture was poured onto ice-water (10 vol), the mixture was extracted with ethyl acetate (3×), the organic layers were combined, washed with brine (5 vol), dried (MgSO4), filtered and concentrated. The resulting residue was purified by flash column chromatography (elution: 20% ethyl acetate, 80% heptane) to give the desired compound as a yellow gum.

Referring to Reaction Scheme 10, Stage 2. 1-Allyloxy-4-bromo-2-chloro benzene (1 eq) was suspended in mesitylene (12 vol) and the mixture heated to 160° C. and stirred at this temperature overnight. After this time, the reaction mixture was cooled to room temperature and concentrated. The resulting residue was purified using a Biotage Isolera (340 g silica column eluting with a gradient from heptane to 100% DCM) to give the desired compound as a yellow oil.

Referring to Reaction Scheme 10, Stage 3. Borane (1M solution in THF, 1 eq) was added drop wise to a stirred solution of 2-allyl-4-bromo-6-chloro-phenol (1 eq) in THF (10 vol) and the reaction mixture was stirred at room temperature under a nitrogen atmosphere for 4 hours. After this time, the reaction mixture was quenched by the sequential addition of water (1 eq), NaOH (1 eq) and hydrogen peroxide (1 eq) and the mixture stirred at room temperature for a further 2 hours. The resulting mixture was partitioned between diethyl ether (5 vol) and water (5 vol). The organic layer was separated, washed with brine (2 vol), dried (MgSO4), filtered and to give the desired compound as a colourless gum.

Referring to Reaction Scheme 10, Stage 3. Diethyl diazene-1,2-dicarboxylate (1 eq) was added dropwise to a stirred solution of triphenyl phosphane (1 eq) and 4-bromo-2-chloro-6-(3-hydroxy-propyl)-phenol (1 eq) and the reaction mixture was stirred at room temperature under a nitrogen atmosphere overnight After this time, the reaction mixture was concentrated and purified using a Biotage Isolera (50 g silica column eluting with a gradient from 0% heptane to 20% ethyl acetate/80% heptane) to give the desired compound as a pale yellow oil.

Referring to Reaction Scheme 10, Stage 4. Bis-pinacol borane (1.5 eq) was added in one portion to a cool (0° C.), stirred solution of 6-bromo-8-chloro-chroman (1.0 eq) and potassium acetate (3.5 eq) in DMSO (5 vol). The mixture was degassed with nitrogen for 5 minutes, after which time Pd(dppf)2Cl2 (0.1 eq) was added in one portion, the mixture was allowed to warm to room temperature and was stirred at this temperature under a nitrogen atmosphere for 1 hour. After this time the inorganic precipitate was removed by filtration and the filtrate was concentrated. The resulting residue was purified using a Biotage Isolera (50 g silica column eluting with a gradient from 0% heptane to 40% DCM/60% heptane) to give the desired compound as a pale yellow oil.

Referring to Reaction Scheme 10, Stage 5. Tripotassium phosphate (2 eq) was added in one portion to a stirred solution of 8-chloro-6-(4,4,5,5-tetramethyl-[1,3,2]dioxaborolan-2-yl)-chroman (1 eq) and methyl 4-bromopyridine-2-carboxylate (2 eq) in DMF (10 vol). The mixture was degassed with nitrogen for 5 minutes, after which time Pd(dppf)2Cl2 (0.2 eq) was added in one portion, the mixture was then heated to 60° C. and stirred at this temperature for 16 hours under a nitrogen atmosphere. After this time the reaction mixture was cooled to room temperature and partitioned between ethyl acetate (5 vol) and water (5 vol). The organic layer was separated, washed sequentially with water (5 vol) then brine (5 vol) before being dried (MgSO4), filtered and concentrated. The resulting residue was purified using a Biotage Isolera (100 g silica column eluting with a gradient from 0% heptane to 80% DCM/20% heptane) to give the desired compound as a white solid.

Referring to Reaction Scheme 10, Stage 5. 2M NaOH (4 eq) was added in one portion to a stirred solution of 6-(8-chloro-chroman-6-yl)-pyrimidine-4-carboxylic acid methyl ester (1 eq) in ethanol (1 vol) and the mixture was stirred at room temperature for 2 hours. After this time the reaction mixture was diluted with water and the ethanol removed under reduced pressure. The remaining solution was acidified to pH 1 with 1M HCl and the resulting precipitate was collected by filtration, washed with water (5 vol) and TBME (5 vol) and dried in a vacuum oven at 40° C. overnight to afford the desired compound as a white solid.

The following compounds were prepared substantially as described above.

| Structure | Molecular Weight | Mass Spec Result |
|---|---|---|
| 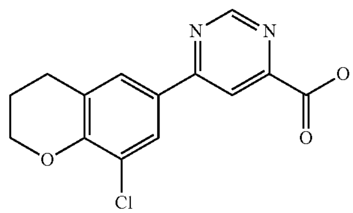 [SMILES: O=C(O)c1cc(-c2cc(Cl)c3c(c2)CCCO3)ncn1] | 290.71 | [M + H]+ = 291, 100% @ rt = 3.71 min |

Example 11

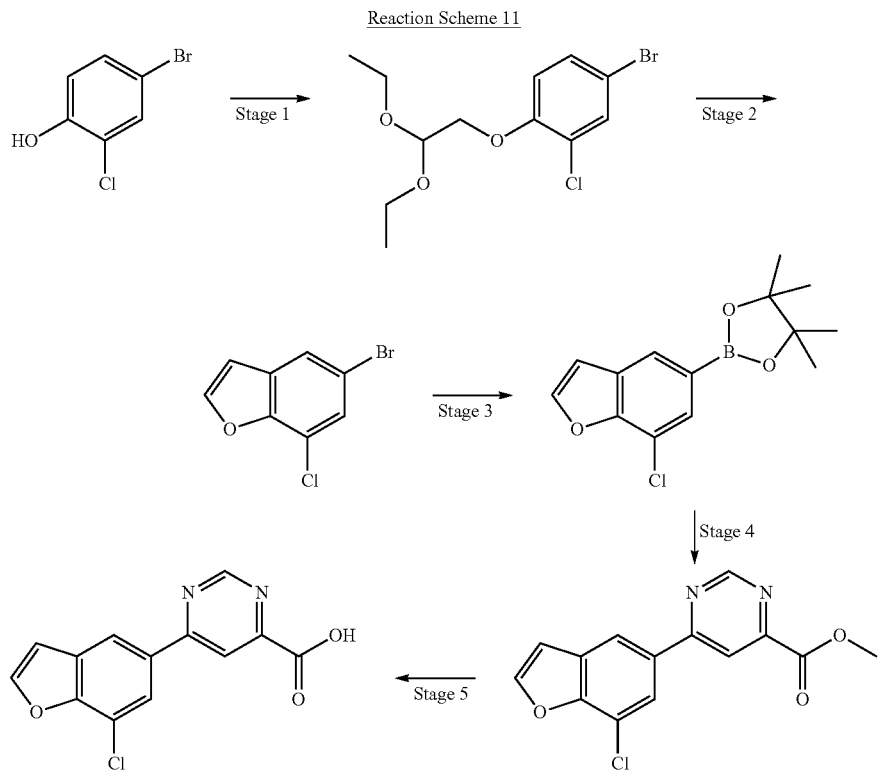

Reaction Scheme 11

Referring to Reaction Scheme 11, Stage 1. Potassium carbonate (2 eq) was added portion wise to a stirred solution of 4-bromo-2-chlorophenol (1 eq) and bromoacetaldehyde diethyl acetal (1.5 eq) in DMF (6 vol) and the mixture was heated to 140° C. and heated at this temperature under a nitrogen atmosphere for 3 hours. After this time the reaction mixture was cooled to room temperature and concentrated. The resulting residue was partitioned between ethyl acetate (20 vol) and water (5 vol), the organic layer was separated, dried (MgSO4), filtered and concentrated. The resulting residue was purified using a Biotage Isolera (340 g silica column eluting with a gradient from 0% DCM to 60% DCM/40% heptane) to afford the desired compound as a colourless oil.

Referring to Reaction Scheme 11, Stage 2. 4-Bromo-2-chloro-1-(2,2-diethoxy-ethoxy)-benzene (1 eq) was added portion wise as a solution in toluene (5 vol) to polyphosphonic acid (8 eq)) at 0° C. The resulting suspension was allowed to warm to room temperature before being heated to reflux and stirred for 1 hour. After this time the mixture was cooled to room temperature and partitioned between water (10 vol) and ethyl acetate (30 vol). The resulting residue was partitioned between ethyl acetate (30 vol) and water (5 vol), the organic layer was separated, dried (MgSO4), filtered and concentrated. The resulting residue was purified using a Biotage Isolera (340 g silica column eluting with 100% heptane) to afford the desired compound as a white solid.

Referring to Reaction Scheme 11, Stage 3. Potassium acetate (3 eq) was added in one portion to a stirred solution of 5-bromo-7-chloro-benzofuran (1 eq) and bis-pinacol borane (1.1 eq) in DMF (3 vol). The mixture was degassed with nitrogen for 5 minutes, after which time Pd(dppf)2Cl2 (0.3 eq) was added in one portion, the mixture was then heated to 80° C. and stirred at this temperature for 18 hours under a nitrogen atmosphere. After this time the reaction mixture was cooled to room temperature and partitioned between ethyl acetate (20 vol) and water (10 vol). The biphasic suspension was filtered through glass fiber filter paper and the organic layer was separated, washed sequentially with water (3×) before being dried (MgSO4), filtered and concentrated. The resulting residue was purified using a Biotage Isolera (100 g silica column eluting with 100% heptane to 50% DCM/50% heptane) to afford the desired compound as a white solid.

Referring to Reaction Scheme 11, Stage 4. Tripotassium phosphate (1.4 eq) was added in one portion to a stirred solution of, 7-chloro-5-(4,4,5,5-tetramethyl-[1,3,2]dioxaborolan-2-yl)-benzofuran (1 eq) and methyl 6-chloropyrimidine-4-carboxylate (2 eq) in DMF (4 vol). The mixture was degassed with nitrogen for 5 minutes, after which time Pd(dppf)2Cl2 (0.2 eq) was added in one portion, the mixture was then heated to 60° C. and stirred at this temperature for 16 hours under a nitrogen atmosphere. After this time the reaction mixture was cooled to room temperature and partitioned between ethyl acetate (20 vol) and water (10 vol). The organic layer was separated, washed sequentially with water (10 vol) then brine (10 vol) before being dried (MgSO4), filtered and concentrated. The resulting residue was purified using a Biotage Isolera (50 g silica column eluting with 100% heptane to 20% ethyl acetate/50% heptane) to afford the desired compound as a white solid.

Referring to Reaction Scheme 11, Stage 5. NaOH (1.5 eq) was added in one portion to a stirred solution of 6-(7-chloro-benzofuran-5-yl)-pyrimidine-4-carboxylic acid methyl ester (1.0 eq) in THF (8 vol) and the mixture was stirred at room temperature for 16 hours. After this time, the resulting precipitate was collected by filtration, washed with water (1 vol) and DCM (2 vol) before being dried under vacuum. This solid was then suspended in HCl (2M solution, 6 vol) and acetonitrile (6 vol), heated to 80° C. until complete dissolution then cooled to room temperature. The acetonitrile was removed under reduced pressure and the solid precipitate was collected by filtration, washed with water (1 vol) before being dried in a vacuum over overnight to give the hydrochloride salt of the desired compound as a white solid.

The following compounds were prepared substantially as described above.

| Structure | Molecular Weight | Mass Spec Result |
|---|---|---|
| (structure shown) | 274.67 | [M + H]+ = 275/277, 98% @ rt = 3.70 min |

Example 12

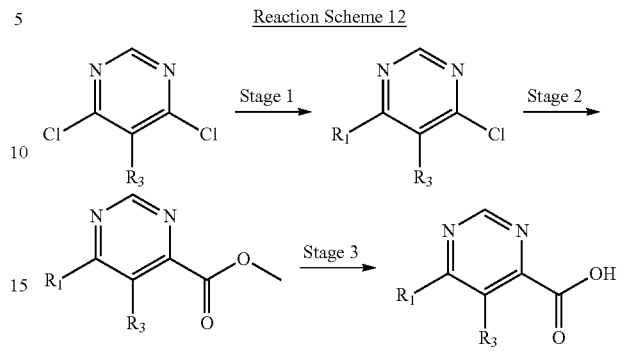

Reaction Scheme 12

Referring to Reaction Scheme 12, Stage 1. Potassium carbonate (2M solution, 52.0 ml, 104.0 mmol) was added in one portion to a stirred solution of 3,4-dichlorophenyl boronic acid (6.9 g, 37.0 mmol) and 4,6-dichloro-5-methyl pyrimidine (8.5 g, 52.0 mmol) in dioxane (150 ml). The mixture was degassed with nitrogen for 5 minutes, after which time palladium tetrakis triphenylphosphine (3.0 g, 3.0 mmol) was added in one portion, the mixture was then heated to 90° C. and stirred at this temperature for 16 hours under a nitrogen atmosphere. After this time the reaction mixture was cooled to room temperature and concentrated. The resulting residue was dissolved in DCM (500 ml), washed sequentially with water (500 ml) then brine (500 ml) before being dried (MgSO4), filtered and concentrated. The resulting residue was purified by flash column chromatography (elution: 6% EtOAc, 94% Heptane) to give the desired compound (6.05 g, 42% yield) as a white solid. δH (500 MHz, DMSO) 8.91-9.00 (1H, m) 7.88-7.96 (1H, m) 7.76-7.88 (1H, m) 7.58-7.69 (1H, m) 2.36 (3H, s). Tr=2.30 min m/z (ES+) (M+H+) 275, 277.

Referring to Reaction Scheme 12, Stage 2. Triethylamine (6.1 ml, 44.0 mmol) was added in one portion to a calorimeter containing a stirred solution of 4-chloro-6-(3,4-di-chloro-phenyl)-5-methyl-pyrimidine (5.95 g, 22.0 mmol) in methanol (80 ml). The mixture was degassed with nitrogen for 5 minutes, after which time Pd(dppf)2Cl2 (0.9 g, 1.0 mmol) was added in one portion, the calorimeter was sealed, pressurised with carbon monoxide (5 bar) and was heated to 50° C. overnight. After this time the reaction mixture was cooled to room temperature, diluted with methanol and concentrated. The resulting residue was dissolved in DCM (300 ml) and washed sequentially with water (250 ml) and brine (250 ml). The organic layer was separated, dried (MgSO4), filtered, concentrated and the resulting residue purified by flash column chromatography (elution: 40% EtOAc, 60% heptane) to give the desired compound (5.2 g, 80% yield) as a white solid. δH (500 MHz, DMSO) 9.19 (1H, s) 7.92-7.97 (1H, m) 7.79-7.85 (1H, m) 7.63-7.70 (1H, m) 3.95 (3H, s) 2.30-2.42 (3H, m). Tr=2.10 min m/z (ES+) (M+H+) 297, 299.

Referring to Reaction Scheme 12, Stage 3. NaOH (2M solution, 1.1 ml, 2.0 mmol) was added in one portion to a stirred solution of 6-(3,4-dichloro-phenyl)-5-methyl-pyrimidine-4-carboxylic acid methyl ester (0.32 g, 1.0 mmol) in THF (10 ml) and the mixture was stirred at room temperature for 16 hours. After this time, the resulting precipitate was collected by filtration, washed with water (1 ml) and DCM (20 ml) before being dried under vacuum. This solid was then suspended in HCl (2M solution, 60 ml) and acetonitrile (60 ml), heated to 80° C. until complete dissolution then cooled to room temperature. The acetonitrile was removed under reduced pressure and the solid precipitate was collected by filtration, washed with water (10 ml) before being dried in a vacuum over overnight to give the hydrochloride salt of the desired compound (0.22 g, 75% yield) as a white solid.

The following compounds were prepared substantially as described above.

| Structure | Molecular Weight | Mass Spec Result |
|---|---|---|
| 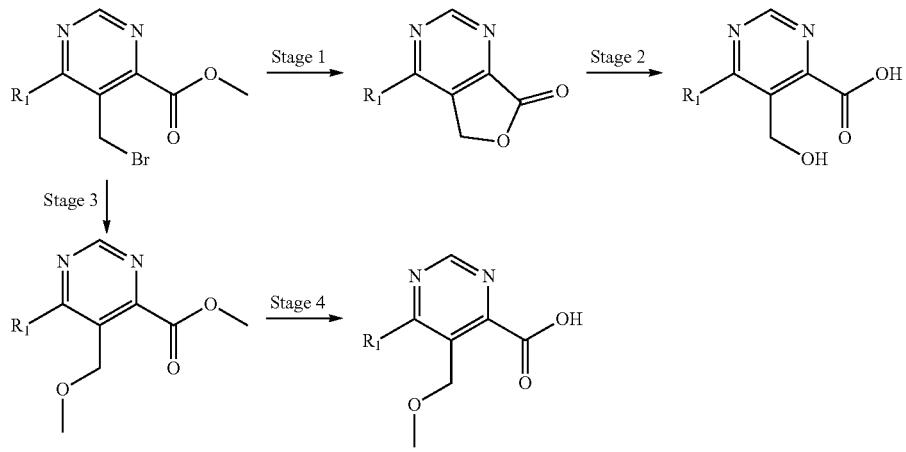 | 304.72 | [M + H]+ = 305/307, 100% @ rt = 3.64 min |

Example 13

Reaction Scheme 13

Referring to Reaction Scheme 13, Stage 1. Sodium bicarbonate (0.46 g, 5.0 mmol) was added in one portion to a stirred solution of 5-bromomethyl-6-(3,4-dichloro-phenyl)-pyrimidine-4-carboxylic acid methyl ester (0.24 g, 0.64 mmol) in DMSO (5 ml), and the mixture was stirred at room temperature under a nitrogen atmosphere for 20 hours. After this time the mixture was partitioned between ethyl acetate (20 ml) and water (20 ml), the organic layer was separated and the aqueous layer extracted with ethyl acetate (2×20 ml). The organic layers were combined, dried (MgSO4), filtered, concentrated and the resulting residue was triturated with diethyl ether. The resulting precipitate was collected by filtration and dried under vacuum to give the desired compound (0.08 g, 45% yield) as an orange solid.

Referring to Reaction Scheme 13, Stage 2. Sodium methoxide (0.02 g, 0.36 mmol) was added in one portion to a stirred solution of 4-(3,4-dichloro-phenyl)-5H-furo[3,4-d]pyrimidin-7-one (0.05 g, 0.18 mmol) in methanol (5 ml), and the mixture was stirred at room temperature under a nitrogen atmosphere for 20 hours. After this time, sodium hydroxide (2M solution, 0.05 ml, 0.89 mmol) was added and the mixture was heated to 70° C. and stirred at this temperature for a further 4 hours. After this time the reaction mixture was cooled to room temperature and the resulting precipitate was collected by filtration, washed with methanol (5 ml) and dried under vacuum to give the desired compound (0.01 g, 5% yield) as an off-white solid.

Referring to Reaction Scheme 13, Stage 3. Sodium methoxide (0.03 g, 0.53 mmol) was added in one portion to a stirred solution of 5-bromomethyl-6-(3,4-dichloro-phenyl)-pyrimidine-4-carboxylic acid methyl ester (0.1 g, 0.26 mmol) in methanol (5 ml), and the mixture was stirred at room temperature under a nitrogen atmosphere for 20 hours. After this time the mixture was concentrated and the resulting residue taken up in DCM (10 ml). The solution was washed consecutively with water (2×50 ml) and brine (2×50 ml), before being separated, dried (MgSO4), filtered and concentrated. The resulting residue was purified by flash column chromatography (elution: 100% DCM to 99% DCM: 1% Methanol) to give the desired compound (0.02 g, 20% yield) as a white solid. Tr=2.11 min m/z (ES+) (M+H+) 327, 329.

Referring to Reaction Scheme 13, Stage 4. Sodium hydroxide (0.05 ml, 0.1 mmol) was added in one portion to a stirred solution of methyl 6-(3,4-dichlorophenyl)-5-(methoxymethyl)pyrimidine-4-carboxylate (0.1 g, 0.26 mmol) in THF (5 ml) and the mixture was stirred at room temperature under a nitrogen atmosphere for 20 hours. After this time the resulting precipitate was collected by filtration, washed with water (1 ml) and dried under vacuum to give the desired compound (0.004 g, 15% yield) as a white solid.

The following compounds were prepared substantially as described above.

| Structure | Molecular Weight | Mass Spec Result |
|---|---|---|
| 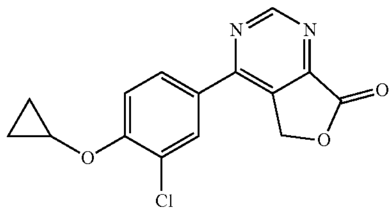 [SMILES: O=C1OCc2c1ncnc2-c1ccc(OC2CC2)c(Cl)c1] | 302.72 | [M + H]+ = 303/305, 100% @ rt = 4.20 min |
| 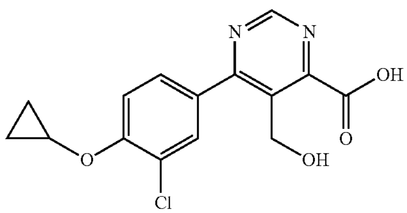 [SMILES: O=C(O)c1ncnc(-c2ccc(OC3CC3)c(Cl)c2)c1CO] | 320.72 | [M + H]+ = 321/323, 100% @ rt = 3.29 min |
| 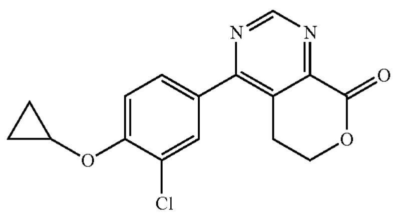 [SMILES: O=C1OCCc2c1ncnc2-c1ccc(OC2CC2)c(Cl)c1] | 316.75 | [M + H]+ = 317/319, 100% @ rt = 3.89 min |

Example 14

Reaction Scheme 14

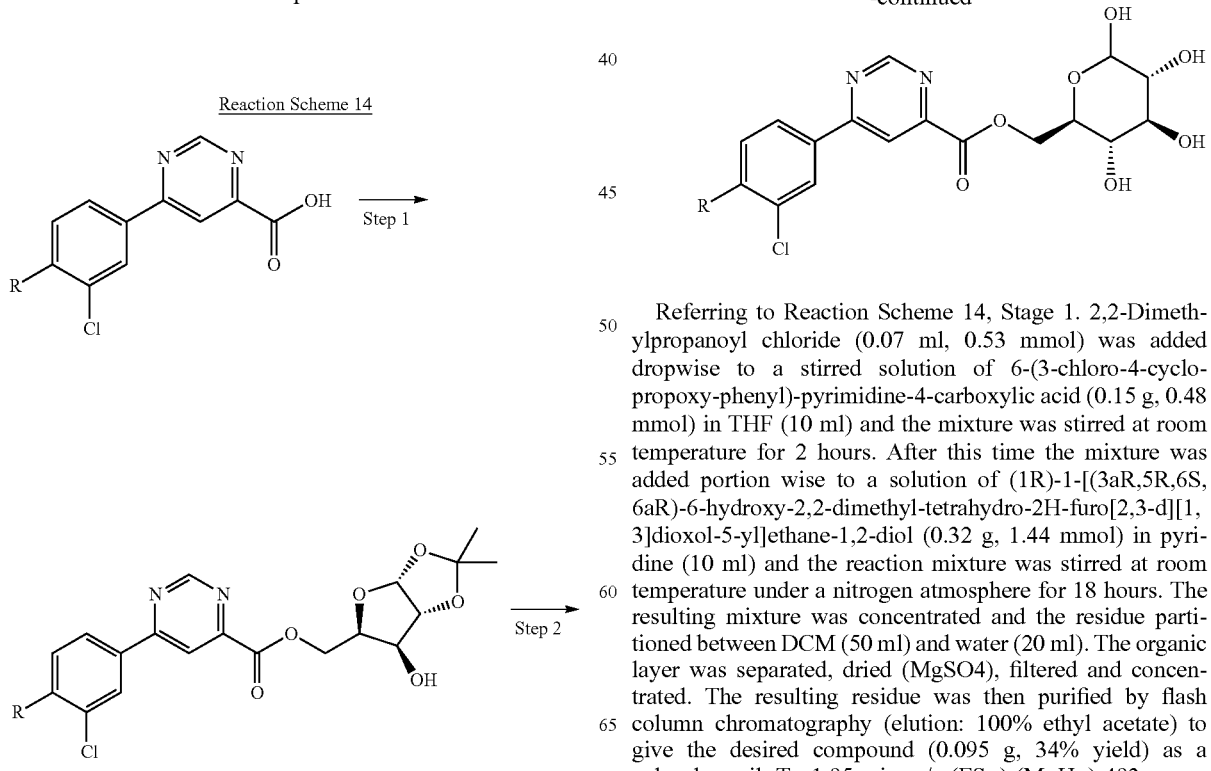

Referring to Reaction Scheme 14, Stage 1. 2,2-Dimethylpropanoyl chloride (0.07 ml, 0.53 mmol) was added dropwise to a stirred solution of 6-(3-chloro-4-cyclopropoxy-phenyl)-pyrimidine-4-carboxylic acid (0.15 g, 0.48 mmol) in THF (10 ml) and the mixture was stirred at room temperature for 2 hours. After this time the mixture was added portion wise to a solution of (1R)-1-[(3aR,5R,6S,6aR)-6-hydroxy-2,2-dimethyl-tetrahydro-2H-furo[2,3-d][1,3]dioxol-5-yl]ethane-1,2-diol (0.32 g, 1.44 mmol) in pyridine (10 ml) and the reaction mixture was stirred at room temperature under a nitrogen atmosphere for 18 hours. The resulting mixture was concentrated and the residue partitioned between DCM (50 ml) and water (20 ml). The organic layer was separated, dried (MgSO4), filtered and concentrated. The resulting residue was then purified by flash column chromatography (elution: 100% ethyl acetate) to give the desired compound (0.095 g, 34% yield) as a colourless oil. Tr=1.95 min m/z (ES+) (M+H+) 493.

Referring to Reaction Scheme 14, Stage 2. 4M HCl in dioxane solution (5 ml) was added in one portion to a stirred solution of 6-(3-chloro-4-cyclopropoxy-phenyl)-pyrimidine-4-carboxylic acid 6-hydroxy-2,2-dimethyl-tetrahydrofuro[2,3-d][1,3]dioxol-5-ylmethyl ester (0.095 g, 0.19 mmol) in dioxane (2 ml) and the mixture was stirred at room temperature overnight. The resulting mixture was concentrated and the resulting residue was then purified by prep HPLC to give the title compound (0.01 g, 13% yield) as a colourless glass.

dissolved in dry DMF (100 mL) in a 2 neck flask. The flask was purged with a stream of nitrogen while cooling in an ice bath for 10 minutes. After this time, thionyl chloride (15.6 mL, 215.6 mmol) was added dropwise over 20 minutes, before being warmed to room temperature and stirred under a nitrogen atmosphere for 2 hours. After this time, the reaction mixture was carefully poured onto ~100 mL ice water. TBME (100 mL) was added, the organic layer was separated and the aqueous extracted with further TBME (3×100 mL). The combined organic layers were washed

| Structure | Molecular Weight | Mass Spec Result |
|---|---|---|
| (structure shown) | 452.85 | [M + Na]+ = 475.0 @ rt = 3.36 + 3.41 min |

Example 15 consecutively with water (2×100 mL), and brine (100 mL) before being dried (MgSO4), filtered and concentrated to Reaction Scheme 15

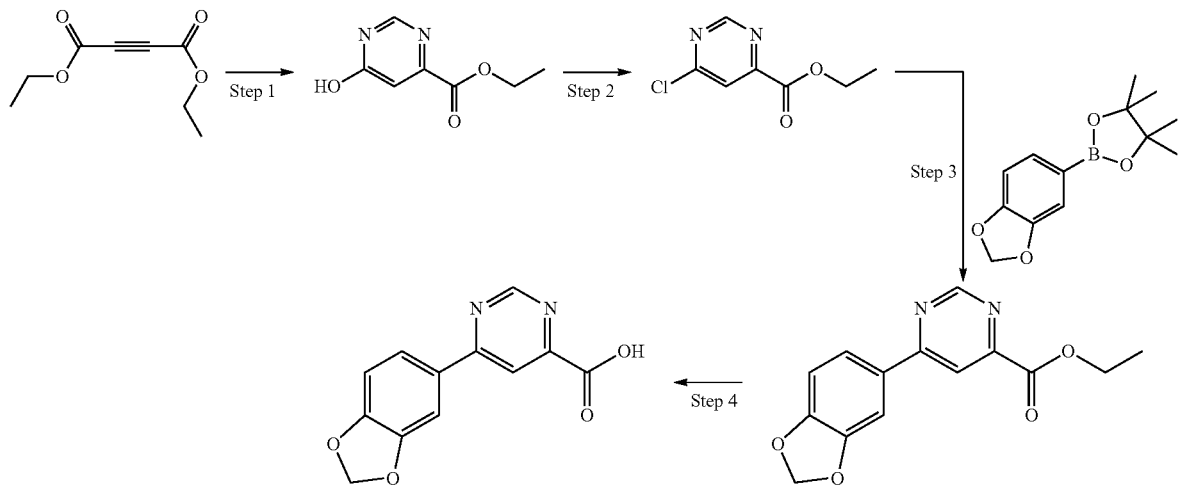

Referring to Reaction Scheme 15, Stage 1. Triethylamine (19.01 ml, 146.92 mmol) was added dropwise to a solution of diethyl but-2-ynedioate (25.0 g, 146.92 mmol) and formamidine hydrochloride (11.83 g, 146.92 mmol) in acetonitrile (500 mL). The resulting red solution was heated at 80° C. for 2.5 hours. After this time the reaction mixture was cooled to 5° C. using a saturated NaCl/ice bath and the reaction was stirred at this temperature for 25 minutes. After this time the resulting solid precipitate was collected under suction and dried on a sinter funnel for 30 minutes under vacuum at room temperature before drying in the vacuum oven at room temperature for 3 hours to give the desired compound (21.3 g, 86% yield) as a pale brown solid. Tr=0.85 min (3.5 minute method) m/z (ES+) (M+H+) 169.

Referring to Reaction Scheme 15, Stage 2. Ethyl 6-hydroxypyrimidine-4-carboxylate (21.3 g, 126.67 mmol) was give the desired compound (8.8 g, 37% yield) as a light orange powder. δH (500 MHz, DMSO) 9.23 (d, J=0.95 Hz, 1H), 8.16 (d, J=1.10 Hz, 1H), 4.39 (q, J=7.09 Hz, 2H), 1.34 (t, J=7.17 Hz, 3H). Tr=1.43 min (3.5 minute method) m/z (ES+) (M+H+) 187.

Referring to Reaction Scheme 15, Stage 3. Tripotassium phosphate (1.12 g, 5.63 mmol) was added in one portion to a stirred solution of 2-(2H-1,3-benzodioxol-5-yl)-4,4,5,5-tetramethyl-1,3,2-dioxaborolane (0.93 g, 3.75 mmol) and ethyl 6-chloropyridine-4-carboxylate (0.7 g, 3.75 mmol) in DMF (20 mL). The mixture was degassed with nitrogen for 5 minutes, after which time Pd(dppf)2Cl2 (0.14 g, 0.19 mmol) was added in one portion, the mixture was then heated to 80° C. and stirred at this temperature for 16 hours under a nitrogen atmosphere. After this time the reaction mixture was cooled to room temperature and partitioned between ethyl acetate (200 mL) and water (100 mL). The organic layer was separated, washed sequentially with water (100 mL) then brine (100 mL) before being dried (MgSO4), filtered and concentrated. The resulting brown solid was purified by flash column chromatography (elution: 40% EtOAc, 60% Heptane) to give the desired compound (0.31 g, 31% yield) as a white solid. Tr=1.87 min m/z (ES+) (M+H+) 273.

Referring to Reaction Scheme 15, Stage 4. NaOH (2M solution, 0.63 mL, 1.27 mmol) was added in one portion to a stirred solution of ethyl 6-(2H-1,3-benzodioxol-5-yl)pyrimidine-4-carboxylate (0.31 g, 1.15 mmol) in THF (10 mL) and the mixture was stirred at room temperature for 16 hours before being heated to reflux for 2 hours. After this time, the reaction mixture was cooled to room temperature and the resulting precipitate was collected by filtration, washed with THF (20 mL) before being dried under vacuum to give the desired compound (0.17 g, 56% yield, >99% purity) as a white solid.

The following compounds were prepared substantially as described above.

| Structure | Molecular Weight | Mass Spec Result |
|---|---|---|
| 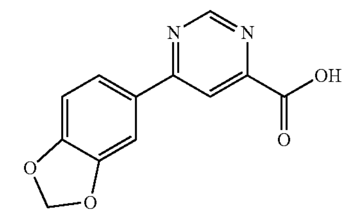 [SMILES: O=C(O)c1cc(-c2ccc3c(c2)OCO3)ncn1] | 244.04 | [M + H]+ = 245/247, 99% @ rt = 3.08 min |
| 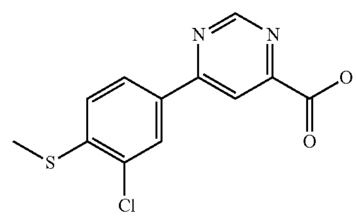 [SMILES: CSc1ccc(-c2cc(C(=O)O)ncn2)cc1Cl] | 280.73 | [M + H]+ = 281/283, 99% @ rt = 2.61 min |
| 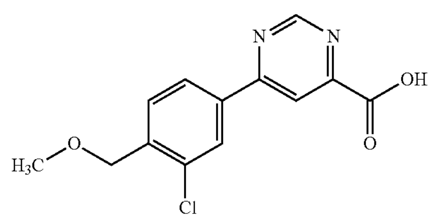 [SMILES: COCc1ccc(-c2cc(C(=O)O)ncn2)cc1Cl] | 278.04 | [M + H]+ = 279/281, 100% @ rt = 3.65 min |
| 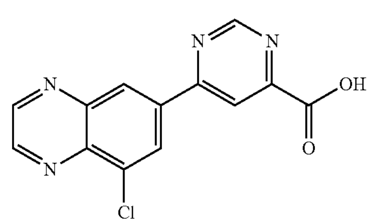 [SMILES: O=C(O)c1cc(-c2cc(Cl)c3nccnc3c2)ncn1] | 286.2 | [M + H]+ = 287/289, 100% @ rt = 3.03 min |

Example 16

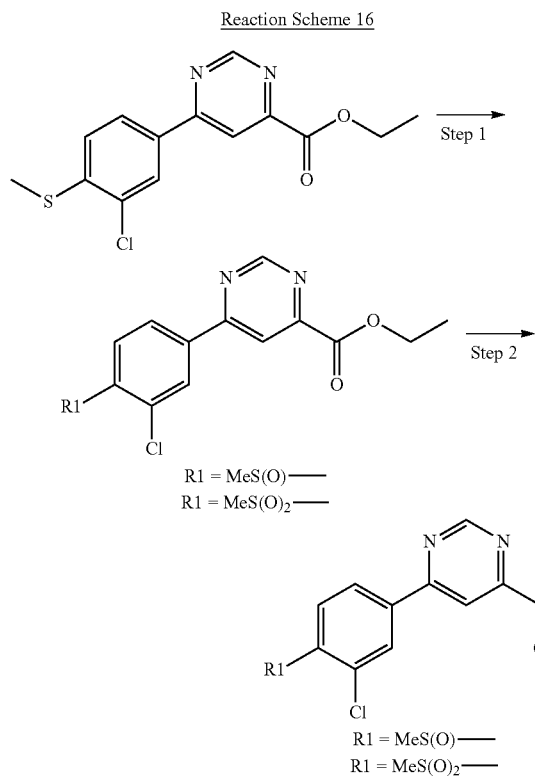

Reaction Scheme 16

R1 = MeS(O)—
R1 = MeS(O)₂—

R1 = MeS(O)—
R1 = MeS(O)₂—

Referring to Reaction Scheme 16, Stage 1. A solution of oxone (0.25 g, 0.40 mmol) in water (12 mL) was added portion wise over 15 minutes to a stirred solution of ethyl 6-[3-chloro-4-(methylsulfanyl)phenyl]pyrimidine-4-carboxylate (0.25 g, 81 mmol) in acetone (12 mL) and the resulting mixture was stirred at room temperature under a nitrogen atmosphere for 18 hours. After this time, the reaction was partitioned between water (20 mL) and ethyl acetate (50 mL). The organic layer was separated, and the aqueous further extracted with ethyl acetate (2×50 mL). The combined organic extracts were then dried (MgSO4), filtered and concentrated. The resulting residue was purified on a Biotage isolera (15% ethyl acetate, 90% heptanes to 100% ethyl acetate) to give the desired compound (0.2 g, 76% yield) as a white solid. δH (500 MHz, DMSO-d6) 9.48 (d, J=1.20 Hz, 1H), 8.66 (d, J=1.22 Hz, 1H), 8.56 (dd, J=1.64, 8.22 Hz, 1H), 8.48 (d, J=1.58 Hz, 1H), 8.02 (d, J=8.21 Hz, 1H), 4.43 (q, J=7.11 Hz, 2H), 2.87 (s, 3H), 1.38 (t, J=7.11 Hz, 3H). Tr=1.64 min m/z (ES+) (M+H+) 325, 327.

Referring to Reaction Scheme 16, Stage 2. NaOH (2M solution, 0.33 mL, 0.66 mmol) was added in one portion to a stirred solution of ethyl 6-(3-chloro-4-methanesulfinylphenyl)pyrimidine-4-carboxylate (0.19 g, 0.61 mmol) in THF (30 mL) and the mixture was stirred at room temperature for 7 hours. After this time, the resulting precipitate was collected by filtration, washed with THF (10 mL) before being dried under vacuum to give the desired compound (0.17 g, 84% yield, >99% purity) as a white solid.

The following compounds were prepared substantially as described above.

| Structure | Molecular Weight | Mass Spec Result |
|---|---|---|
| 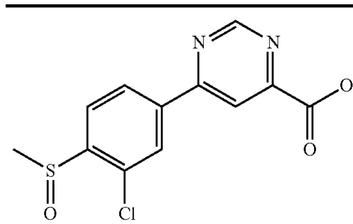 | 296.73 | [M + H]+ = 297/299 98.9% @ rt = 2.83 min |
| 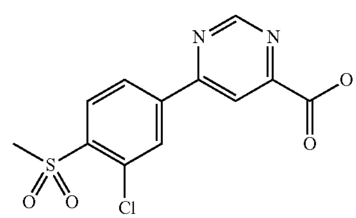 [SMILES: CS(=O)(=O)c1ccc(-c2cc(C(=O)O)ncn2)cc1Cl] | 312.73 | [M + H]+ = 313/315 100% @ rt = 2.92 min |

Example 17

Reaction Scheme 17

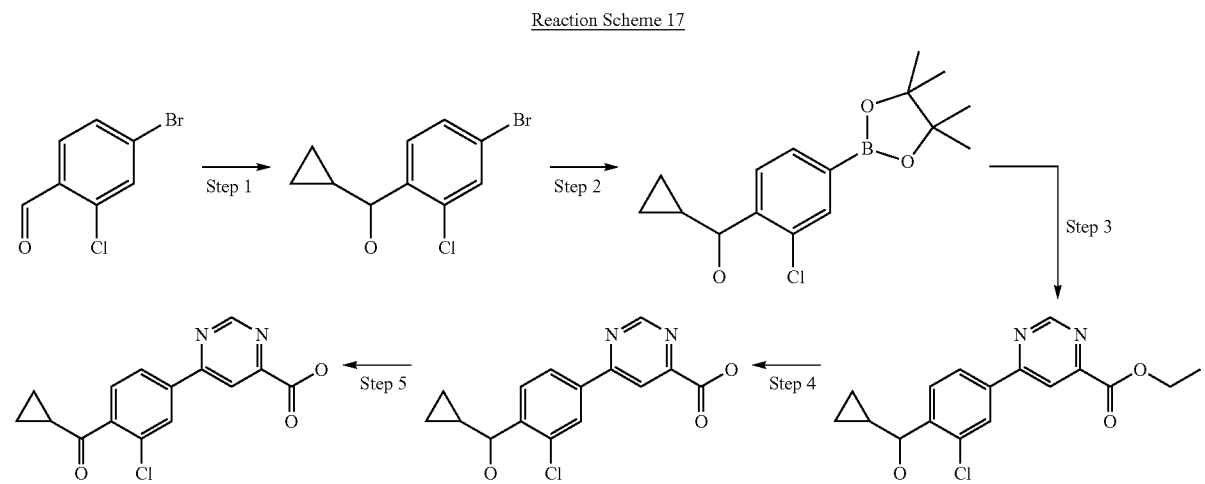

Referring to Reaction Scheme 17, Stage 1. Cyclopropylmagnesium bromide (0.5M solution in THF, 100.0 mL, 50.0 mmol) was added portion wise over 1 hour to a cold (−78° C.), stirred solution of 4-bromo-2-chlorobenzaldehyde (5.5 g, 25.0 mmol) in THF (100 mL) and the mixture was stirred for 1 hour before being allowed to warm to room temperature and stirred for a further 18 hours. After this time, the reaction was quenched by the addition of saturated ammonium chloride (100 mL) and the mixture extracted with ethyl acetate (3×100 mL). The combined organic extracts were combined, washed with water (100 mL) and brine (100 mL) before being dried (MgSO4), filtered and concentrated. The resulting residue was purified by flash column chromatography (elution: 10% ethyl acetate, 90% heptanes) to give the desired compound (5.05 g, 77% yield) as a pale yellow oil. δH (500 MHz, DMSO) 7.66 (d, J=1.89 Hz, 1H) 7.50-7.60 (m, 2H) 5.43 (br. s., 1H) 4.59 (d, J=5.20 Hz, 1H) 1.04-1.15 (m, 1H) 0.29-0.46 (m, 4H).

Referring to Reaction Scheme 17, Stage 2. Potassium acetate (3.72 g, 40.0 mmol) was added in one portion to a stirred solution of (4-bromo-2-chlorophenyl)(cyclopropyl)methanol (3.3 g, 1.3 mmol) and bis-pinacol borane (3.85 g, 1.5 mmol) in DMSO (35 mL). The mixture was degassed with nitrogen for 5 minutes, after which time Pd(dppf)2Cl2 (0.46 g, 0.6 mmol) was added in one portion, the mixture was then heated to 80° C. and stirred at this temperature for 16 hours under a nitrogen atmosphere. After this time the reaction mixture was cooled to room temperature and partitioned between ethyl acetate (100 mL) and water (50 mL). The biphasic suspension was filtered through glass fiber filter paper and the organic layer was separated, washed sequentially with water (3×100 mL) before being dried (MgSO4), filtered and concentrated. The resulting residue was purified by flash column chromatography (elution: 80% heptane, 20% DCM and 2 mL of triethylamine) to give the desired compound (3.5 g, 90% yield) as a colourless oil. δH (500 MHz, DMSO) 7.61 (s, 2H) 7.56 (s, 1H) 5.39 (d, J=4.41 Hz, 1H) 4.66 (t, J=5.20 Hz, 1H) 1.24-1.36 (m, 12H) 1.05-1.12 (m, 1H) 0.24-0.47 (m, 4H).

Referring to Reaction Scheme 17, Stage 3. Tripotassium phosphate (1.03 g, 4.8 mmol) was added in one portion to a stirred solution of [2-chloro-4-(tetramethyl-1,3,2-dioxaborolan-2-yl)phenyl](cyclopropyl)methanol (1.0 g, 3.2 mmol) and ethyl 6-chloropyrimidine-4-carboxylate (0.73 g, 3.89 mmol) in DMF (20 mL). The mixture was degassed with nitrogen for 5 minutes, after which time Pd(dppf)2Cl2 (0.13 g, 0.16 mmol) was added in one portion, the mixture was then heated to 60° C. and stirred at this temperature for 16 hours under a nitrogen atmosphere. After this time the reaction mixture was cooled to room temperature and partitioned between ethyl acetate (100 mL) and water (50 mL). The organic layer was separated, washed sequentially with water (50 mL) then brine (50 mL) before being dried (MgSO4), filtered and concentrated. The resulting red gum was purified by flash column chromatography (elution: 40% EtOAc, 60% Heptane) to give the desired compound (0.74 g, 65% yield) as a colourless oil. δH (500 MHz, DMSO) 9.42 (d, J=1.10 Hz, 1H) 8.57 (d, J=1.10 Hz, 1H) 8.22-8.36 (m, 2H) 7.79 (d, J=8.20 Hz, 1H) 5.52 (br. s., 1H) 4.72 (d, J=5.99 Hz, 1H) 4.43 (q, J=7.09 Hz, 2H) 1.38 (t, J=7.09 Hz, 3H) 1.15-1.22 (m, 1H) 0.29-0.53 (m, 4H). Tr=2.27 min m/z (ES+) (M+H+) 321.

Referring to Reaction Scheme 17, Stage 4. NaOH (2M solution, 0.24 mL, 0.48 mmol) was added in one portion to a stirred solution of ethyl 6-{3-chloro-4-[cyclopropyl(hydroxy)methyl]phenyl}pyrimidine-4-carboxylate (0.16 g, 0.48 mmol) in THF (2 mL) and the mixture was stirred at room temperature for 16 hours. After this time, the resulting precipitate was collected by filtration, washed with water (1 mL) and DCM (20 mL) before being dried under vacuum to give the desired compound (0.065 g, 41% yield) as a white solid.

Referring to Reaction Scheme 17, Stage 5. Dess-Martin Periodinane (0.36 g, 1.08 mmol) was added portion wise to a cooled (0° C.), stirred solution of 6-{3-chloro-4-[cyclopropyl(hydroxy)methyl]phenyl}pyrimidine-4-carboxylic acid (0.36 g, 1.08 mmol) in DCM (3 mL) and the mixture was allowed to warm to room temperature and stirred for 18 hours. After this time, the mixture was partitioned between DCM (20 mL) and saturated sodium bicarbonate (20 mL). The organic layer was separated, washed with water (100 mL) and brine (50 mL) before being dried (MgSO4), filtered and concentrated. The resulting residue was purified by flash column chromatography (elution: 20% ethyl acetate, 80% heptanes) to give the desired compound (0.26 g, 74% yield) as a white solid.

The following compounds were prepared substantially as described above.

| Structure | Molecular Weight | Mass Spec Result |
|---|---|---|
| 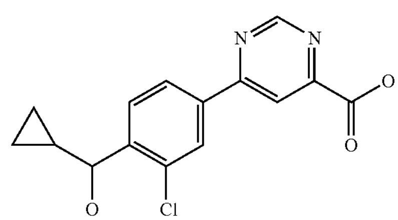 [SMILES: O=C(O)c1cc(-c2ccc(C(O)C3CC3)c(Cl)c2)ncn1] | 304.74 | [M + H]+ = 305/307, 98% @ rt = 3.25 min |
| 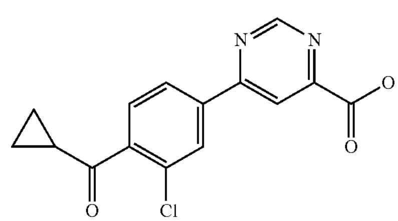 [SMILES: O=C(O)c1cc(-c2ccc(C(=O)C3CC3)c(Cl)c2)ncn1] | 302.72 | [M + H]+ = 303/305, 100% @ rt = 3.54 min |

Example 18

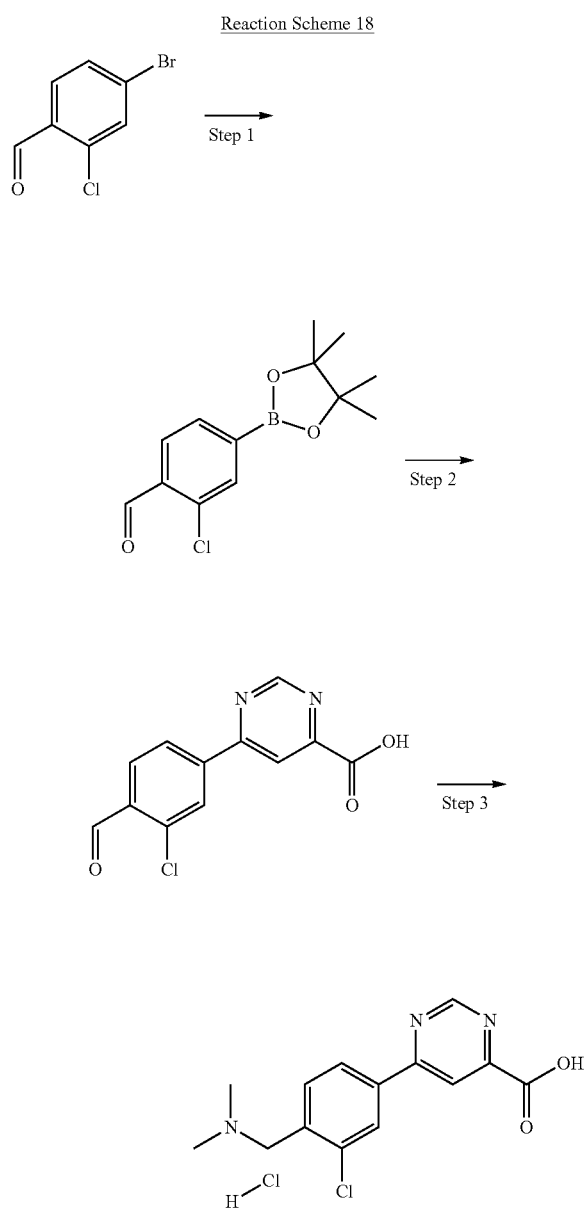

Referring to Reaction Scheme 18, Stage 1. To a stirred solution of 4-bromo-2-chlorobenzaldehyde (0.51 g, 2.32 mmol) in a mixture of dry dioxane (2.5 mL) and dry DMF (0.60 mL) was added 4,4,4',4',5,5,5',5'-octamethyl-2,2'-bi-1,3,2-dioxaborolane (0.64 g, 2.52 mmol) and potassium acetate (0.7 g, 7.13 mmol). The mixture was degassed and then 1,1'-bis(diphenylphosphanyl)ferrocene-dichloropalladium (1:1) (0.08 g, 0.11 mmol) was added. The mixture was further degassed before heating to 80° C. for 3 hours under an atmosphere of nitrogen gas. To the cooled reaction mixture was added water (30 mL) and EtOAc (15 mL); the organic layer was then washed with a 3:1 mixture of water and brine (2×40 mL), brine (5 mL), dried (MgSO4), filtered and concentrated. The resulting residue was then absorbed onto silica gel (1.6 g) and purified by dry flash chromatography (0-20% EtOAc in heptane) to give the desired compound (0.25 g, 37% yield @ 90% NMR purity) as a white partial solid. Tr=1.46 min (63%) & 2.45 min (30%) m/z (ES+) (M+H+) no ionisation.

Referring to Reaction Scheme 18, Stage 2. To a degassed stirred solution of ethyl 6-chloropyrimidine-4-carboxylate (0.17 g, 0.9 mmol) and 2-chloro-4-(tetramethyl-1,3,2-dioxaborolan-2-yl)benzaldehyde (0.22 g, 0.81 mmol) in dioxane (2.5 mL) was added 2M K2CO3 (1.25 mL). Pd(PPh3)4 (57 mg, 0.05 mmol) was then added and the reaction mixture was further degassed before heating to 90° C. under an atmosphere of nitrogen gas for 2 hours. After this time, the reaction mixture was cooled to room temperature and concentrated. Water (5 mL) was then added and the solid filtered, washed with water (2 mL), acetone (3×2 mL) and dried under vacuum. The solid was suspended in a mixture of EtOAc (30 mL) and 1N HCl (10 mL) and then heated to achieve partial solution. The cooled two-phase system was then sonicated to achieve full dissolution. The aqueous layer was re-extracted with EtOAc (10 mL); the combined organics were washed with brine (5 mL), dried (MgSO4), filtered and concentrated to give the desired compound (0.1 g, 42% yield @ 85% purity) as a beige solid. Tr=1.58 min m/z (ES+) (M+H+) 263/265.

Referring to Reaction Scheme 18, Stage 3. To a stirred suspension of 6-(3-chloro-4-formylphenyl)pyrimidine-4-carboxylic acid (93 mg, 0.35 mmol) in 1,2-dichloroethane (5 mL) was added dimethylamine (2M solution in THF, 0.53 mL) at room temperature followed by molecular sieves and sodium triacetoxyborohydride (125 mg, 0.59 mmol). After 1.5 hours, acetic acid (31 µl, 0.54 mmol) was added and the reaction stirred at room temperature for 2.5 days. Further dimethylamine (2M solution in THF, 1.0 mL) and sodium triacetoxyborohydride (130 mg) were added and the mixture stirred for 6 h before a further amount of dimethylamine (2M in THF, 1.0 mL), sodium triacetoxyborohydride (130 mg) and AcOH (62 L). The mixture was then stirred for 18 hours. The reaction mixture was filtered and the filtrate was concentrated. A solution of 1:1 (v/v) MeCN:water (0.5 mL) was added to the resulting residue and then concentrated HCl (0.5 mL) was added dropwise. The crude product dissolved and was purified by preparative HPLC (acetonitrile and water) to give 14 mg of an off-white solid. The solid was further purified by sonication in TBME (1 mL) and collected by filtration. The solid was washed with TBME (4×1 mL) and dried to give the desired compound (7.8 mg, 7.9% yield @ 95% purity) as a off-white solid.

The following compounds were prepared substantially as described above.

| Structure | Molecular Weight | Mass Spec Result |
|---|---|---|
| 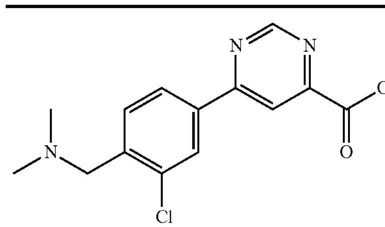 | 291.74 | [M + H]+ = 292/294, 100% @ rt = 2.00 min |

Example 19

Reaction Scheme 19

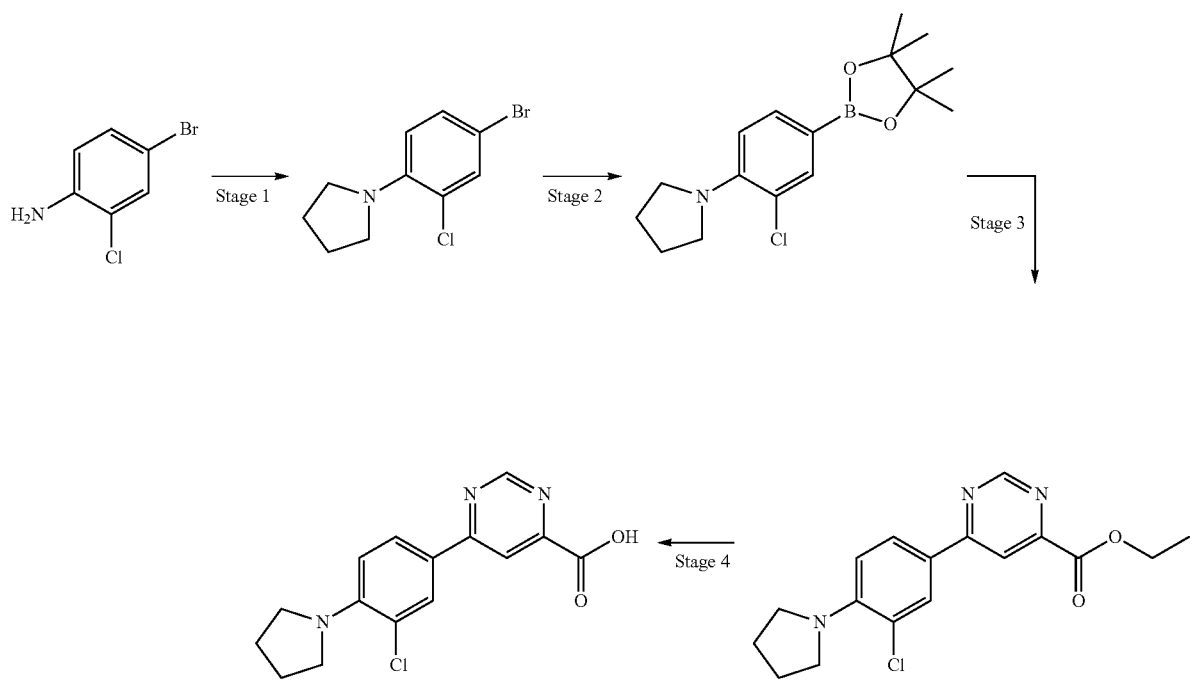

Referring to Reaction Scheme 19, Stage 1. 4-Bromo-2-chloroaniline (2.0 g, 9.69 mmol), 1,4-dibromobutane (2.31 ml, 19.4 mmol), potassium carbonate (2.68 g, 19.4 mmol), water (25 mL) and dioxane (10 mL) were heated to 100° C. overnight with vigorous stirring. The reaction mixture was allowed to cool then extracted with EtOAc (2×25 mL). The combined organics were washed with brine (15 mL), dried (MgSO4), filtered and concentrated to give an orange oil. Column chromatography (Elution: 0-20% EtOAc-heptane) afforded the desired compound (1.16 g, 45% yield) as a yellow oil. δH (500 MHz, DMSO-d6) 7.48 (d, J=2.36 Hz, 1H), 7.33 (dd, J=2.36, 8.83 Hz, 1H), 6.87 (d, J=8.83 Hz, 1H), 3.29-3.33 (m, 4H), 1.87 (td, J=3.43, 6.38 Hz, 4H); Tr (3 min)=2.68 min m/z (ES+) (M+H)+260, 262.

Referring to Reaction Scheme 19, Stage 2. Potassium acetate (1.31 g, 13.4 mmol), bis(pinacolato)diboron (1.36 g, 5.32 mmol) and 1-(4-bromo-2-chlorophenyl)pyrrolidine (1.16 g, 4.45 mmol) were suspended in DMSO (15 mL). The solution was degassed with N2 for 5 min. PdCl2(dppf) (0.16 g, 0.22 mmol) was added and the reaction mixture was heated to 80° C. for 3 h. The reaction was cooled to rt. Water (30 mL) was added to the reaction and the aqueous was extracted using EtOAc (5×20 mL). The combined organic layers were washed with water (100 mL), brine (50 mL), dried (MgSO4), filtered, and concentrated to give a black oil. Column chromatography (Elution; 8% EtOAc-heptane) afforded the desired compound (1.14 g, 83% yield) as a pale yellow oil. Tr (3 min)=2.70 min m/z (ES+) (M+H)+307.

Referring to Reaction Scheme 19, Stages 3 & 4 were carried out as described in Reaction Scheme 15.

The following compounds were prepared substantially as described above.

| Structure | Molecular Weight | Mass Spec Result |
|---|---|---|
| 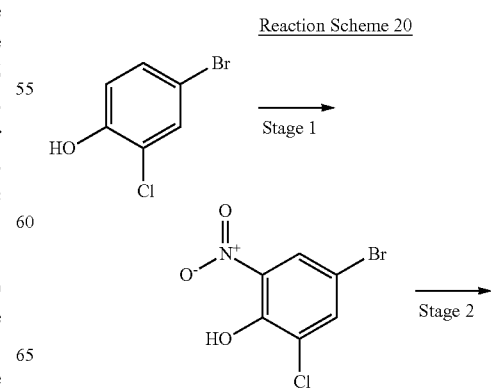 | 303.74 | [M + H]+ = 304/306, 100% @ rt = 4.14 min |

Example 20

Reaction Scheme 20

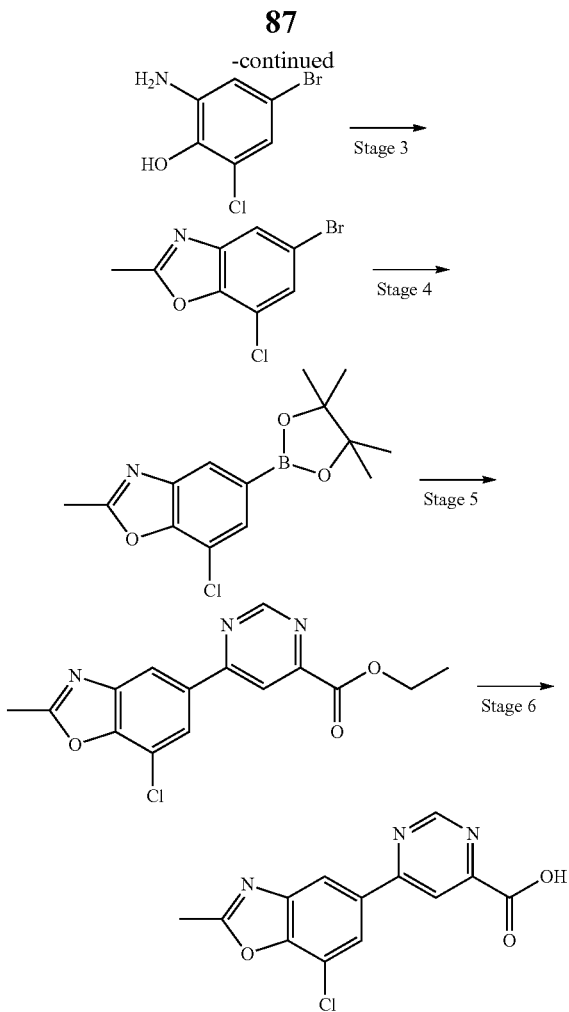

Referring to Reaction Scheme 20, Stage 1. In a three neck flask with dropping funnel, thermometer and nitrogen bubbler (no nitrogen input), 4-bromo-2-chlorophenol (5.0 g, 0.024 mol) was fully dissolved in acetic acid (25 mL) at room temperature. Nitric acid (70%, 2.9 mL, 0.048 mol) was added slowly dropwise over approx 15 minutes keeping the temperature at below 30° C. The reaction turned orange with an orange precipitate. The reaction was stirred for a further 4 hours at 20° C. After this time the reaction mixture was cautiously transferred via pipette onto approximately 50 mL ice. Once the ice had melted the yellow precipitate was filtered and washed with water (50 mL). The yellow solid was air dried under vacuum for 1 hour before being dissolved in DCM and dry loaded onto 5.5 g silica. The compound was purified by flash column chromatography (elution; 100% heptane, to 20% DCM in heptane, to 40% DCM in heptane, to 50% DCM in heptanes) to give the desired compound (4.38 g, 72% yield @ 100% UV purity) as a yellow solid. Tr=1.97 min m/z (ES+) no ionisation.

Referring to Reaction Scheme 20, Stage 2. 4-Bromo-6-chloro-2-nitrophenol (4.38 g, 17.35 mmol) was dissolved in ethanol (120 mL). Water (28 mL) and saturated aqueous ammonium chloride (28 mL) were added followed by iron powder (7.75 g, 139 mmol). The reaction was heated to 50° C. and stirred for 1 hour, after which time the reaction was cooled to room temperature and filtered through a pad of celite (approx. 5 cm in a Jones tube), washing with 50 mL EtOH followed by excess EtOAc until the liquid ran clear. The organic layer was washed with water (50 mL). The water was re-extracted with EtOAc (2×200 mL). The combined organic extracts were washed with brine (20 mL), dried (MgSO4), filtered and concentrated. The resulting residue was dry loaded onto 5 g silica and purified by flash column chromatography (elution; 0-30% EtOAc in heptanes) to give the desired compound (2.76 g, 72% yield @ 100% UV purity) as a pale brown solid. Tr=1.65 min m/z (ES+) (M+H+) 222/224/226.

Referring to Reaction Scheme 20, Stage 3. 2-Amino-4-bromo-6-chlorophenol (2.66 g, 11.96 mmol) was dissolved in triethylorthoacetate (24 mL). pTSA monohydrate (0.068 g, 0.359 mmol) was added and the reaction was stirred at 140° C. overnight. After this time the reaction was cooled to room temperature and the resulting solid was collected by filtration and dried under suction at room temperature for 2 hours to give the title compound (1.58 g, 54% yield @ 100% UV purity) as a white solid. Tr=2.07 min m/z (ES+) (M+H+) 246/248.

Referring to Reaction Scheme 20, Stages 4, 5 & 6 were carried out as described in Reaction Scheme 15.

The following compounds were prepared substantially as described above.

| Structure | Molecular Weight | Mass Spec Result |
|---|---|---|
| (oxazole-pyrimidine ester structure with Cl) | 289.68 | [M + H]+ = 290/292, 100% @ rt = 3.42 min |

Example 21

Reaction Scheme 21

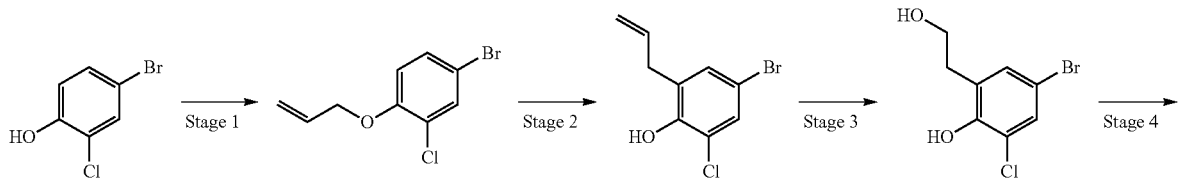

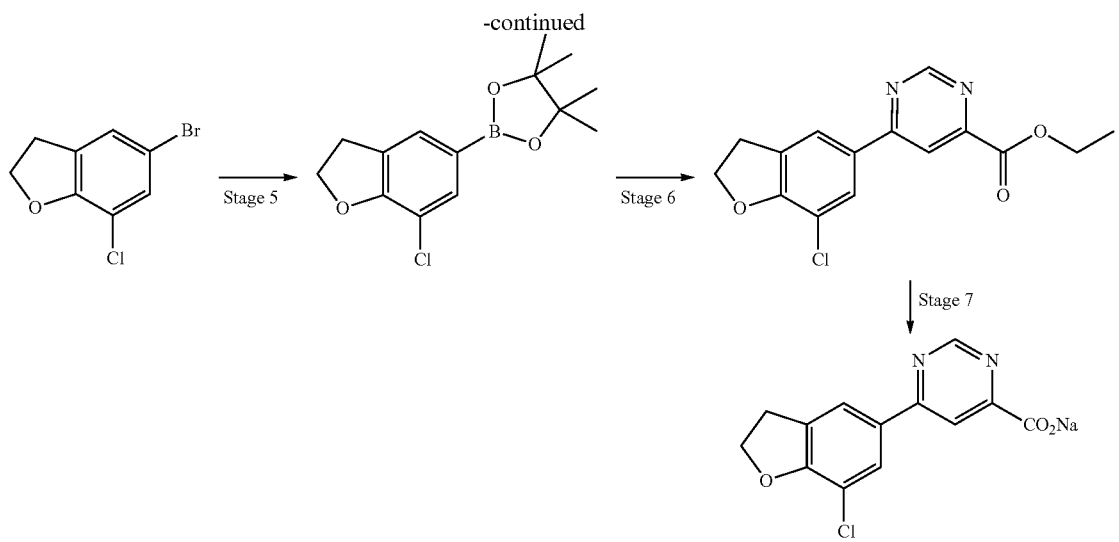

Referring to Reaction Scheme 21, Stage 1. A solution of 4-bromo-2-chlorophenol (10.0 g, 48.0 mmol) in anhydrous DMF (30 mL) was added to a stirred suspension of sodium hydride (2.31 g, 58.0 mmol) in DMF (20 mL) cooled to 0° C. under nitrogen over 15 min, and stirring continued for 30 min. 3-Bromoprop-1-ene (7.00 g, 58.0 mmol) was added dropwise at 0° C. After 1 h, the mixture was allowed to warm to room temperature and then stirred for 3 d. Aqueous saturated NH4Cl (50 mL) was added over 10 min with ice-cooling, and the mixture was concentrated. The residue was treated with water (100 mL) and the mixture extracted with ethyl acetate (3×120 mL). The combined, dried (Na2SO4) organic extracts were concentrated to give an oil which contained DMF. A solution of the oil in ethyl acetate (100 mL) was washed with water (100 mL) and the dried (Na2SO4) organic layer was concentrated to give the desired compound (11.6 g, 87% yield) as a colourless oil. δH (500 MHz, CDCl3) 7.50 (d, J=2.40 Hz, 1H), 7.30 (dd, J=2.40, 8.77 Hz, 1H), 6.79 (d, J=8.78 Hz, 1H), 6.04 (ddt, J=5.10, 10.38, 17.14 Hz, 1H), 5.45 (dd, J=1.44, 17.26 Hz, 1H), 5.32 (dd, J=1.33, 10.57 Hz, 1H), 4.59 (d, J=5.10 Hz, 2H).

Referring to Reaction Scheme 21, Stage 2. A solution of 1-allyloxy-4-bromo-2-chloro-benzene (90%, 11.6 g, 42 mmol) in mesitylene (200 mL) was heated under nitrogen for 48 h at 190° C. with stirring. The reaction was concentrated and purified by column chromatography (Elution: 0-10% EtOAc-heptane) to afford the desired compound (4.66 g, 36% yield) as a colourless oil. Tr (3 min)=2.22 min m/z (ES+) (M+H+) 245, 247.

Referring to Reaction Scheme 21, Stage 3. Sodium periodate (9.04 g, 42.3 mmol) was added to a stirred mixture of 2-allyl-4-bromo-6-chloro-phenol (5.23 g, 21.1 mmol), THF (100 mL) and water (100 mL) at room temperature. After 5 min, osmium tetroxide (13.5 ml of a 0.157 M solution in water, 2.1 mmol) was added and stirring continued for 1.5 h. The mixture was poured into brine (100 mL) and extracted with ethyl acetate (2×100 mL) and the combined, dried (Na2SO4) organic extracts were concentrated to give a dark oil. A stirred solution of the dark oil in methanol (100 mL) under nitrogen was cooled to 0° C., and treated with sodium borohydride (2.40 g, 63.4 mmol) in small portions over 20 min, maintaining the temperature between 0 and 10° C. After stirring for 16 h, the mixture was concentrated, treated with aqueous 1M hydrochloric acid (80 mL) and extracted with ethyl acetate (2×100 mL). The combined, dried (Na2SO4) organic extracts were concentrated, and the residue purified by column chromatography (Elution: 5-40% EtOAc-heptane) to afford the desired compound (1.60 g, 27% yield) as a colourless oil. Tr (3 min)=1.81 min m/z (ES+) (M+H+) 249, 251.

Referring to Reaction Scheme 21, Stage 4. DIAD (1.52 ml, 7.70 mmol) was added to a stirred solution of 4-bromo-2-chloro-6-(2-hydroxy-ethyl)-phenol (1.49 g, 5.92 mmol) and triphenylphosphine (2.02 g, 7.70 mmol) in dry THF (1.5 mL) under nitrogen, with ice-cooling. After stirring for 16 h at rt, the solution was evaporated and the residual oil purified by column chromatography (Elution: 0-10% EtOAc-heptane) afforded the desired compound (1.20 g, 68% yield) as a colourless oil. Tr (3 min)=2.27 min m/z (ES+) no ionization.

Referring to Reaction Scheme 21, Stages 5, 6 & 7 were carried out as described in Reaction Scheme 15.

The following compounds were prepared substantially as described above.

| Structure | Molecular Weight | Mass Spec Result |
|---|---|---|
| (structure shown) | | [M + H]+ = 277/279, 100% @ rt = 3.53 min |

Example 22

Reaction Scheme 22

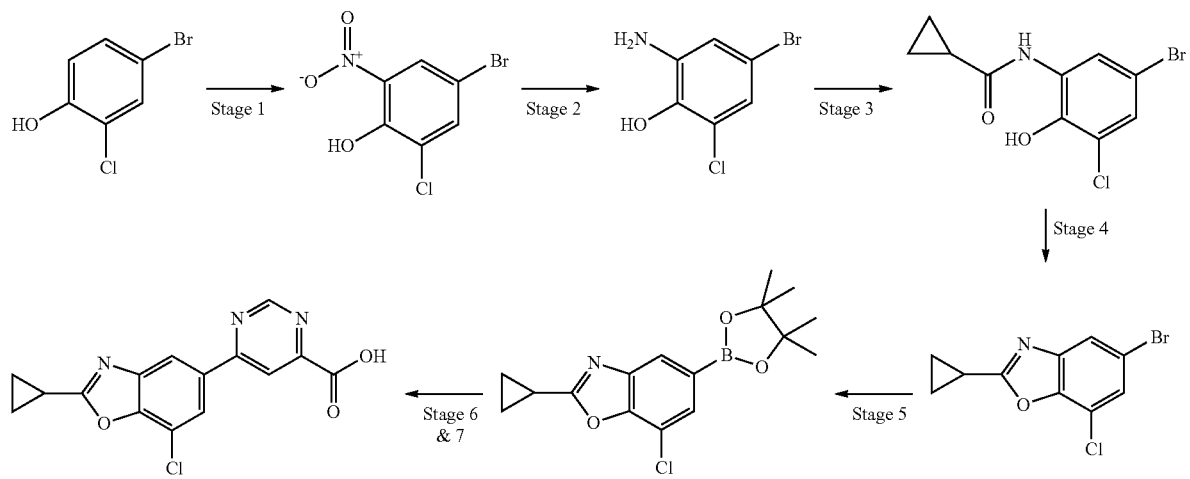

Referring to Reaction Scheme 22, Stage 1. 4-Bromo-2-chlorophenol (14.0 g, 0.067 mol) was dissolved in acetic acid (75 mL) at room temperature. Nitric acid (70%, 8.00 ml, 0.145 mol) was added dropwise over approx 30 min keeping the temperature at roughly 20-22° C. After 1 h at rt, the reaction mixture was cautiously transferred via pipette onto approx 100 mL ice. Once the ice had melted the yellow precipitate was filtered, washing with a very small volume of water. The yellow solid was dried under suction. Purification by dry flash chromatography (Elution: 0-50% DCM-heptane) afforded the desired compound (12.0 g, 70% yield) as a yellow powder. δH (500 MHz, DMSO) 11.35 (br. s., 1H) 8.09 (d, J=2.52 Hz, 1H) 8.07 (d, J=2.52 Hz, 1H); Tr (3 min)=1.97 min m/z (ES+) no ionization.

Referring to Reaction Scheme 22, Stage 2. 4-Bromo-2-chloro-6-nitrophenol (12.0 g, 47.5 mmol) was dissolved in ethanol (350 mL). Water (80 mL) and saturated aqueous ammonium chloride (80 mL) were added, followed by iron powder (21.2 g, 380 mmol). The reaction was heated to 50° C. and stirred for 2 h. The reaction was cooled to rt and filtered through a prewashed pad of celite, washing with 100 mL EtOH followed by excess EtOAc (approx 1.5 l) until the liquid ran clear. The filtrate was concentrated to remove organic solvents. EtOAc (approx 400 mL) was added to the aqueous residue and the layers were separated. The organic phase was washed with water (150 mL) and brine (100 mL). The aqueous layers were re-extracted with EtOAc (2×150 mL). The combined organics were filtered to remove a pale brown solid and evaporated to dryness to give a purple solid. Dry flash chromatography (Elution: 0-30% EtOAc-heptane) afforded the desired compound (6.5 g, 61% yield) as a pale solid. δH (500 MHz, DMSO) 9.01 (br. s., 1H) 6.71 (d, J=2.36 Hz, 1H) 6.66 (d, J=2.36 Hz, 1H) 5.23 (br. s., 2H); Tr (3 min)=1.70 min m/z (ES+) (M+H)+222, 224, 226.

Referring to Reaction Scheme 22, Stage 3. 2-Amino-4-bromo-6-chlorophenol (2.04 g, 9.18 mmol) was dissolved in DCM (anhydrous, 30 ml). Triethylamine (1.6 ml, 11.5 mmol) was added and the reaction was stirred at rt for 1 h under nitrogen. The reaction was cooled in an ice bath for 15 min and then cyclopropanecarbonyl chloride (0.700 mL, 7.65 mmol) was added dropwise over a period of 20 min. The reaction was allowed to gradually warm to rt and stirred for 2 h at rt. The reaction was cooled in an ice bath and an extra 0.2 eq. acid chloride was added dropwise. The reaction was allowed to warm to rt and stirred at rt for 2 h. DCM (20 mL) was added to the reaction followed by water (50 mL). The organic and aqueous layers were separated. The organic layer was washed with water (3×50 mL), brine (30 mL), dried (MgSO4), filtered and concentrated to give the desired product which was carried forward without further purification.

Referring to Reaction Scheme 22, Stage 4. A crude 4:1:1 mixture of N-(5-bromo-3-chloro-2-hydroxyphenyl)cyclopropanecarboxamide, 2-amino-4-bromo-6-chlorophenylcyclopropanecarboxylate and 4-bromo-2-chloro-6-cyclopropaneamido phenylcyclopropanecarboxylate (2.77 g) was dissolved in toluene (30 mL). TsOH monohydrate (2.54 g, 13.4 mmol) was added and the reaction was stirred at 115° C. for 16 h. The reaction was cooled to rt and concentrated to give a brown oil. The residue was re-dissolved in EtOAc (100 mL). The solution was washed with saturated aqueous sodium bicarbonate (3×100 mL), water (3×100 mL), brine (50 mL) and dried (MgSO4). Filtration and concentration gave a brown oil. Column chromatography (Elution: 0-10% EtOAc-heptane) afforded the desired compound (1.18 g, 42%) as an orange crystalline solid. δH (500 MHz, DMSO) 7.85 (d, J=1.73 Hz, 1H) 7.68 (d, J=1.58 Hz, 1H) 2.27-2.40 (m, 1H) 1.08-1.38 (m, 4H); Tr (3 min)=2.38 min m/z (ES+) (M+H)+272, 274.

Referring to Reaction Scheme 22, Stages 5, 6 & 7 were carried out as described in Reaction Scheme 15.

The following compounds were prepared substantially as described above.

| Structure | Molecular Weight | Mass Spec Result |
|---|---|---|
| (Example 23 structure) | 315.72 | [M + H]+ = 316/318, 100% @ rt = 3.84 min |

Example 23

Reaction Scheme 23

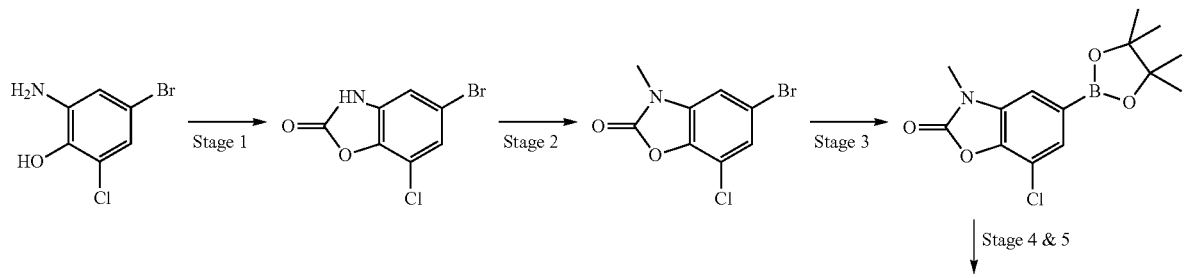

Referring to Reaction Scheme 23, Stage 1. 2-amino-4-bromo-6-chlorophenol (2.50 g, 11.2 mmol) was dissolved in THF (30 ml). CDI (2.73 g, 16.9 mmol) was added and the reaction was stirred at 65° C. After 2 h the reaction was cooled to rt and concentrated to give an orange solid. The residue was redissolved in EtOAc (100 mL) and the organic phase was washed with water (50 mL), 2M HCl (3×50 mL), water (100 mL) and brine (20 mL) and dried (MgSO4). Filtration and concentration afforded the desired compound (2.7 g, 97% yield) as a white solid. δH (500 MHz, DMSO-d6) 12.01 (br. s., 1H) 7.44 (d, J=1.73 Hz, 1H) 7.26 (d, J=1.73 Hz, 1H); Tr (3 min)=1.87 min m/z (ES−) (M−H)− 246, 248.

Referring to Reaction Scheme 23, Stage 2. 5-Bromo-7-chloro-2,3-dihydro-1,3-benzoxazol-2-one (0.60 g, 2.4 mmol) was dissolved in anhydrous DMF (10 mL) and the reaction was cooled in an ice bath. Sodium hydride (60% in oil, 0.15 g, 3.6 mmol) was added portionwise and the reaction was stirred in the ice bath for 1 h. Methyl iodide (0.18 ml, 0.29 mmol) was added and the reaction was stirred at rt for 2 hours. The reaction was cooled in a slush bath. Water (5 mL) was added cautiously followed by EtOAc (20 mL). The layers were separated. The aqueous was re-extracted with EtOAc (2×15 mL). The combined organic layers were washed with water (10 mL) and brine (10 mL) and dried (MgSO4). Filtration and concentration gave a colourless oil. Column chromatography (Elution: 0-20% EtOAc-heptane) afforded the desired compound (540 mg, 85% yield) as a pink solid. δH (500 MHz, CDCl3) 7.30 (d, J=1.73 Hz, 1H) 7.03 (d, J=1.73 Hz, 1H) 3.41 (s, 3H); Tr (3 min)=1.97 min m/z (ES+) No ionisation.

Referring to Reaction Scheme 23, Stages 3, 4 & 5 were carried out as described in Reaction Scheme 15.

The following compounds were prepared substantially as described above.

| Structure | Molecular Weight | Mass Spec Result |
|---|---|---|
| 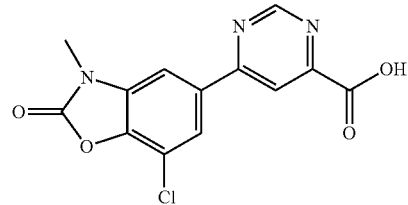 | 305.68 | [M + H]+ = 306/308, 98% @ rt = 3.35 min |

Example 24

Reaction Scheme 24

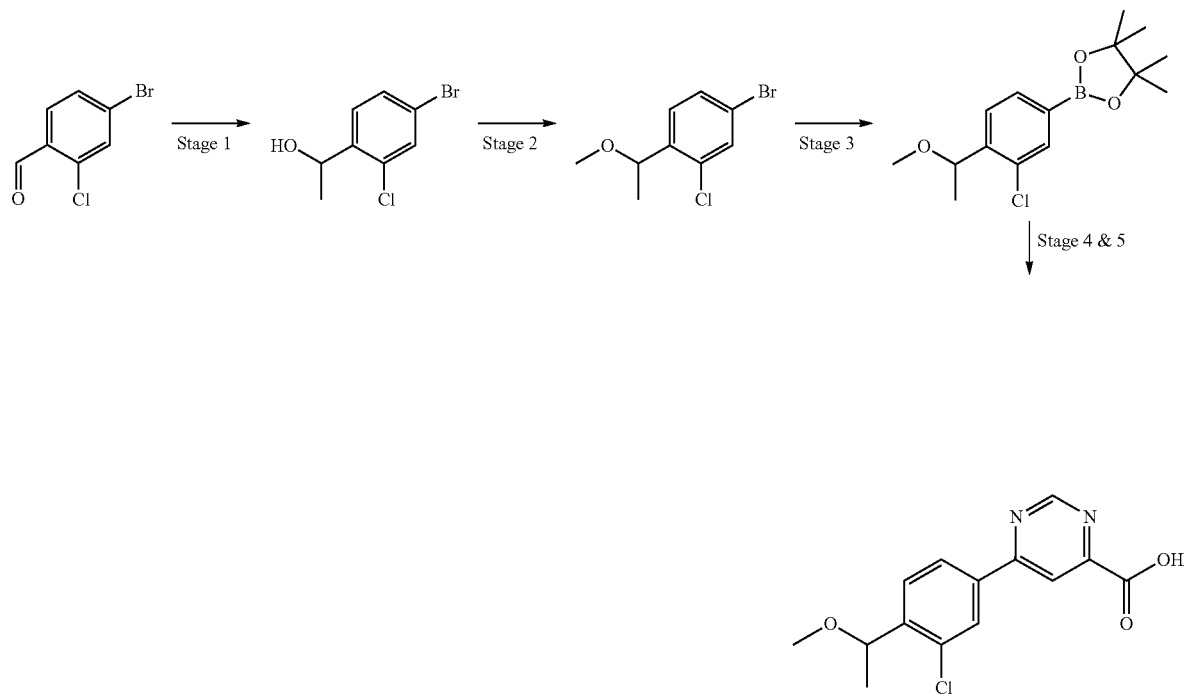

Referring to Reaction Scheme 24, Stage 1. Methylmagnesium bromide (1.4M in toluene/THF, 1.5 mL, 0.046 mol) was added drop wise over 1 hour to a cold (−78° C.), stirred solution of 4-bromo-2-chlorobenzaldehyde (5.0 g, 0.023 mol) in THF (100 mL) and the mixture was stirred at this temperature under a nitrogen atmosphere for 1 hour. After this time, the reaction mixture was allowed to warm to room temperature over 1 hour before being stirred for a further 1.5 hours. The reaction mixture was then cooled to 5° C. in an ice bath and stirred for 10 minutes before saturated ammonium chloride (40 mL) was added drop wise and stirring continued at this temperature for a further 10 minutes before being allowed to warm to room temperature. The resulting mixture was then extracted with ethyl acetate (1×100 mL), the organic layer was washed sequentially with water (100 mL), and brine (100 mL) before being dried (MgSO4), filtered and concentrated. The resulting residue was purified by flash column chromatography (elution: 10% ethyl acetate, 90% heptanes) to give the desired compound (4.33 g, 81% yield) as a colourless oil. 6H (500 MHz, DMSO) 7.64 (d, J=1.58 Hz, 1H) 7.49-7.60 (m, 2H) 5.47 (d, J=3.00 Hz, 1H) 4.96 (dd, J=6.07, 2.60 Hz, 1H) 1.28 (d, J=6.31 Hz, 3H).

Referring to Reaction Scheme 24, Stage 2. Sodium hydride (60% in oil, 0.38 g, 9.6 mmol) was added portion wise over 5 minutes to a cooled (0° C.), stirred solution of 1-(4-bromo-2-chlorophenyl)ethan-1-ol (1.5 g, 6.4 mmol) in DMF (15 mL) and the reaction was stirred at this temperature for 20 minutes under a nitrogen atmosphere. After this time, methyl iodide (0.48 mL, 7.6 mmol) was added in one portion and the reaction mixture was allowed to warm to room temperature before being stirred for a further 18 hours. The reaction was quenched by the drop wise addition of water (15 mL) over 10 minutes and the resulting solution was extracted with ethyl acetate (2×30 mL). The combined organic extracts were washed sequentially with water (100 mL) and brine (10 mL) before being dried (MgSO4), filtered and concentrated to give the desired compound (1.5 g, 99% yield) as a yellow oil. 6H (500 MHz, DMSO) 7.71 (d, J=1.89 Hz, 1H) 7.60 (dd, J=8.35, 1.89 Hz, 1H) 7.39 (d, J=8.35 Hz, 1H) 4.63 (q, J=6.46 Hz, 1H) 3.16 (s, 3H) 1.26-1.38 (m, 3H).

Referring to Reaction Scheme 24, Stages 3, 4 & 5 were carried out as described in Reaction Scheme 15.

The following compounds were prepared substantially as described above.

| Structure | Molecular Weight | Mass Spec Result |
|---|---|---|
| 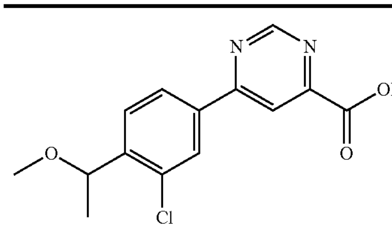 | 292.72 | [M + H]+ = 293/295, 99% @ rt = 3.72 min |

Example 25

Reaction Scheme 25

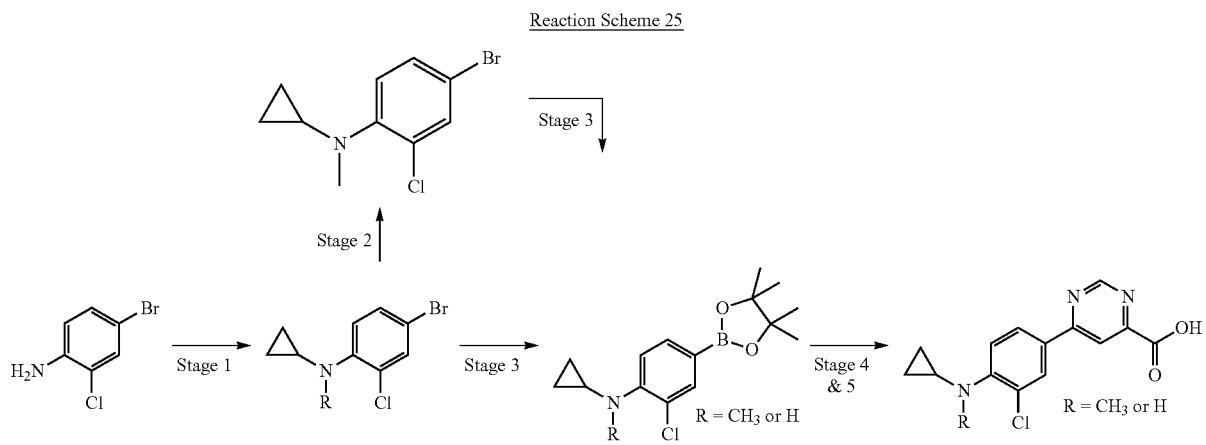

Referring to Reaction Scheme 25, Stage 1. [(1-Ethoxycyclopropyl)oxy](trimethyl)silane (5.6 mL, 27.85 mmol) was added drop wise over 10 minutes to a stirred solution of 4-bromo-2-chloroaniline (5.0 g, 24.22 mmol) in a mixture of methanol (50 mL) and acetic acid (95 mL) and the resulting solution was heated to 70° C. and stirred at this temperature for 4 hours. After this time, the reaction mixture was cooled to room temperature and concentrated. The resulting residue was then dissolved in THF (25 mL) and added drop wise to a cooled (0° C.), stirred solution of sodium borohydride (1.87 g, 49.4 mmol) and (diethyl ether)(trifluoro)boron (6.2 mL, 48.9 mmol) in THF (50 mL). The resulting mixture was then heated to 70° C. and stirred at this temperature for 4 hours before being cooled to room temperature and allowed to stand overnight. The resulting reaction mixture was quenched by the addition of water (100 mL) before being extracted with ethyl acetate (3×30 mL). The combined organic extracts were washed sequentially with water (100 mL) and brine (100 mL) before being dried (MgSO4), filtered and concentrated. The resulting residue was purified on a Biotage isolera (5% ethyl acetate, 95% heptanes) to give the desired compound (4.8 g, 76% yield) as a colourless oil. Tr=2.44 min m/z (ES+) (M+H+) 246/248.

Referring to Reaction Scheme 25, Stage 2. Sodium hydride (60% dispersion in oil, 0.29 g, 7.28 mmol) was added in one portion to a cooled (0° C.) stirred solution of 4-bromo-2-chloro-N-cyclopropylaniline (1.4 g, 5.68 mmol) in dry DMF (35 mL) and the resulting solution was stirred for 5 minutes. After this time, iodomethane (0.35 mL, 5.62 mmol) was added and the reaction mixture was stirred for 10 minutes before being allowed to warm to room temperature and stirred for a further 6 hours under a nitrogen atmosphere. The resulting reaction mixture was extracted with ethyl acetate (3×25 mL) and the organic layer washed sequentially with water (75 mL) and brine (75 ml) before being dried (MgSO4), filtered and concentrated. The resulting residue was purified by dry flash chromatography (elution: 100% heptanes) to give the desired compound (1.44 g, 78% yield) as a colourless oil. 6H (500 MHz, DMSO) 7.56 (d, J=2.36 Hz, 1H), 7.46 (dd, J=8.67, 2.36 Hz, 1H), 7.31 (d, J=8.67 Hz, 1H), 2.81 (s, 3H), 2.53-2.58 (m, 1H), 0.63-0.69 (m, 2H), 0.27-0.33 (m, 2H).

Referring to Reaction Scheme 25, Stages 3, 4 & 5 were carried out as described in Reaction Scheme 15.

The following compounds were prepared substantially as described above.

| Structure | Molecular Weight | Mass Spec Result |
|---|---|---|
| (cyclopropyl-NH, Cl, pyrimidine-COOH structure) | 289.72 | [M + H]+ = 290/292, 98% @ rt = 3.77 min |
| (cyclopropyl-N(CH3), Cl, pyrimidine-COOH structure) | 303.75 | [M + H]+ = 304/306, 100% @ rt = 4.40 min |

Example 26

Reaction Scheme 26

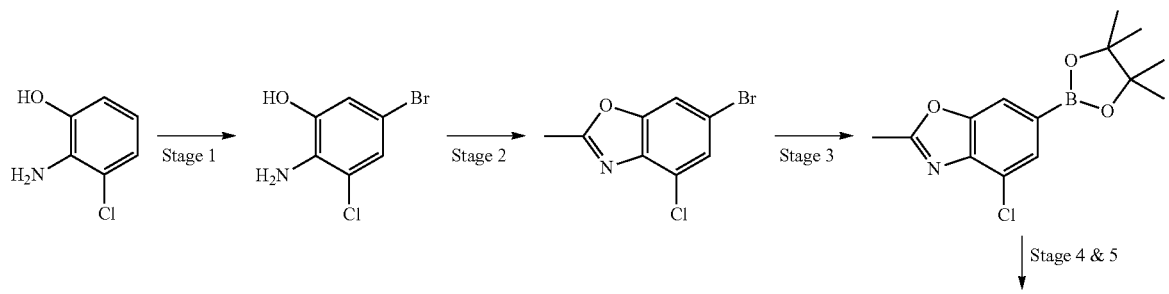

Referring to Reaction Scheme 26, Stage 1. Bromine (0.54 mL, 10.4 mmol) was added drop wise to a cooled (0° C.), stirred solution of 2-amino-3-chlorophenol (1.0 g, 6.97 mmol) in DCM (50 mL) and the resulting solution was warmed to room temperature and stirred for 16 hours. After this time, the reaction mixture was cooled in an ice-bath and bromine (0.11 mL, 2.09 mmol) was added before being warmed to room temperature and stirred for a further 1 hour. The resulting solid precipitate was collected by filtration, suspended in DCM (100 mL) and washed with saturated sodium bicarbonate (50 mL). The organic layer was removed, washed sequentially with water (10 mL) and brine (10 mL), before being dried (MgSO4), filtered and concentrated to give the desired compound (1.0 g, 64% yield) as a red solid. δH (500 MHz, DMSO) 10.13 (br. s., 1H), 6.89 (d, J=2.21 Hz, 1H), 6.75 (d, J=2.21 Hz, 1H), 4.82 (br. s., 2H).

Referring to Reaction Scheme 26, Stage 2. p-Toluene sulfonic acid (0.02 g, 0.12 mmol) was added in one portion to a stirred solution of 2-amino-5-bromo-3-chlorophenol (0.9 g, 4.05 mmol) in triethylorthoacetate (10 mL) and the resulting reaction mixture was heated to 140° C. and stirred at this temperature for 18 hours. After this time, the reaction mixture was cooled to room temperature and partitioned between water (10 mL) and ethyl acetate (20 mL). The organic layer was removed, washed sequentially with water (10 mL), saturated sodium bicarbonate (2×20 mL) and brine (10 mL) before being dried (MgSO4), filtered and concentrated. The resulting residue was purified on a Biotage isolera (0% ethyl acetate, 100% heptanes to 40% ethyl acetate, 60% heptanes) to give the desired compound (0.68 g, 48% yield) as a red solid. δH (500 MHz, CDCl3) 7.58 (d, J=1.42 Hz, 1H), 7.50 (d, J=1.58 Hz, 1H), 2.61-2.73 (m, 3H).

Referring to Reaction Scheme 26, Stages 3, 4 & 5 were carried out as described in Reaction Scheme 15.

The following compounds were prepared substantially as described above.

| Structure | Molecular Weight | Mass Spec Result |
|---|---|---|
| 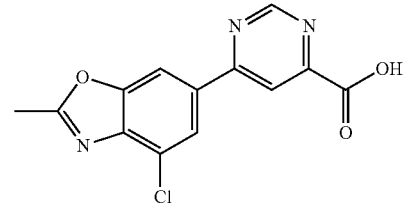 [SMILES: Cc1nc2c(Cl)cc(-c3cc(C(=O)O)ncn3)cc2o1] | 289.67 | [M + H]+ = 290/292 100% @ rt = 3.26 min |

Example 27

The following compounds may be prepared substantially as described above.

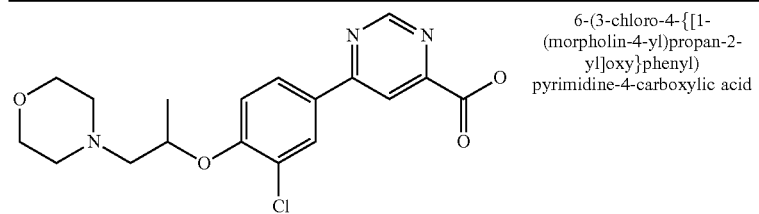 6-(3-chloro-4-{[1-(morpholin-4-yl)propan-2-yl]oxy}phenyl)pyrimidine-4-carboxylic acid

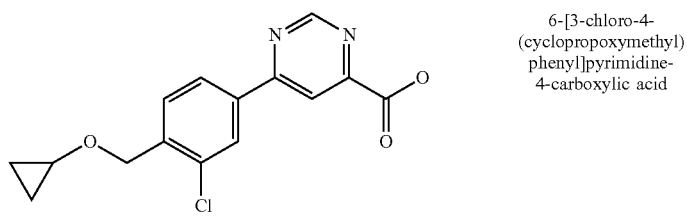 6-[3-chloro-4-(cyclopropoxymethyl)phenyl]pyrimidine-4-carboxylic acid

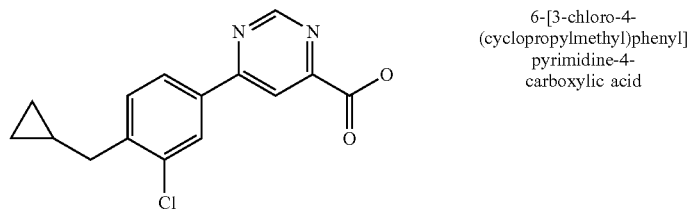 6-[3-chloro-4-(cyclopropylmethyl)phenyl]pyrimidine-4-carboxylic acid

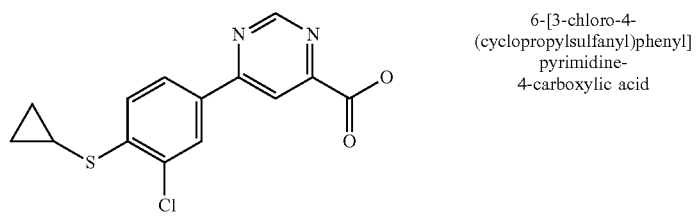 6-[3-chloro-4-(cyclopropylsulfanyl)phenyl]pyrimidine-4-carboxylic acid

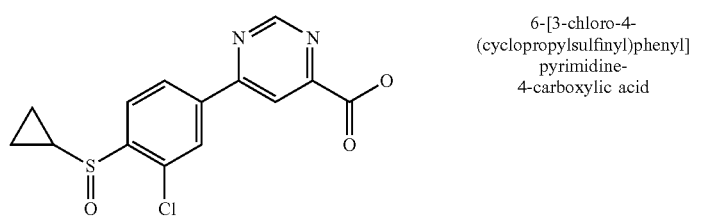 6-[3-chloro-4-(cyclopropylsulfinyl)phenyl]pyrimidine-4-carboxylic acid

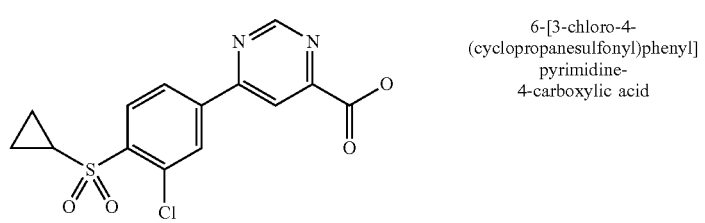 6-[3-chloro-4-(cyclopropanesulfonyl)phenyl]pyrimidine-4-carboxylic acid

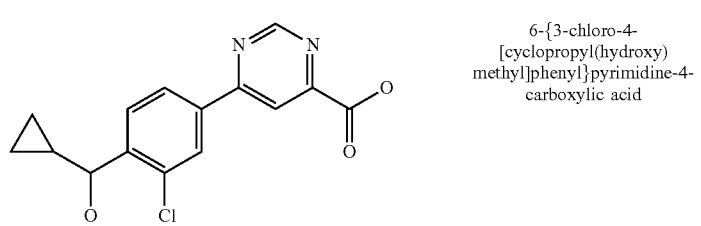 6-{3-chloro-4-[cyclopropyl(hydroxy)methyl]phenyl}pyrimidine-4-carboxylic acid

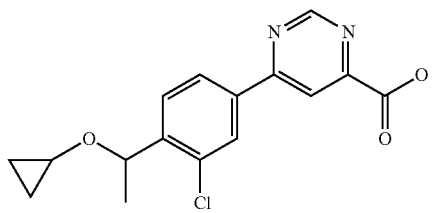 [SMILES: CC(OC1CC1)c1ccc(-c2cc(C(=O)O)ncn2)cc1Cl]
6-[3-chloro-4-(1-cyclopropoxyethyl)phenyl]pyrimidine-4-carboxylic acid

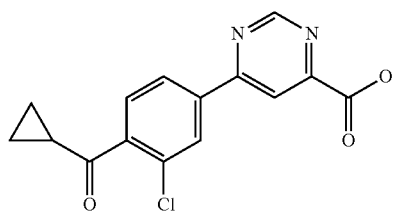 [SMILES: O=C(O)c1cc(-c2ccc(C(=O)C3CC3)c(Cl)c2)ncn1]
6-(3-chloro-4-cyclopropanecarbonylphenyl)pyrimidine-4-carboxylic acid

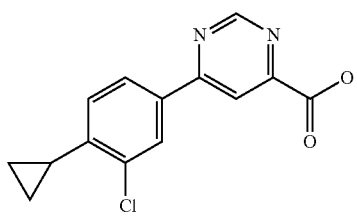 [SMILES: O=C(O)c1cc(-c2ccc(C3CC3)c(Cl)c2)ncn1]
6-(3-chloro-4-cyclopropylphenyl)pyrimidine-4-carboxylic acid

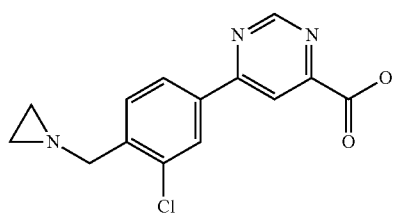 [SMILES: O=C(O)c1cc(-c2ccc(CN3CC3)c(Cl)c2)ncn1]
6-[4-(aziridin-1-ylmethyl)-3-chlorophenyl]pyrimidine-4-carboxylic acid

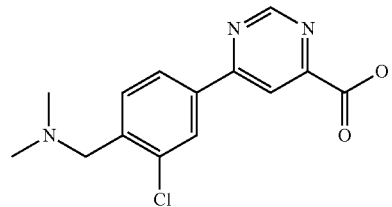 [SMILES: CN(C)Cc1ccc(-c2cc(C(=O)O)ncn2)cc1Cl]
6-{3-chloro-4-[(dimethylamino)methyl]phenyl}pyrimidine-4-carboxylic acid

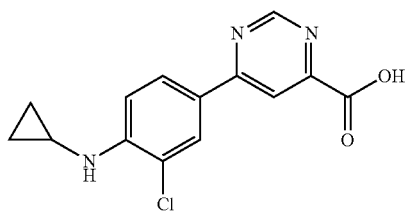 [SMILES: O=C(O)c1cc(-c2ccc(NC3CC3)c(Cl)c2)ncn1]
6-[3-chloro-4-(cyclopropylamino)phenyl]pyrimidine-4-carboxylic acid

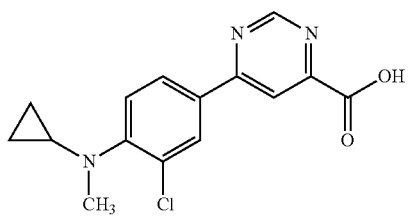 [SMILES: CN(c1ccc(-c2cc(C(=O)O)ncn2)cc1Cl)C1CC1]
6-{3-chloro-4-[cyclopropyl(methyl)amino]phenyl}pyrimidine-4-carboxylic acid

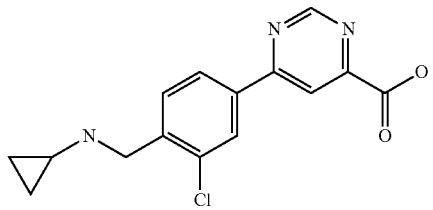 [SMILES: O=C(O)c1cc(-c2ccc(CNC3CC3)c(Cl)c2)ncn1]

6-{3-chloro-4-[(cyclopropylamino)methyl]phenyl}pyrimidine-4-carboxylic acid

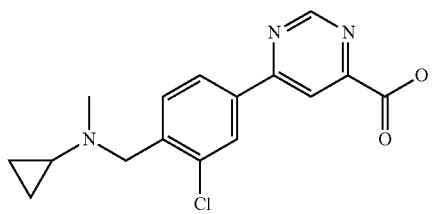 [SMILES: CN(Cc1ccc(-c2cc(C(=O)O)ncn2)cc1Cl)C1CC1]

6-(3-chloro-4-{[cyclopropyl(methyl)amino]methyl}phenyl)pyrimidine-4-carboxylic acid

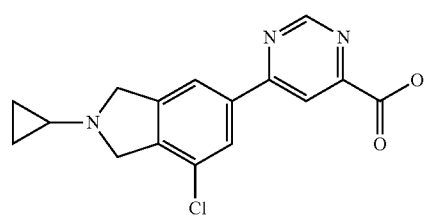 [SMILES: O=C(O)c1cc(-c2cc(Cl)c3c(c2)CN(C2CC2)C3)ncn1]

6-(7-chloro-2-cyclopropyl-2,3-dihydro-1H-isoindol-5-yl)pyrimidine-4-carboxylic acid

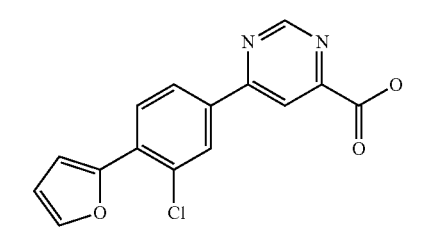 [SMILES: O=C(O)c1cc(-c2ccc(-c3ccco3)c(Cl)c2)ncn1]

6-[3-chloro-4-(furan-2-yl)phenyl]pyrimidine-4-carboxylic acid

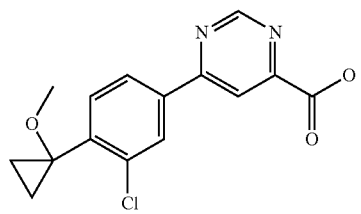 [SMILES: COC1(c2ccc(-c3cc(C(=O)O)ncn3)cc2Cl)CC1]

6-[3-chloro-4-(1-methoxycyclopropyl)phenyl]pyrimidine-4-carboxylic acid

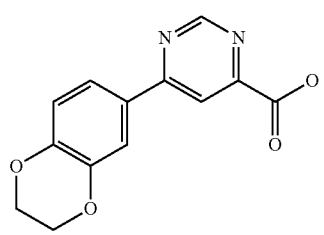 [SMILES: O=C(O)c1cc(-c2ccc3c(c2)OCCO3)ncn1]

6-(2,3-dihydro-1,4-benzodioxin-6-yl)pyrimidine-4-carboxylic acid

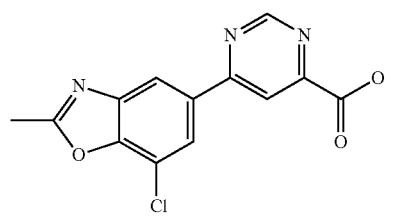 [SMILES: Cc1nc2cc(-c3cc(C(=O)O)ncn3)cc(Cl)c2o1]

6-(7-chloro-2-methyl-1,3-benzoxazol-5-yl)pyrimidine-4-carboxylic acid

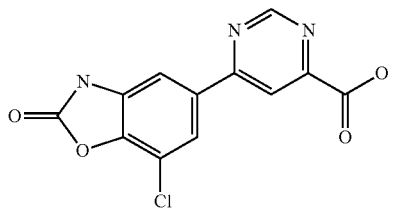 [SMILES: O=C(O)c1cc(-c2cc(Cl)c3oc(=O)[nH]c3c2)ncn1]
6-(7-chloro-2-oxo-2,3-dihydro-1,3-benzoxazol-5-yl)pyrimidine-4-carboxylic acid

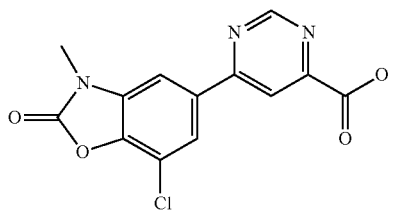 [SMILES: Cn1c(=O)oc2c(Cl)cc(-c3cc(C(=O)O)ncn3)cc21]
6-(7-chloro-3-methyl-2-oxo-2,3-dihydro-1,3-benzoxazol-5-yl)pyrimidine-4-carboxylic acid

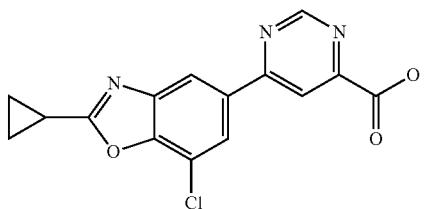 [SMILES: O=C(O)c1cc(-c2cc(Cl)c3oc(C4CC4)nc3c2)ncn1]
6-(7-chloro-2-cyclopropyl-1,3-benzoxazol-5-yl)pyrimidine-4-carboxylic acid

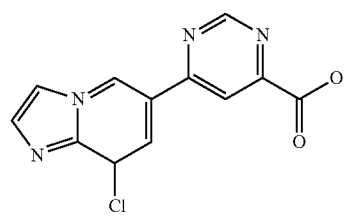
6-{8-chloroimidazo[1,2-a]pyridin-6-yl}pyrimidine-4-carboxylic acid

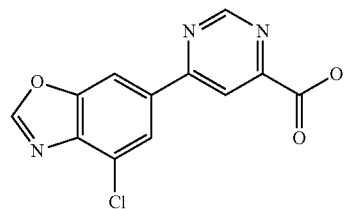 [SMILES: O=C(O)c1cc(-c2cc(Cl)c3ncoc3c2)ncn1]
6-(4-chloro-1,3-benzoxazol-6-yl)pyrimidine-4-carboxylic acid

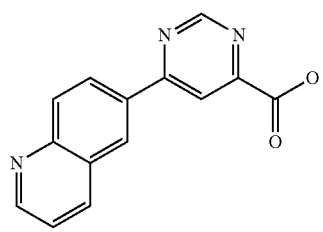 [SMILES: O=C(O)c1cc(-c2ccc3ncccc3c2)ncn1]
6-(quinolin-6-yl)pyrimidine-4-carboxylic acid

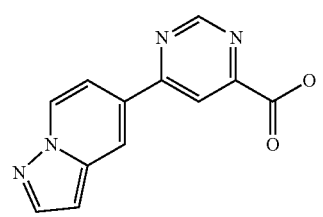 [SMILES: O=C(O)c1cc(-c2ccn3nccc3c2)ncn1]
6-{pyrazolo[1,5-a]pyridin-5-yl}pyrimidine-4-carboxylic acid

-continued
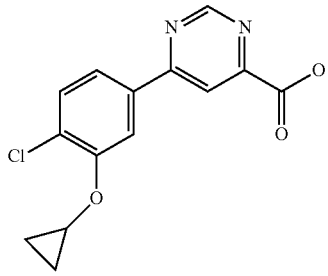 [SMILES: O=C(O)c1cc(-c2ccc(Cl)c(OC3CC3)c2)ncn1]
6-(4-chloro-3-cyclopropoxyphenyl)pyrimidine-4-carboxylic acid
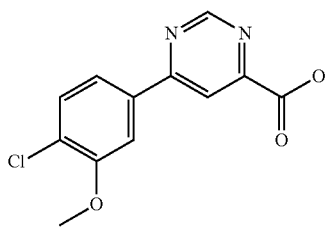 [SMILES: COc1cc(-c2cc(C(=O)O)ncn2)ccc1Cl]
6-(4-chloro-3-methoxyphenyl)pyrimidine-4-carboxylic acid
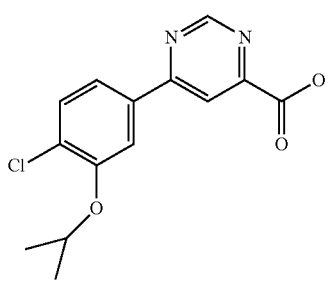 [SMILES: CC(C)Oc1cc(-c2cc(C(=O)O)ncn2)ccc1Cl]
6-[4-chloro-3-(propan-2-yloxy)phenyl]pyrimidine-4-carboxylic acid
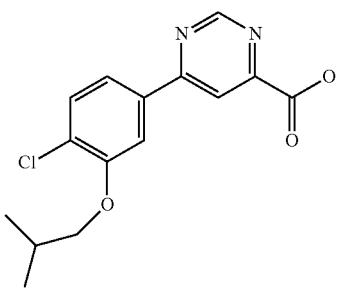 [SMILES: CC(C)COc1cc(-c2cc(C(=O)O)ncn2)ccc1Cl]
6-[4-chloro-3-(2-methylpropoxy)phenyl]pyrimidine-4-carboxylic acid
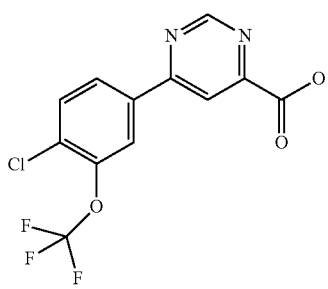 [SMILES: O=C(O)c1cc(-c2ccc(Cl)c(OC(F)(F)F)c2)ncn1]
6-[4-chloro-3-(trifluoromethoxy)phenyl]pyrimidine-4-carboxylic acid

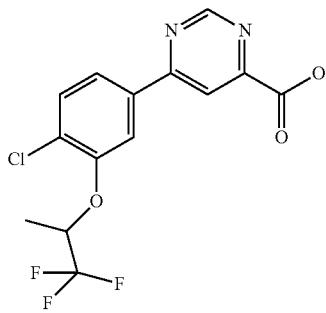 [SMILES: CC(Oc1cc(-c2cc(C(=O)O)ncn2)ccc1Cl)C(F)(F)F]
6-{4-chloro-3-[(1,1,1-trifluoropropan-2-yl)oxy]phenyl}pyrimidine-4-carboxylic acid
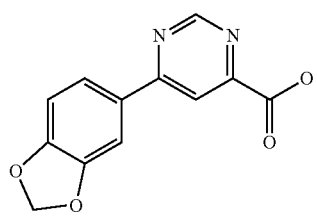 [SMILES: O=C(O)c1cc(-c2ccc3c(c2)OCO3)ncn1]
6-(benzo[d][1,3]dioxol-5-yl)pyrimidine-4-carboxylic acid
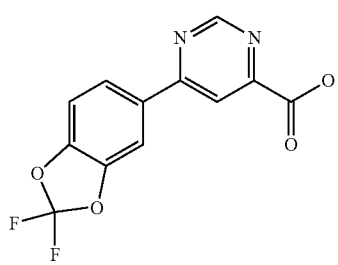 [SMILES: O=C(O)c1cc(-c2ccc3c(c2)OC(F)(F)O3)ncn1]
6-(2,2-difluorobenzo[d][1,3]dioxol-5-yl)pyrimidine-4-carboxylic acid
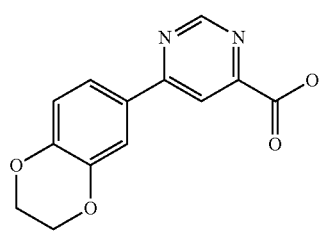 [SMILES: O=C(O)c1cc(-c2ccc3c(c2)OCCO3)ncn1]
6-(2,3-dihydrobenzo[b][1,4]dioxin-6-yl)pyrimidine-4-carboxylic acid
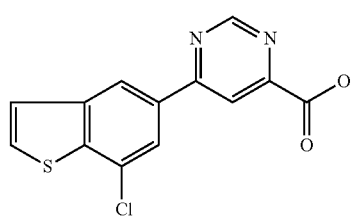 [SMILES: O=C(O)c1cc(-c2cc(Cl)c3sccc3c2)ncn1]
6-(7-chlorobenzo[b]thiophen-5-yl)pyrimidine-4-carboxylic acid
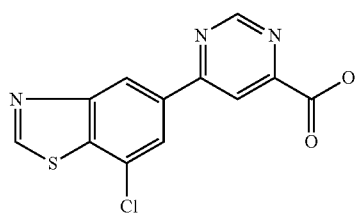 [SMILES: O=C(O)c1cc(-c2cc(Cl)c3scnc3c2)ncn1]
6-(7-chlorobenzo[d]thiazol-5-yl)pyrimidine-4-carboxylic acid

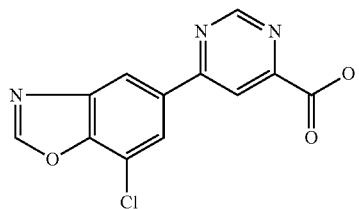 [SMILES: O=C(O)c1cc(-c2cc(Cl)c3ocnc3c2)ncn1]

6-(7-chlorobenzo[d]oxazol-5-yl)pyrimidine-4-carboxylic acid

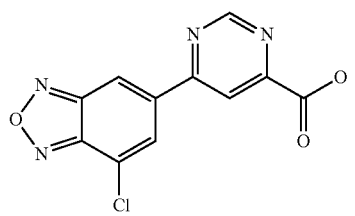 [SMILES: O=C(O)c1cc(-c2cc(Cl)c3nonc3c2)ncn1]

6-(7-chlorobenzo[c][1,2,5]oxadiazol-5-yl)pyrimidine-4-carboxylic acid

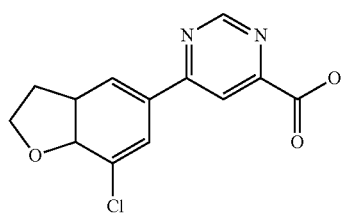 [SMILES: O=C(O)c1cc(C2=CC3CCOC3C(Cl)=C2)ncn1]

6-(7-chloro-2,3,3a,7a-tetrahydrobenzofuran-5-yl)pyrimidine-4-carboxylic acid

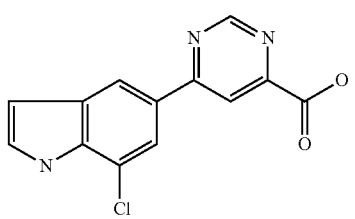 [SMILES: O=C(O)c1cc(-c2cc(Cl)c3[nH]ccc3c2)ncn1]

6-(7-chloro-3a,7a-dihydro-1H-indol-5-yl)pyrimidine-4-carboxylic acid

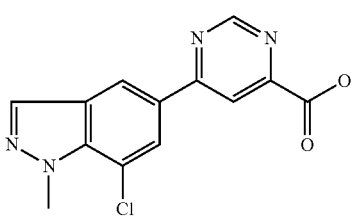 [SMILES: Cn1ncc2cc(-c3cc(C(=O)O)ncn3)cc(Cl)c21]

6-(7-chloro-1-methyl-3a,7a-dihydro-1H-indazol-5-yl)pyrimidine-4-carboxylic acid

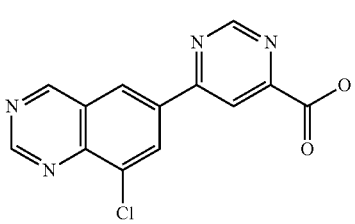 [SMILES: O=C(O)c1cc(-c2cc(Cl)c3ncncc3c2)ncn1]

6-(8-chloroquinazolin-6-yl)pyrimidine-4-carboxylic acid

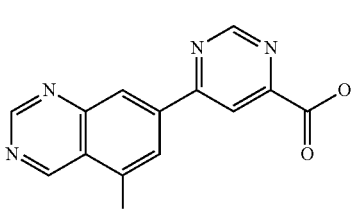

6-(5-chloroquinazolin-7-yl)pyrimidine-4-carboxylic acid

-continued

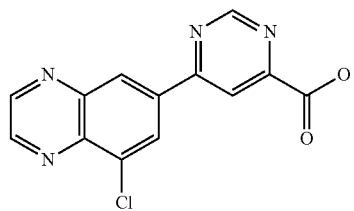 [SMILES: O=C(O)c1cc(-c2cc(Cl)c3nccnc3c2)ncn1]
6-(8-chloroquinoxalin-6-yl)pyrimidine-4-carboxylic acid

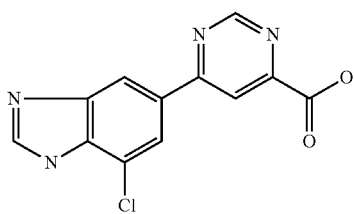 [SMILES: O=C(O)c1cc(-c2cc(Cl)c3[nH]cnc3c2)ncn1]
6-(7-chloro-1H-benzo[d]imidazol-5-yl)pyrimidine-4-carboxylic acid

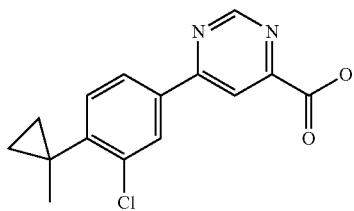 [SMILES: CC1(c2ccc(-c3cc(C(=O)O)ncn3)cc2Cl)CC1]
6-(3-chloro-4-(1-methylcyclopropyl)phenyl)pyrimidine-4-carboxylic acid

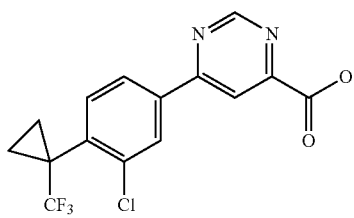 [SMILES: O=C(O)c1cc(-c2ccc(C3(C(F)(F)F)CC3)c(Cl)c2)ncn1]
6-(3-chloro-4-(1-(trifluoromethyl)cyclopropyl)phenyl)pyrimidine-4-carboxylic acid

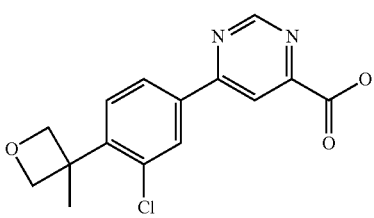 [SMILES: CC1(c2ccc(-c3cc(C(=O)O)ncn3)cc2Cl)COC1]
6-(3-chloro-4-(3-methyloxetan-3-yl)phenyl)pyrimidine-4-carboxylic acid

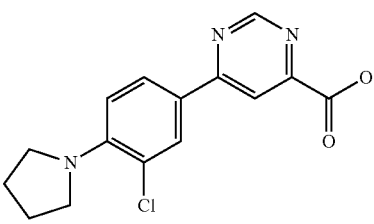 [SMILES: O=C(O)c1cc(-c2ccc(N3CCCC3)c(Cl)c2)ncn1]
6-(3-chloro-4-(pyrrolidin-1-yl)phenyl)pyrimidine-4-carboxylic acid

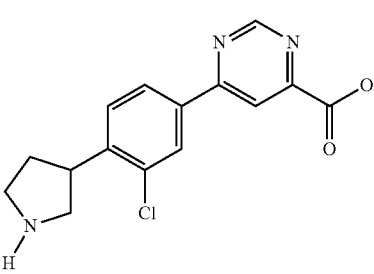 [SMILES: O=C(O)c1cc(-c2ccc(C3CCNC3)c(Cl)c2)ncn1]
6-(3-chloro-4-(pyrrolidin-3-yl)phenyl)pyrimidine-4-carboxylic acid

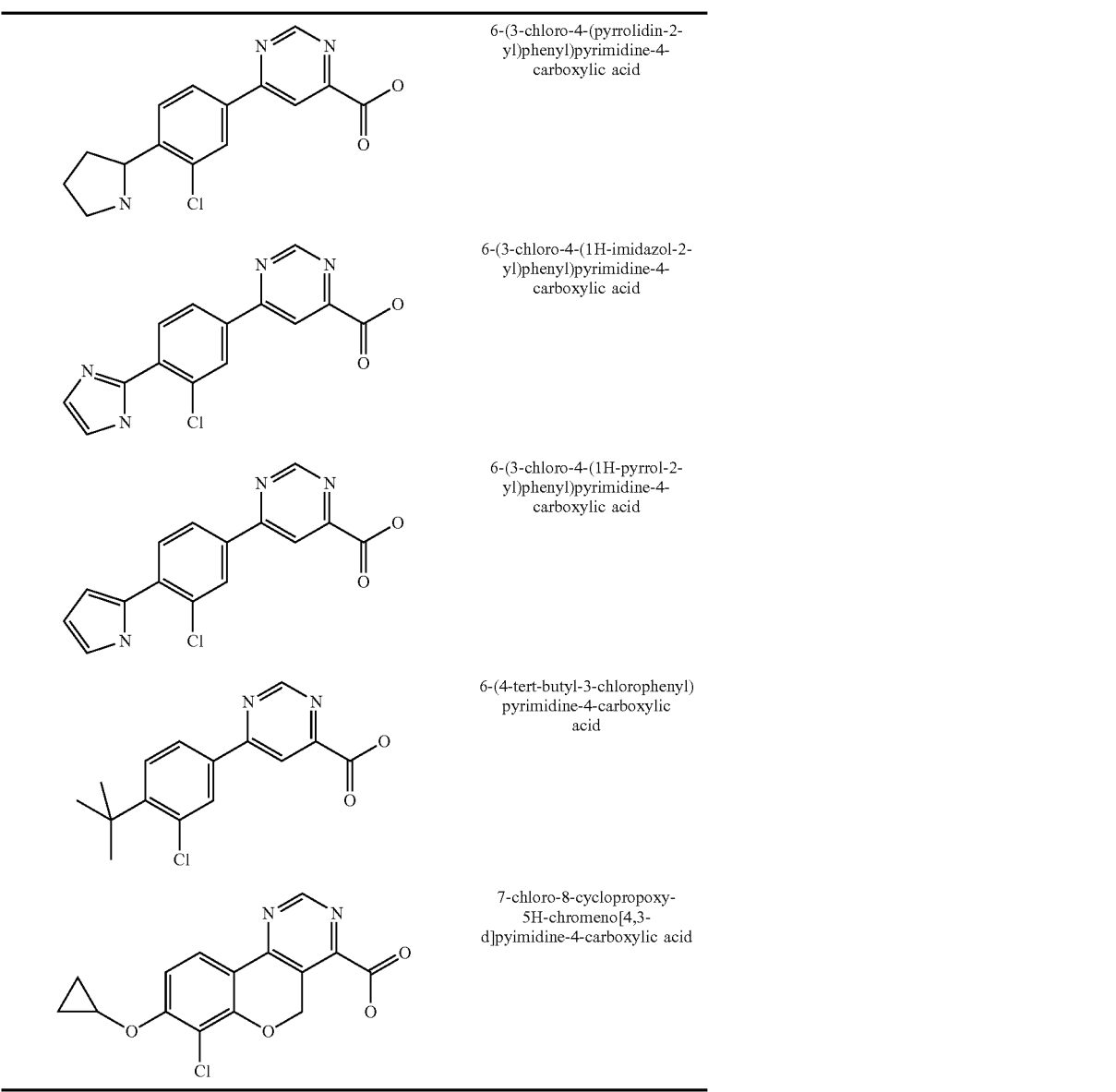

| | |
|---|---|
| | 6-(3-chloro-4-(pyrrolidin-2-yl)phenyl)pyrimidine-4-carboxylic acid |
| | 6-(3-chloro-4-(1H-imidazol-2-yl)phenyl)pyrimidine-4-carboxylic acid |
| | 6-(3-chloro-4-(1H-pyrrol-2-yl)phenyl)pyrimidine-4-carboxylic acid |
| | 6-(4-tert-butyl-3-chlorophenyl)pyrimidine-4-carboxylic acid |
| | 7-chloro-8-cyclopropoxy-5H-chromeno[4,3-d]pyimidine-4-carboxylic acid |

Example 28

A generalized procedure for monitoring L-Kynurenine (KYN) hydroxylation to form product 3-Hydroxy-Kynurenine (3OH-KYN) by LC/MS is described below. Product is quantified by multiple reaction monitoring using MS.

Key Reagents:
Compound: Stock concentrations: 10 mM in 100% DMSO
Cell line: CHO GST HIS KMO cell line, 1E4 cells/well/100 µl in 96 well cell plate
Substrate: L-Kynurenine (Sigma: Cat# K3750, stock concentration: 10 mM in 100 mM potassium phosphate buffer, pH 7.4)
Assay Conditions:
Medium: OptiMem (Reduced Serum Medium 1×, +L-Glutamine+HEPES—Phenol Red; GIBCO: Cat#11058)
Assay Volume: 200 µl
Plate Format: 96 well plate, transparent (Corning)
Read-Out: product (3OH-KYN) quantification using product specific MRM
Reader: LC/MS/MS
Assay Protocol:
prepare serial dilution (factor 3) of compound in 100% DMSO (top concentration=6.67 mM, 100% DMSO)
[8 points: 6.67 mM; 2.22 mM; 0.74 mM; 0.247 mM; 0.082 mM; 0.027 mM; 0.009 mM; 0.003 mM]
prepare 300-fold concentrated solution of each compound concentration (top concentration 22.22 µM, 0.3% DMSO) in OptiMem medium
[22.2 µM; 7.41 µM; 2.47 µM; 0.82 µM; 0.27 µM; 0.09 µM; 0.03 µM; 0.041M]
prepare substrate (10 mM) at concentration of 1.1 mM in medium
medium of cell plate is drawed off
cells are washed with OptiMem (100 µl/well) and drawed off again
assay mix: 90 µl OptiMem/well+90 µl compound/well of each concentration
[final compound top concentration: 10 µM; 0.15% DMSO]

[final compound bottom concentration: 0.004 µM; 0.15% DMSO]
pre-incubation: 30 min at 37° C.
add 20 µl/well of the 1.1 mM substrate solution (final assay concentration: 100 µM)
positive control: 200 µl OptiMem
negative control: 180 µl OptiMem+20 µl 1.1 mM substrate
incubate ~24 h at 37° C.
transfer 100 µl of each well in a transparent 96 well plate (Corning)
add 100 µl/well 10% trichloro acetic acid (TCA) in water
centrifugate plate for 3 min at 4000 rpm
detect product by LC/MS (injection of 50 µl/well; 2.5 fold overfill of the 20 µl sample loop)

Data Analysis:
$IC_{50}$'s are calculated using automated fitting algorithm (A+Analysis).

Example 29

A method of monitoring L-Kynurenine (KYN) hydroxylation to form product 3-Hydroxy-Kynurenine (3OH-KYN) by LC/MS is described below. Product is quantified by multiple reaction monitoring.

Key Reagents:
Compound: Stock concentrations: 10 mM in 100% DMSO
Enzyme: KMO enzyme prepared at Evotec via mitochondria isolation from CHO-GST HIS KMO cells
Substrate: L-Kynurenine (Sigma: Cat# K3750)
  [stock concentration: 10 mM in 100 mM potassium phosphate buffer, pH 7.4]
Assay Conditions:
Buffer: 100 mM potassium phosphate, pH 7.4, 200 µM NADPH, 0.4 U/ml G6P-DH (Glucose 6-phosphate dehydrogenase), 3 mM G6P (D-Glucose 6-phosphate)
Assay Volume: 40 µl
Plate Format: 384 well plate, transparent (Matrix)
Read-Out: product (3OH-KYN) quantification using product specific MRM
Reader: LC/MS/MS
Assay Protocol:
  prepare serial dilution (factor 3) of compound in 100% DMSO (top concentration=10 mM, 100% DMSO)
  [8 points: 10 mM; 3.33 mM; 1.11 mM; 0.37 mM; 0.12 mM; 0.04 mM; 0.0137 mM; 0.0045 mM, 0.0015 mM]
  prepare 3.33-fold concentrated solution of each compound concentration (top concentration 300 µM, 3% DMSO) in assay buffer
  [concentrations: 300 µM; 100 µM; 33.3 µM; 11.1 µM; 3.70 µM; 1.23 µM; 0.41 µM; 0.137 µM]
  prepare substrate (10 mM) at concentration of 1 mM in assay buffer
  assay mix: 4 µl compound/well of each concentration+24 µl assay buffer/well+8 µl KMO human enzyme+4 µl 1 mM substrate (final concentration=100 µM)
  [final compound top concentration: 30 µM; 0.3% DMSO]
  [final compound bottom concentration: 0.0137 µM; 0.3% DMSO]
  positive control: 4 µl 50 µM FCE28833 in assay buffer [0.5% DMSO] (final assay concentration=5 µM)+24 µl assay buffer/well+8 µl KMO human enzyme+4 µl 1 mM substrate (final concentration=100 µM)
  negative control: 28 µl assay buffer/well+8 µl KMO human enzyme+4 µl 1 mM substrate (final concentration=100 µM)
  incubate 400 min at RT
  add 40 µl/well 10% trichloro acetic acid in water to stop the assay and precipitate protein
  centrifuge plate for 3 min at 4000 rpm
  product detection by LC/MS (injection of 50 µl/well; 2.5 fold overfill of the 20 µl sample loop)

Data Analysis:
$IC_{50}$'s are calculated using automated fitting algorithm (A+Analysis).

Example 30

A method of monitoring L-Kynurenine (KYN) hydroxylation to form 3-Hydroxy-Kynurenine (3OH-KYN) by LC/MS is described. Product is quantified by multiple reaction monitoring (MRM method).

Key Reagents:
Compound: Stock concentrations: 10 mM in 100% DMSO
Enzyme: KMO enzyme prepared at Evotec from mouse liver (4-6 weeks old) via mitochondria isolation as described in the literature
Substrate: L-Kynurenine (Sigma: Cat# K3750, stock concentration: 10 mM in 100 mM potassium phosphate buffer, pH 7.4)
Assay Conditions:
Buffer: 100 mM potassium phosphate, pH 7.4, 200 µM NADPH, 0.4 U/ml G6P-DH (Glucose 6-phosphate Dehydrogenase), 3 mM G6P (D-Glucose 6-phosphate)
Assay Volume: 40 µl
Plate Format: 384 well plate, transparent (Matrix)
Read-Out: product (3OH-KYN) quantification using product specific MRM
Reader: LC/MS/MS
Assay Protocol:
  prepare serial dilution (factor 3) of compound in 100% DMSO (top concentration=10 mM, 100% DMSO)
  [8 points: 10 mM; 3.33 mM; 1.11 mM; 0.37 mM; 0.12 mM; 0.04 mM; 0.0137 mM; 0.0045 mM, 0.0015 mM]
  prepare 3.33-fold concentrated solution of each compound concentration (top concentration 300 µM, 3% DMSO) in assay buffer
  [concentrations: 300 µM; 100 µM; 33.3 µM; 11.1 µM; 3.70 µM; 1.23 µM; 0.41 µM; 0.137 µM]
  prepare substrate (10 mM) at concentration of 1 mM in assay buffer
  assay mix: 4 µl compound/well of each concentration+24 µl assay buffer/well+8 µl KMO mouse enzyme+4 µl 1 mM substrate (final concentration=100 µM)
  [final compound top concentration: 30 µM; 0.3% DMSO]
  [final compound bottom concentration: 0.0137 µM; 0.3% DMSO]
  positive control: 4 µl 50 µM FCE28833 in assay buffer, 0.5% DMSO [final assay concentration=5 µM]+24 µl assay buffer/well+8 µl KMO mouse enzyme+4 µl 1 mM substrate [final concentration=100 µM]
  negative control: 28 µl assay buffer/well+8 µl KMO mouse enzyme+4 µl 1 mM substrate [final concentration=100 µM]
  incubate 40 min at RT
  add 40 µl/well 10% trichloro acetic acid in water to stop the assay and precipitate protein
  centrifuge plate for 3 min at 4000 rpm
  product detection by LC/MS (injection of 20 µl/well, 2 fold overfill of the 10 µl sample loop)

Data Analysis:

IC$_{50}$'s are calculated using automated fitting algorithm (A+Analysis).

Example 31

Using procedures similar to those described herein, the following compounds were assayed for activity.

| IUPAC name | % Inhibition at 10 uM* |
|---|---|
| 6-(4-Chloro-3-methoxy-phenyl)-pyrimidine-4-carboxylic acid | 99.62 |
| 6-(3-Amino-4-chloro-phenyl)-pyrimidine-4-carboxylic acid | 101.01 |
| 6-[4-Chloro-3-(tetrahydro-furan-3-yloxy)-phenyl]-pyrimidine-4-carboxylic acid pyridin-3-ylamide | 88.39 |
| 6-[4-Chloro-3-(2-morpholin-4-yl-ethoxy)-phenyl]-pyrimidine-4-carboxylic acid hydrochloride salt | 61.41 |
| 6-(3-Chloro-4-isopropyl-phenyl)-pyrimidine-4-carboxylic acid | 100 |
| 6-(3-Fluoro-4-methyl-phenyl)-pyrimidine-4-carboxylic acid | 100 |
| 6-(3-Chloro-4-isopropoxy-phenyl)-pyrimidine-4-carboxylic acid | 100 |
| 6-(3-Chloro-4-isopropoxy-phenyl)-2-methyl-pyrimidine-4-carboxylic acid | 70 |
| 6-(3-Fluoro-4-methyl-phenyl)-2-methyl-pyrimidine-4-carboxylic acid | 96 |
| 6-(3-Chloro-4-cyclopentyloxy-phenyl)-pyrimidine-4-carboxylic acid | 97 |
| 6-(3-Chloro-4-trifluoromethoxy-phenyl)-pyrimidine-4-carboxylic acid | 100 |
| 6-(3-Fluoro-4-isopropyl-phenyl)-pyrimidine-4-carboxylic acid | 85 |
| 6-(4-(R)-sec-Butoxy-3-chloro-phenyl)-pyrimidine-4-carboxylic acid | 100 |
| 6-(4-(S)-sec-Butoxy-3-chloro-phenyl)-pyrimidine-4-carboxylic acid | 100 |
| 6-(3-Chloro-4-cyclopropoxy-phenyl)-pyrimidine-4-carboxylic acid | 100 |
| 6-[3-Chloro-4-(2,2,2-trifluoro-1-methyl-ethoxy)-phenyl]-pyrimidine-4-carboxylic acid | 94 |
| 4-(3-Chloro-4-cyclopropoxy-phenyl)-pyridine-2-carboxylic acid | 100 |
| 6-(4-(R)-sec-Butoxy-3-chloro-phenyl)-pyridine-4-carboxylic acid | 50 |
| 6-(4-(S)-sec-Butoxy-3-chloro-phenyl)-pyridine-4-carboxylic acid | 82 |
| 4-(3-Chloro-4-isopropoxy-phenyl)-pyridine-2-carboxylic acid | 80 |
| 4-(3-Chloro-4-trifluoromethoxy-phenyl)-pyridine-2-carboxylic acid | 89 |
| 6-(3-Chloro-4-cyclobutoxy-phenyl)-pyrimidine-4-carboxylic acid | 100 |
| 6-[3-Chloro-4-(2-piperidin-1-yl-ethoxy)-phenyl]-pyrimidine-4-carboxylic acid | 90 |
| 6-Quinolin-6-yl-pyrimidine-4-carboxylic acid | 100 |
| 6-(8-Chloro-chroman-6-yl)-pyrimidine-4-carboxylic acid | 100 |
| 6-(7-Chloro-benzofuran-5-yl)-pyrimidine-4-carboxylic acid | 100 |
| 6-[3-Chloro-4-(pyrrolidin-3-yloxy)-phenyl]-pyrimidine-4-carboxylic acid | 80 |
| 6-(8-chloro-1-methyl-1,2,3,4-tetrahydroquinolin-6-yl)pyrimidine-4-carboxylic acid | 100 |
| 6-(8-chloroquinolin-6-yl)pyrimidine-4-carboxylate | 100 |
| N-[6-(3-chloro-4-cyclopropoxyphenyl)pyrimidin-4-yl]benzenesulfonamide | 73 |
| N-[6-(3-chloro-4-cyclopropoxyphenyl)pyrimidin-4-yl]-4-fluorobenzene-1-sulfonamide | 98 |
| N-[6-(3-chloro-4-cyclopropoxyphenyl)pyrimidin-4-yl]-4-(trifluoromethoxy)benzene-1-sulfonamide | 88 |
| N-[6-(3-chloro-4-cyclopropoxyphenyl)pyrimidin-4-yl]-3-(trifluoromethoxy)benzene-1-sulfonamide | 77 |
| N-[6-(3-chloro-4-cyclopropoxyphenyl)pyrimidin-4-yl]-2-fluorobenzene-1-sulfonamide | 96 |
| N-[6-(3-chloro-4-cyclopropoxyphenyl)pyrimidin-4-yl]cyclopropanesulfonamide | 33 |

| IUPAC name | % Inhibition at 10 uM* |
|---|---|
| 6-(8-chloro-1,2,3,4-tetrahydroquinolin-6-yl)pyrimidine-4-carboxylate | 100 |
| 6-(3-chloro-4-cyclopropoxyphenyl)-5-methylpyrimidine-4-carboxylate | 100 |
| 6-{3-chloro-4-[2-(morpholin-4-yl)ethoxy]phenyl}pyrimidine-4-carboxylate | 99 |
| 6-[3-chloro-4-(cyclopropylmethoxy)phenyl]pyrimidine-4-carboxylate | 101 |
| 6-[3-chloro-4-(oxetan-3-yloxy)phenyl]pyrimidine-4-carboxylic acid | 100 |
| 4-(3-chloro-4-cyclopropoxyphenyl)-5H,7H-furo[3,4-d]pyrimidin-7-one | 100 |
| 6-(3-chloro-4-cyclopropoxyphenyl)-5-(hydroxymethyl)pyrimidine-4-carboxylic acid | 100 |
| 4-(3-chloro-4-cyclopropoxyphenyl)-5H,6H,8H-pyrano[3,4-d]pyrimidin-8-one | 100 |
| [(2R,3S,4S,5R)-3,4,5,6-tetrahydroxyoxan-2-yl]methyl 6-(3-chloro-4-cyclopropoxyphenyl)pyrimidine-4-carboxylate | 102 |
| 6-[3-chloro-4-(methylsulfanyl)phenyl]pyrimidine-4-carboxylic acid | 103 |
| 6-[3-chloro-4-(methylsulfinyl)phenyl]pyrimidine-4-carboxylic acid | 100 |
| 6-[3-chloro-4-(methylsulfonyl)phenyl]pyrimidine-4-carboxylic acid | 100 |
| 6-{3-chloro-4-[cyclopropyl(hydroxy)methyl]phenyl}pyrimidine-4-carboxylic acid | 90 |
| 6-(3-chloro-4-cyclopropanecarbonylphenyl)pyrimidine-4-carboxylic acid | 101 |
| 6-[3-chloro-4-(methoxymethyl)phenyl]pyrimidine-4-carboxylic acid | 105 |
| 6-[3-chloro-4-(1-methoxyethyl)phenyl]pyrimidine-4-carboxylic acid | 101 |
| 6-{3-chloro-4-[(dimethylamino)methyl]phenyl}pyrimidine-4-carboxylic acid | 65 |
| 6-[3-chloro-4-(cyclopropylamino)phenyl]pyrimidine-4-carboxylic acid | 101 |
| 6-{3-chloro-4-[cyclopropyl(methyl)amino]phenyl}pyrimidine-4-carboxylic acid | 96 |
| 6-(3-chloro-4-(pyrrolidin-1-yl)phenyl)pyrimidine-4-carboxylic acid | 100 |
| 6-(7-chloro-2-methyl-1,3-benzoxazol-5-yl)pyrimidine-4-carboxylic acid | 102 |
| 6-(8-chloroquinoxalin-6-yl)pyrimidine-4-carboxylic acid | 102 |
| 6-(7-chloro-2,3-dihydro-1-benzofuran-5-yl)pyrimidine-4-carboxylic acid | 102 |
| 6-(7-chloro-2-cyclopropyl-1,3-benzoxazol-5-yl)pyrimidine-4-carboxylic acid | 100 |
| 6-(4-chloro-2-methyl-1,3-benzoxazol-6-yl)pyrimidine-4-carboxylic acid | 102 |
| 6-(7-chloro-3-methyl-2-oxo-2,3-dihydro-1,3-benzoxazol-5-yl)pyrimidine-4-carboxylic acid | 100 |
| 6-(2H-1,3-benzodioxol-5-yl)pyrimidine-4-carboxylic acid | 101 |

*Some portion of activity of amides may be due to contribution of acid precursor.

Example 32: General Procedures

Method A.

Amide coupling. To a solution of carboxylic acid (1 eq) in DMF were added EDC.HCl (1 eq) and HOBt (1 to 1.2 eq) or HATU (1 to 1.2 eq). The reaction mixture was stirred at ambient temperature for 30 minutes after which time the appropriate amine (1 eq) was added. The reaction was monitored by LCMS to completion whereupon the reaction mixture was poured into water. The resultant precipitate was filtered, washed with water (×2), heptane (×2) and dried in vacuo to yield the target compound. If a precipitate was not formed the reaction mixture was extracted with EtOAc (×3) and the combined organic layers were washed with water (×2), saturated aqueous NaCl (×2), dried (Na2SO4 or MgSO4) and the solvent removed in vacuo to afford the crude product. Purification was carried out by flash column chromatography, prep HPLC, or a combination of both.

Method B.

Amide coupling. To a solution of carboxylic acid (1 eq) in DCM (20 vol) under nitrogen were added oxalyl chloride (3 eq) and 1 drop of DMF (cat.). The reaction mixture was stirred at ambient temperature for 30 minutes after which time the solvents were removed in vacuo. DCM (20 vol) or THF (20 vol) was added, followed by the required amine (1 to 3 eq) and triethylamine (2 eq) or DIPEA (1.5 eq). The reaction mixture was stirred at ambient temperature. The reaction was monitored by LCMS to completion whereupon water was added. The reaction mixture was then extracted with DCM and the organic layer was washed with water, saturated aqueous NaCl, dried over Na2SO4 or MgSO4 and the solvent removed in vacuo to afford the crude product. Purification was carried out by flash column chromatography, prep HPLC, a combination of both or by trituration with an appropriate solvent.

Method C.

Amide coupling. To a solution of carboxylic acid (1 eq) in DMF were added EDC.HCl (1 eq) and HOBt (1 eq). The reaction mixture was stirred at ambient temperature for 30 minutes after which time the appropriate amine was added. The reaction was monitored by LCMS. After completion the reaction mixture was poured into water after which a precipitate came out of solution and was filtered, washed with water, heptane and dried in vacuo to yield the target compound or if a precipitate was not formed the reaction mixture was extracted with EtOAc (3×) and the combined organic layers were washed with water, saturated aqueous NaCl, dried (Na2SO4 or MgSO4) and the solvent removed in vacuo to afford the crude product. Purification was carried out by flash column chromatography, prep HPLC, or a combination of both.

Method D.

Amide coupling. To a solution of carboxylic acid (1 eq) in DCM (20 vol) under nitrogen were added oxalyl chloride (3 eq) and DMF (cat). The reaction mixture was stirred at ambient temperature for 30 minutes after which time the solvents were removed in vacuo. DCM (20 vol) or THF (20 vol) was added, followed by the required amine (1 to 3 eq) and triethylamine (2 eq) and the reaction mixture was stirred at ambient temperature. The reaction was monitored by LCMS to completion whereupon water was added. The reaction mixture was then extracted with DCM and the organic layer was washed with water, saturated aqueous NaCl, dried over Na2SO4 or MgSO4 and the solvent removed in vacuo to afford the crude product. Purification was carried out by flash column chromatography, prep HPLC, a combination of both or by trituration with an appropriate solvent.

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed:

1. A compound of formula:

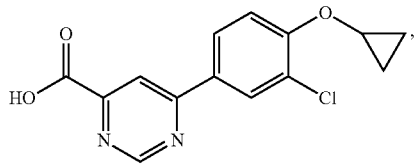 [SMILES: O=C(O)c1cc(-c2ccc(OC3CC3)c(Cl)c2)ncn1]

or a pharmaceutically acceptable salt thereof.

2. A pharmaceutical composition comprising the compound of claim 1 and at least one pharmaceutically acceptable excipient.

3. A method of treating Huntington's disease in a subject in need of such a treatment which method comprises administering to the subject a therapeutically effective amount of the compound of claim 1.

\* \* \* \* \*

UNITED STATES PATENT AND TRADEMARK OFFICE
CERTIFICATE OF CORRECTION

PATENT NO. : 9,981,918 B2  
APPLICATION NO. : 14/241374  
DATED : May 29, 2018  
INVENTOR(S) : Toledo-Sherman et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 490 days.

Signed and Sealed this
Twenty-third Day of April, 2019

Andrei Iancu
*Director of the United States Patent and Trademark Office*